(12) United States Patent
Dacey, Jr. et al.

(10) Patent No.: US 8,160,695 B2
(45) Date of Patent: Apr. 17, 2012

(54) SYSTEM FOR CHEMICAL MODULATION OF NEURAL ACTIVITY

(75) Inventors: Ralph G. Dacey, Jr., St. Louis, MO (US); Gregory J. Della Rocca, Columbia, MO (US); Colin P. Derdeyn, St. Louis, MO (US); Joshua L. Dowling, Webster Groves, MO (US); Eleanor V. Goodall, Seattle, WA (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Medina, WA (US); Michael A. Smith, Phoenix, AZ (US); Lowell L. Wood, Jr., Bellevue, WA (US); Victoria Y. H. Wood, Livermore, CA (US); Gregory J. Zipfel, St. Louis, MO (US)

(73) Assignee: The Invention Science Fund I, LLC

( * ) Notice: Subject to any disclaimer, the term of this patent is extended or adjusted under 35 U.S.C. 154(b) by 954 days.

(21) Appl. No.: 12/214,533

(22) Filed: Jun. 18, 2008

(65) Prior Publication Data
US 2009/0149896 A1    Jun. 11, 2009

Related U.S. Application Data

(63) Continuation-in-part of application No. 12/080,789, filed on Apr. 4, 2008, and a continuation-in-part of application No. 12/080,787, filed on Apr. 4, 2008, and a continuation-in-part of application No. 12/070,331, filed on Feb. 15, 2008, and a continuation-in-part of application No. 12/070,361, filed on Feb. 15, 2008, and a continuation-in-part of application No. 12/070,369, filed on Feb. 15, 2008, and a continuation-in-part of application No. 12/070,332, filed on Feb. 15, 2008, and a continuation-in-part of application No. 11/999,721, filed on Dec. 5, 2007.

(51) Int. Cl.
*A61N 1/18* (2006.01)
(52) U.S. Cl. .............................................. 607/2; 607/46
(58) Field of Classification Search ................ 607/2, 46, 607/117, 118
See application file for complete search history.

(56) References Cited

U.S. PATENT DOCUMENTS

| | | | |
|---|---|---|---|
| 3,841,306 A | 10/1974 | Hallgren | |
| 4,487,603 A | 12/1984 | Harris | |
| 4,570,640 A * | 2/1986 | Barsa | ............................ 600/554 |

(Continued)

FOREIGN PATENT DOCUMENTS
WO    WO 2009/073208 A1    6/2009
(Continued)

OTHER PUBLICATIONS
Singer, Emily; "Neural Stimulation for Autoimmune Diseases"; Technology Review; bearing a date of Jun. 1, 2010; pp. 1-2; MIT.
(Continued)

*Primary Examiner* — Brian T Gedeon

(57) ABSTRACT

Methods and related systems for modulating neural activity by repetitively blocking conduction in peripheral neural structures with chemical blocking agents are disclosed. Methods and systems for reversing effects of chemical blocking agents and/or for producing substantially permanent conduction block are also disclosed.

28 Claims, 29 Drawing Sheets

U.S. PATENT DOCUMENTS

| | | |
|---|---|---|
| 4,608,985 A | 9/1986 | Crish et al. |
| 4,719,919 A | 1/1988 | Marchosky et al. |
| 4,817,628 A | 4/1989 | Zealear et al. |
| 4,889,526 A | 12/1989 | Rauscher et al. |
| 4,939,149 A | 7/1990 | Blumberg |
| 5,031,618 A | 7/1991 | Mullett |
| 5,035,891 A | 7/1991 | Runkel et al. |
| 5,057,104 A | 10/1991 | Chess |
| 5,061,234 A | 10/1991 | Chaney |
| 5,092,835 A | 3/1992 | Schurig et al. |
| 5,188,104 A | 2/1993 | Wernicke et al. |
| 5,192,527 A | 3/1993 | Abrahmsohn |
| 5,215,089 A | 6/1993 | Baker, Jr. |
| 5,224,927 A | 7/1993 | Tapper |
| 5,224,928 A | 7/1993 | Sibalis et al. |
| 5,231,988 A | 8/1993 | Wernicke et al. |
| 5,251,634 A | 10/1993 | Weinberg |
| 5,330,515 A | 7/1994 | Rutecki et al. |
| 5,335,657 A | 8/1994 | Terry, Jr. et al. |
| 5,351,394 A | 10/1994 | Weinberg |
| 5,354,320 A | 10/1994 | Schaldach et al. |
| 5,395,398 A | 3/1995 | Rogozinski |
| 5,458,625 A | 10/1995 | Kendall |
| 5,499,967 A | 3/1996 | Teillaud et al. |
| 5,527,797 A | 6/1996 | Eisenberg et al. |
| 5,531,778 A | 7/1996 | Maschino et al. |
| 5,540,730 A | 7/1996 | Terry, Jr. et al. |
| 5,558,633 A | 9/1996 | Phipps et al. |
| 5,571,150 A | 11/1996 | Wernicke et al. |
| 5,628,769 A | 5/1997 | Saringer |
| 5,683,422 A | 11/1997 | Rise |
| 5,707,400 A | 1/1998 | Terry, Jr. et al. |
| 5,755,750 A | 5/1998 | Petruska et al. |
| 5,797,898 A | 8/1998 | Santini, Jr. et al. |
| 5,814,019 A | 9/1998 | Steinbach et al. |
| 5,817,139 A | 10/1998 | Kasano |
| 5,830,207 A | 11/1998 | Leeb et al. |
| 5,830,208 A | 11/1998 | Muller |
| 5,861,022 A | 1/1999 | Hipskind |
| 5,876,422 A | 3/1999 | Van Groeningen |
| 5,928,195 A | 7/1999 | Malamud et al. |
| 5,993,414 A | 11/1999 | Haller |
| 5,997,501 A | 12/1999 | Gross et al. |
| 6,012,457 A | 1/2000 | Lesh |
| 6,058,331 A | 5/2000 | King |
| 6,066,163 A | 5/2000 | John |
| 6,164,283 A | 12/2000 | Lesh |
| 6,185,455 B1 | 2/2001 | Loeb et al. |
| 6,208,894 B1 | 3/2001 | Schulman et al. |
| 6,238,421 B1 | 5/2001 | Günther et al. |
| 6,246,912 B1 | 6/2001 | Sluijter et al. |
| 6,248,126 B1 | 6/2001 | Lesser et al. |
| 6,314,325 B1 | 11/2001 | Fitz |
| 6,326,020 B1 | 12/2001 | Kohane et al. |
| 6,364,899 B1 | 4/2002 | Dobak, III |
| 6,405,732 B1 | 6/2002 | Edwards et al. |
| 6,416,495 B1 | 7/2002 | Kriesel et al. |
| 6,453,195 B1 | 9/2002 | Thompson |
| 6,454,759 B2 | 9/2002 | Krulevitch et al. |
| 6,464,687 B1 | 10/2002 | Ishikawa et al. |
| 6,527,695 B1 | 3/2003 | Davey et al. |
| 6,539,250 B1 | 3/2003 | Bettinger |
| 6,551,235 B2 | 4/2003 | Forsell |
| 6,554,822 B1 | 4/2003 | Holschneider et al. |
| 6,571,123 B2 | 5/2003 | Ives et al. |
| 6,571,125 B2 | 5/2003 | Thompson |
| 6,589,271 B1 | 7/2003 | Tzeng et al. |
| 6,600,956 B2 | 7/2003 | Maschino et al. |
| 6,622,048 B1 | 9/2003 | Mann et al. |
| 6,666,845 B2 | 12/2003 | Hooper et al. |
| 6,669,683 B2 | 12/2003 | Santini, Jr. et al. |
| 6,684,105 B2 | 1/2004 | Cohen et al. |
| 6,720,402 B2 | 4/2004 | Langer et al. |
| 6,745,078 B1 | 6/2004 | Buchner |
| 6,746,474 B2 | 6/2004 | Saadat |
| 6,755,621 B2 | 6/2004 | Lopez et al. |
| 6,761,715 B2 | 7/2004 | Carroll |
| 6,764,678 B2 | 7/2004 | Weber et al. |
| 6,770,022 B2 | 8/2004 | Mechlenburg et al. |
| 6,796,956 B2 | 9/2004 | Hartlaub et al. |
| 6,802,811 B1 | 10/2004 | Slepian |
| 6,808,522 B2 | 10/2004 | Richards et al. |
| 6,832,114 B1 | 12/2004 | Whitehurst et al. |
| 6,835,184 B1 | 12/2004 | Sage et al. |
| 6,860,852 B2 | 3/2005 | Schönenberger et al. |
| 6,871,092 B2 | 3/2005 | Piccone |
| 6,871,099 B1 | 3/2005 | Whitehurst et al. |
| 6,885,888 B2 | 4/2005 | Rezai |
| 6,921,413 B2 | 7/2005 | Mahadevan-Jansen et al. |
| 6,928,320 B2 | 8/2005 | King |
| 6,941,171 B2 | 9/2005 | Mann et al. |
| 6,976,982 B2 | 12/2005 | Santini, Jr. et al. |
| 6,978,174 B2 | 12/2005 | Gelfand et al. |
| 7,016,723 B2 | 3/2006 | Morris et al. |
| 7,031,768 B2 | 4/2006 | Anderson et al. |
| 7,033,571 B2 | 4/2006 | Gutowska et al. |
| 7,072,802 B2 | 7/2006 | Hartlaub |
| 7,076,307 B2 | 7/2006 | Boveja et al. |
| 7,108,680 B2 | 9/2006 | Rohr et al. |
| 7,113,821 B1 | 9/2006 | Sun et al. |
| 7,155,279 B2 | 12/2006 | Whitehurst et al. |
| 7,155,281 B1 | 12/2006 | Fayram |
| 7,162,303 B2 | 1/2007 | Levin et al. |
| 7,167,743 B2 | 1/2007 | Heruth et al. |
| 7,204,832 B2 | 4/2007 | Altshuler et al. |
| 7,204,833 B1 | 4/2007 | Osorio et al. |
| 7,209,787 B2 | 4/2007 | DiLorenzo |
| 7,209,788 B2 | 4/2007 | Nicolelis et al. |
| 7,226,426 B2 | 6/2007 | Thomson |
| 7,231,254 B2 | 6/2007 | DiLorenzo |
| 7,236,822 B2 | 6/2007 | Dobak, III |
| 7,242,983 B2 | 7/2007 | Frei et al. |
| 7,244,253 B2 | 7/2007 | Neev |
| 7,263,405 B2 | 8/2007 | Boveja et al. |
| 7,277,758 B2 | 10/2007 | DiLorenzo |
| 7,286,880 B2 | 10/2007 | Olson et al. |
| 7,315,761 B2 | 1/2008 | De Ridder |
| 7,319,899 B2 | 1/2008 | Keizer |
| 7,324,851 B1 | 1/2008 | DiLorenzo |
| 7,337,005 B2 * | 2/2008 | Kim et al. ............ 607/46 |
| 7,337,006 B2 | 2/2008 | Kim et al. |
| 7,340,304 B2 | 3/2008 | MacDonald |
| 7,389,145 B2 | 6/2008 | Kilgore et al. |
| 7,613,515 B2 | 11/2009 | Knudson et al. |
| 8,060,208 B2 | 11/2011 | Kilgore et al. |
| 2002/0019652 A1 | 2/2002 | Da Silva et al. |
| 2002/0058972 A1 | 5/2002 | Minogue et al. |
| 2002/0068964 A1 | 6/2002 | Dobak, III |
| 2002/0173827 A1 | 11/2002 | Jones et al. |
| 2003/0014097 A1 | 1/2003 | Putz et al. |
| 2003/0045914 A1 | 3/2003 | Cohen et al. |
| 2003/0050677 A1 | 3/2003 | Gross et al. |
| 2003/0060860 A1 | 3/2003 | Foster et al. |
| 2003/0097161 A1 | 5/2003 | Firlik et al. |
| 2003/0176901 A1 | 9/2003 | May |
| 2003/0219470 A1 | 11/2003 | Zhang et al. |
| 2004/0013716 A1 | 1/2004 | Gale et al. |
| 2004/0049134 A1 | 3/2004 | Tosaya et al. |
| 2004/0127886 A1 | 7/2004 | Daum |
| 2004/0127953 A1 | 7/2004 | Kilgore et al. |
| 2004/0172086 A1 | 9/2004 | Knudson et al. |
| 2004/0176812 A1 | 9/2004 | Knudson et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0070974 A1 | 3/2005 | Knudson et al. |
| 2005/0075669 A1 | 4/2005 | King |
| 2005/0075701 A1 | 4/2005 | Shafer |
| 2005/0075702 A1 | 4/2005 | Shafer |
| 2005/0076908 A1 | 4/2005 | Lee et al. |
| 2005/0080463 A1 | 4/2005 | Stahmann et al. |
| 2005/0119713 A1 | 6/2005 | Whitehurst et al. |
| 2005/0137648 A1 | 6/2005 | Cosendai et al. |
| 2005/0138934 A1 | 6/2005 | Weigert et al. |
| 2005/0149123 A1 | 7/2005 | Lesser et al. |
| 2005/0149148 A1 | 7/2005 | King |
| 2005/0203501 A1 | 9/2005 | Aldrich et al. |

| | | |
|---|---|---|
| 2005/0215947 A1 | 9/2005 | Heruth et al. |
| 2005/0216072 A1 | 9/2005 | Mahadevan-Jansen et al. |
| 2005/0234523 A1 | 10/2005 | Levin et al. |
| 2005/0277912 A1 | 12/2005 | John |
| 2005/0278001 A1 | 12/2005 | Qin et al. |
| 2005/0288730 A1 | 12/2005 | Deem et al. |
| 2006/0004417 A1 | 1/2006 | Rossing et al. |
| 2006/0036209 A1 | 2/2006 | Subramony et al. |
| 2006/0058694 A1 | 3/2006 | Clark et al. |
| 2006/0100668 A1 | 5/2006 | Ben-David et al. |
| 2006/0122454 A1 | 6/2006 | Riehl et al. |
| 2006/0122663 A1 | 6/2006 | Mandell |
| 2006/0122675 A1 | 6/2006 | Libbus et al. |
| 2006/0155348 A1 | 7/2006 | deCharms |
| 2006/0173493 A1 | 8/2006 | Armstrong et al. |
| 2006/0190053 A1 | 8/2006 | Dobak |
| 2006/0247721 A1 | 11/2006 | Maschino et al. |
| 2006/0247722 A1 | 11/2006 | Maschino et al. |
| 2006/0247739 A1 | 11/2006 | Wahlstrand et al. |
| 2006/0259077 A1 | 11/2006 | Pardo et al. |
| 2006/0270944 A1 | 11/2006 | King |
| 2006/0282134 A1 | 12/2006 | Shapiro et al. |
| 2006/0293721 A1 | 12/2006 | Tarver et al. |
| 2007/0027484 A1 | 2/2007 | Guzman et al. |
| 2007/0027496 A1 | 2/2007 | Parnis et al. |
| 2007/0027497 A1 | 2/2007 | Parnis |
| 2007/0055316 A1 | 3/2007 | Godara et al. |
| 2007/0060984 A1 | 3/2007 | Webb et al. |
| 2007/0093870 A1 | 4/2007 | Maschino |
| 2007/0129760 A1 | 6/2007 | Demarais et al. |
| 2007/0129774 A1 | 6/2007 | Bourget et al. |
| 2007/0135875 A1 | 6/2007 | Demarais et al. |
| 2007/0142875 A1 | 6/2007 | Shalev et al. |
| 2007/0150025 A1 | 6/2007 | Dilorenzo et al. |
| 2007/0150029 A1 | 6/2007 | Bourget et al. |
| 2007/0156032 A1 | 7/2007 | Gordon et al. |
| 2007/0156206 A1 | 7/2007 | Wahlstrand et al. |
| 2007/0167984 A1 | 7/2007 | Kieval et al. |
| 2007/0173899 A1 | 7/2007 | Levin et al. |
| 2007/0179557 A1 | 8/2007 | Maschino et al. |
| 2007/0191906 A1 | 8/2007 | Iyer et al. |
| 2007/0225781 A1 | 9/2007 | Saadat et al. |
| 2007/0255374 A1 | 11/2007 | Kolafa et al. |
| 2008/0045879 A1 | 2/2008 | Prausnitz et al. |
| 2008/0077198 A1 | 3/2008 | Webb et al. |
| 2008/0300657 A1 | 12/2008 | Stultz |

FOREIGN PATENT DOCUMENTS

| | | |
|---|---|---|
| WO | WO 2009/073223 A1 | 6/2009 |
| WO | WO 2009/075783 A1 | 6/2009 |

OTHER PUBLICATIONS

PCT International Search Report; International App. No. PCT/US 08/13443; Feb. 20, 2009; pp. 1-2.

PCT International Search Report; International App. No. PCT/US 08/13442; Feb. 20, 2009; pp. 1-3.

PCT International Search Report; International App. No. PCT/US 08/13407; Feb. 20, 2009; pp. 1-2.

PCT International Search Report; International App. No. PCT/US2008/013406; Feb. 9, 2009; pp. 1-2.

"Application Note- Rat Sciatic Nerve"; Aculight Corporation; bearing a date of Dec. 6, 2006; pp. 1-2.

Belverud, Shawn; Mogilner, Alon; Schulder, Michael; "Intrathecal Pumps"; Neurotherapeutics: The Journal of the American Society for Experimental NeuroTherapeutics; Jan. 2008; pp. 114-122; vol. 5, No. 1.

Binshtok, Alexander M.; Bean, Bruce P.; Woolf, Clifford J.; "Inhibition of Nociceptors by TRPV1-Mediated Entry of Impermeant Sodium Channel Blockers"; Nature, Letters; bearing a date of Oct. 4, 2007; pp. 607-611; vol. 449; Nature Publishing Group.

Bjordal, Jan M.; Johnson, Mark I.; Lopes-Martins, Rodrigo AB; Bogen, Bard; Chow, Roberta; Ljunggren, Anne E.; "Short-Term Efficacy of Physical Interventions in Osteoarthritic Knee Pain. A Systematic Review and Meta-Analysis of Randomised Placebo-Controlled Trials."; BMC Musculoskeletal Disorders, BioMed Central; 2007; pp. 1-34, plus cover page and Figs.1-8; vol. 8, No. 51; BioMed Central Ltd.; located at: http://www.biomedcentral.com/1471-2474/8/51.

Boggs, Will; "Physical Interventions can be Effective for Osteoarthritic Knee Pain"; WebMD; 1994-2007; pp. 1-2; Medscape; located at: http://www.medscape.com/viewarticle/559501; printed on Jul. 12, 2007.

Bostock, Hugh; Cikurel, Katia; Burke, David; "Invited Review: Threshold Tracking Techniques in the Study of Human Peripheral Nerve"; Muscle & Nerve; Feb. 1998; pp. 137-158; John Wiley & Sons, Inc.

Brooks, Jonathan; Tracey, Irene; "Review: From Nociception to Pain Perception: Imaging the Spinal and Supraspinal Pathways"; Journal of Anatomy; 2005; pp. 19-33; vol. 207; Anatomical Society of Great Britain and Ireland.

Burdakov, Denis; Gerasimenko, Oleg; Verkhratsky, Alexei; "Brief Communication: Physiological Changes in Glucose Differentially Modulate the Excitability of Hypothalamic Melanin-Concentrating Hormone and Orexin Neurons In Situ"; The Journal of Neuroscience; bearing a date of Mar. 2, 2005; pp. 2429-2433; vol. 25, No. 9.

"Could Nerve-Snip Spur Weight Loss?"; CNN.com; 2007; pp. 1-2; Cable News Network; located at: http://www.cnn.com/2007/HEALTH/conditions/07/09/obesity.nerve.ap/index.html; printed on Jul. 12, 2007.

Douglas, W.W.; Malcom, J.L.; "The Effect of Localized Cooling on Conduction in Cat Nerves"; Journal of Physiology; 1955; pp. 53-71; vol. 130; located at: jp.physoc.org.

Fang, Zi-Ping; Mortimer, J. Thomas; "Selective Activation of Small Motor Axons by Quasitrapezoidal Current Pulses"; IEEE Transactions on Biomedical Engineering; Feb. 1991; pp. 168-174; vol. 38, No. 2; IEEE.

Franz, D.N.; Iggo, A.; "Conduction Failure in Myelinated and Non-Myelinated Axons at Low Temperatures"; Journal of Physiology; 1968; pp. 319-345; vol. 199.

Gordon, Ryan D.; Peterson, Tim A.; "4 Myths About Transdermal Drug Delivery"; Drug Delivery Technology; bearing a date of Jun. 4, 2003 and posted on Mar. 28, 2008; pp. 1-9; vol. 3, No. 4.

Grayson, Amy C. Richards; Shawgo, Rebecca S.; Johnson, Audrey M.; Flynn, Nolan T.; Li, Yawen; Cima, Michael J.; Langer, Robert; "A BioMEMS Review: MEMS Technology for Physiologically Integrated Devices"; Proceedings of the IEEE; bearing a date of Jan. 2004; pp. 6-21; vol. 92, No. 1.

Han, Xue; Boyden, Edward S.; "Multiple-Color Optical Activation, Silencing, and Desynchronization of Neural Activity, with Single-Spike Temporal Resolution"; PLoS One; Mar. 2007; pp. 1-12; Issue 3, No. e299; located at: www.plosone.org.

Harland, C.J.; Clark, T.D.; Prance, R.J.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.

Hinrikus, H.; Lass, J.; Tuulik, V.; "Low-Level Microwave Effect on Nerve Pulse Propagation Velocity"; Proceedings of the 25th Annual International Conference of the IEEE EMBS; bearing dates of Sep. 17, 2003-Sep. 21, 2003; pp. 3253-3256; IEEE.

Hodgkin, A.L.; Huxley, A.F.; "A Quantitative Description of Membrane Current and its Application to Conduction and Excitation in Nerve"; Journal of Physiology; 1952; pp. 500-544; vol. 117.

Hong, CZ; "Reversible Nerve Conduction Block in Patients with Polyneuropathy After Ultrasound Thermotherapy at Therapeutic Dosage."; Archives of Physical Medicine and Rehabilitation; Feb. 1991; pp. 132-137, only the abstract is being provided; vol. 72, No. 2; located at: http://www.ncbi.nlm.nih.gov/sites/entrez?cmd=Retrieve&db=PubMed&list_uids=1846738&dopt=AbstractPlus; printed on May 9, 2007.

Howarth, Peter H.; Persson, Carl G.A.; Meltzer, Eli O.; Jacobson, Mikila R.; Durham, Stephen R.; Silkoff, Philip E.; "Objective Monitoring of Nasal Airway Inflammation in Rhinitis"; Journal of Allergy Clin Immunol; Mar. 2005; pp. S414-S441; American Academy of Allergy, Asthma and Immunology.

Hsieh, Dean S. T.; Langer Robert; Folkman, Judah; "Magnetic Modulation of Release of Macromolecules from Polymers"; Proc. Natl. Acad. Sci. USA; bearing a date of Mar. 1981; pp. 1863-1867; vol. 78. No. 3.

Hsu, Kai-Hsiung; Durand, Dominique M.; "A 3-D Differential Coil Design for Localized Magnetic Stimulation"; IEEE Transactions on Biomedical Engineering; Oct. 2001; pp. 1162-1168; vol. 48, No. 10; IEEE.

Hsu, Kai-Hsiung; Durand, Dominique M.; "Prediction of Neural Excitation During Magnetic Stimulation Using Passive Cable Models"; IEEE Transactions on Biomedical Engineering; Apr. 2000; pp. 463-471; vol. 47, No. 4; IEEE.

Hsu, Kai-Hsiung; Nagarajan, Srikantan S.; Durand, Dominique M.; "Analysis of Efficiency of Magnetic Stimulation"; IEEE Transactions on Biomedical Engineering; Nov. 2003; pp. 1276-1285; vol. 50, No. 11; IEEE.

Kane, D.; Lockhart, JC; Balint, PV; Mann, C.; Ferrell, WR; McInnes, IB; "Protective Effect of Sensory Denervation in Inflammatory Arthritis (evidence of regulatory neuroimmune pathways in the arthritic joint)"; ARD Online, Ann. Rheum. Dis.; 2005; pp. 325-327 plus cover page; vol. 64; located at: www.annrheumdis.com.

Kilani, Ruhangiz T.; Maksymowych, Walter P.; Aitken, Alastair; Boire, Gilles; St. Pierre, Yves; Li, Yunyuan; Ghahary, Aziz; "Detection of High Levels of 2 Specific Isoforms of 14-3-3 Proteins in Synovial Fluid from Patients with Joint Inflammation"; The Journal of Rheumatology; 2007; pp. 1650-1657; vol. 34, No. 8.

Kilgore, K.L.; Bhadra, N.; "Nerve Conduction Block Utilising High-Frequency Alternating Current"; Medical & Biological Engineering & Computing; 2004; pp. 394-406; vol. 42; IFMBE.

Krasteva, Vessela TZ; Papazov, Sava P.; Daskalov, Ivan K.; "Peripheral Nerve Magnetic Stimulation: Influence of Tissue Non-Homogeneity"; BioMedical Engineering online; 2003; pp. 1-14; located at: http://www.biomedical-engineering-online.com/content/2/1/19.

Krauthamer, V.; Crosheck, T.; "Effects of High-Rate Electrical Stimulation Upon Firing in Modelled and Real Neurons"; Medical & Biological Engineering & Computing; 2002; pp. 360-366; vol. 40; IFMBE.

Kuwabara, Satoshi; Cappelen-Smith, Cecilia; Lin, Cindy S.-Y.; Mogyoros, Ilona; Bostock, Hugh; Burke, David; "Excitability Properties of Median and Peroneal Motor Axons"; Muscle and Nerve; Sep. 2000; pp. 1365-1373; vol. 23.

Lam, Fy; Ferrell, WR; "Neurogenic Component of Different Models of Acute Inflammation in the Rat Knee Joint."; PubMed, NCBI, Ann. Rheum. Dis.; Nov. 1991; pp. 747-751, only the abstract is enclosed; vol. 50, No. 11; printed on May 17, 2007.

Lele, P.P.; "Effects of Focused Ultrasonic Radiation on Peripheral Nerve, with Observations on Local Heating"; Experimental Neurology; 1963; pp. 47-83; vol. 8.

Lin, Cindy S.-Y.; Mogyoros, Ilona; Kuwabara, Satoshi; Cappelen-Smith, Cecilia; Burke, David; "Accommodation to Depolarizing and Hyperpolarizing Currents in Cutaneous Afferents of the Human Median and Sural Nerves"; The Journal of Physiology Online; *J. Physiol.* 2000; pp. 483-492; vol. 529; located at: http://www.jp.physoc.org/cgi/content/full/529/2/483 ; printed on Oct. 5, 2007.

"Local Anaesthetics and Nerve Conduction"; The Virtual Anaesthesia Textbook; pp. 1-2; located at: http://www.virtual-anaesthesia-textbook.com.

Ma, Qing-Ping; "Vanilloid Receptor Homologue, VRLI, is Expressed by Both A- and C- Fiber Sensory Neurons" NeuroReport, Somatosensory Systems, Pain; bearing a date of Dec. 4, 2001; pp. 3693-3695; vol. 12, No. 17; Lippincott Williams & Wilkins.

"Makers of ActiPatch™ a Drug-Free, Anti-Inflammatory Patch that Resolves Swellin"; BioElectronics; 2004; pp. 1-4; BioElectronics Corp.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

McCleskey, Edwin W.; "Neuroscience: A Local Route to Pain Relief"; Nature-News & Views; bearing a date of Oct. 4, 2007; pp. 545-546; vol. 449; Nature Publishing Group.

McNeal, Donald R.; "Analysis of a Model for Excitation of Myelinated Nerve"; IEEE Transactions on Biomedical Engineering; Jul. 1976; pp. 329-337; vol. BME-23, No. 4.

Norton, Stephen J.; "Research: Can Ultrasound be Used to Stimulate Nerve Tissue?"; BioMedical Engineering OnLine; 2003; pp. 1-9; vol. 2, No. 6; BioMed Central Ltd.; located at: http://www.biomedical-engineering-online.com/content/2/1/6.

Orlee, Kenneth S., Horch, Kenneth W.; "Differential Activiation and Block of Peripheral Nerve Fibers by Magnetic Fields"; Muscle and Nerve; 2006; pp. 189-196; vol. 34; located at: www.interscience.wiley.com.

Pareek, Tej K.; Keller, Jason; Kesavapany, Sashi; Pant, Harish C.; Ladarola, Michael J.; Brady, Roscoe O.; Kulkarni, Ashok B.; "Cyclin-Dependent Kinase 5 Activity Regulates Pain Signaling"; PNAS; bearing a date of Jan. 17, 2006; pp. 791-796; vol. 103, No. 3.

Pavlov, V.A.; Tracey, K.J.; "Review: Neural Regulators of Innate Immune Responses and Inflammation"; CMLS-Cellular and Molecular Life Sciences; 2004; pp. 2322-2331; vol. 61; Birkhäuser Verlag, Basel.

Peckham, P. Hunter; Knutson, Jayme S.; "Functional Electrical Stimulation for Neuromuscular Applications"; Annual Reviews; 2005; pp. 327-360; located at: http://www.arjournals.annualreviews.org ; printed on Feb. 13, 2007.

Pham-Marcou, T.A.; Gentili, M.; Asehnoune, K.; Fletcher, D.; Mazoit, J.-X.; "Pain: Effect of Neurolytic Nerve Block on Systemic Carrageenan-Induced Inflammatory Response in Mice"; British Journal of Anaesthesia; 2005; pp. 243-246; vol. 95, No. 2; The Board of Management and Trustees of the British Journal of Anaesthesia.

Poole, A R; "Immunochemical Markers of Joint Inflammation, Skeletal Damage and Repair: Where are we now?"; Annals of the Rheumatic Diseases; 1994; pp. 3-5; vol. 53.

Power, I.; "Review Article: Fentanyl HCl Iontophoretic Transdermal System (ITS): Clinical Application of Iontophoretic Technology in the Management of Acute Postoperative Pain"; British Journal of Anaesthesia; bearing a date of 2007; pp. 4-11; vol. 98, No. 1.

Prescott, James H.; Lipka, Sara; Baldwin, Samuel; Sheppard, Jr., Norman F.; Maloney, John M.; Coppeta, Jonathan; Yomtov, Barry; Staples, Mark A.; Santini, Jr., John T.; "Brief Communications: Chronic, Programmed Polypeptide Delivery from an Implanted, Multireservoir Microchip Device"; Nature Biotechnology; bearing a date of Apr. 2006; pp. 437-438; vol. 24, No. 4; located at: www.nature.com/naturebiotechnology.

"Product Information: Actipatch"; BioElectronics, Medical Professionals Info Center; 2004; pp. 1-3; BioElectronics Corp.

Rattay, Frank; "Analysis of Models for Extracellular Fiber Stimulation"; IEEE Transactions on Biomedical Engineering; Jul. 1989; pp. 676-682; vol. 36, No. 7; IEEE.

Rattay, Frank; "Modeling the Excitation of Fibers Under Surface Electrodes"; IEEE Transactions on Biomedical Engineering; Mar. 1988; pp. 199-202; vol. 35, No. 3; IEEE.

Rattay, Frank, Aberham, Matthias; "Modeling Axon Membranes from Functional Electrical Stimulation"; IEEE Transactions on Biomedical Engineering; Dec. 1993; pp. 1201-1209; vol. 40, No. 12; IEEE.

Razavi, Rozita; Chan, Yin; Afifiyan, F. Nikoo; Liu, Xue Jun; Wan, Xiang; Yantha, Jason; Tsui, Hubert; Tang, Lan; Tsai, Sue; Santamaria, Pere; Driver, John P.; Serreze, David; Salter, Michael W.; Dosch, H.-Michael; "TRPV1+ Sensory Neurons Control β Cell Stress and Islet Inflammation in Autoimmune Diabetes"; Cell; bearing a date of Dec. 15, 2006; pp. 1123-1135; vol. 127; Elsevier Inc.

"Robot Anaesthetist Developed in France: Doctor"; Yahoo!; Agence France Press; bearing a date of Apr. 12, 2008; pp. 1-2.

Rooney, Terence; Bresnihan, Barry; Andersson, Ulf; Gogarty, Martina; Kraan, Maarten; Schumacher, H. Ralph; Ulfgren, Ann-Kristin; Veale, Douglas J.; Youssef, Peter P.; Tak, Paul P.; "Microscopic Measurement of Inflammation in Synovial Tissue: Inter-Observer Agreement for Manual Quantitative, Semiquantitative and Computerised Digital Image Analysis"; Ann Rheum Dis; 2007; pp. 1656-1660; vol. 66.

Roxhed, Niclas; Samel, Bjorn; Nordquist, Lina; Griss, Patrick; Stemme, Goran; "Painless Drug Delivery Through Microneedle-Based Transdermal Patches Featuring Active Infusion"; IEEE Transactions on Biomedical Engineering; bearing a date of Mar. 2008; pp. 1063-1071; vol. 55, No. 3.

Saliba, Susan; Mistry, Dilaawar J.; Perrin, David H.; Gieck, Joe; Weltman, Arthur; "Original Research: Phonophoresis and the Absorption of Dexamethasone in the Presence of an Occlusive Deressing"; Journal of Athletic Training; 2007; pp. 349-354; National Athletic Trainers' Association, Inc; located at: www.journalofathletictraining.org.

Singer, Emily; "A New Way to Treat Obesity"; Technology Review; bearing a date of May 15, 2008; pp. 1-3; MIT.

Sternberg, Esther M.; "Neural Regulation of Innate Immunity: A Coordinated Nonspecific Host Response to Pathogens"; NIH Public Access, Author Manuscript-Nat. Rev. Immunol.; Apr. 2006; pp. 318-328 (pp. 1-26); vol. 6, No. 4.

Stubbe, Barbara G.; De Smedt, Stefaan C.; Demeester, Joseph; "Review "Programmed Polymeric Devices" for Pulsed Drug Delivery"; Pharmaceutical Research; bearing a date of Oct. 2004; pp. 1732-1740; vol. 21, No. 10.

"Study Finds Nerve Damage in Previously Mysterious Chronic Pain Syndrome"; Doctor's Guide, Personal Edition; 2007; pp. 1-2 (front and back); located at: http://www.docguide.com/news/content.nsf/NewsPrint/852571020057CCF685257107005273F6; printed on May 9, 2007.

Struijk, Johannes Jan; "The Extracellular Potential of a Myelinated Nerve Fiber in an Unbounded Medium and in Nerve Cuff Models"; Biophysical Journal; Jun. 1997; pp. 2457-2469; vol. 72; Biophysical Society.

Tai, Changfeng; De Groat, William C.; Roppolo, James R.; "Simulation Analysis of Conduction Block in Unmyelinated Axons Induced by High-Frequency Biphasic Electrical Currents"; IEEE Transactions on Biomedical Engineering; Jul. 2005; pp. 1323-1332; vol. 52, No. 7.

Tokushige, Natsuko; Markham, Robert; Russell, Peter; Fraser, Ian S.; "Nerve Fibers in Peritoneal Endometriosis"; Human Reproduction; 2006; pp. 3001-3007; vol. 21, No. 11.

Tracey, Kevin J.; "Review: Physiology and Immunology of the Cholinergic Antiinflammatory Pathway"; The Journal of Clinical Investigation; Feb. 2007; pp. 289-296; vol. 117, No. 2; located at: http://www.jci.org.

"Treatment Blocks Pain Without Disrupting Other Functions"; published: Oct. 3, 2007; 2 pages; located at: http://www.physorg.com/news110637008.html.

Tsui, Po-Hsiang; Wang, Shyh-Hau; Huang, Chih-Chung; "In Vitro Effects of Ultrasound with Different Energies on the Conduction Properties of Neural Tissue"; ScienceDirect-Ultrasonics; 2005; pp. 560-565; vol. 43; Elsevier B.V.; located at: www.elsevier.com/locate/ultras.

Van Den Honert, Christopher; Mortimer, J. Thomas; "A Technique for Collision Block of Peripheral Nerve: Single Stimulus Analysis"; IEEE Transactions on Biomedical Engineering; May 1981; pp. 373-378; vol. BME-28, No. 5.

Voloshin, Ilya; Gelinas, Jill; Maloney, Michael D.; O'Keefe, Regis J.; Bigliani, Louis U.; Blaine, Theodore A.; "Proinflammatory Cytokines and Metalloproteases are Expressed in the Subacromial Bursa in Patients with Rotator Cuff Disease"; The Journal of Arthroscopic and Related Surgery; 2005; pp. 1076e1-1076e9; vol. 21, No. 9.

Walsh, Raymond R.; Deal, Stanley E.; "Reversible Conduction Block Produced by Lipid-Insoluble Quarternary Ammonium Ions in Cetyltrimethylammonium Bromide-Treated Nerves"; Am J Physiol; 1959; pp. 547-550; Only the abstract is being provided; vol. 197; located at: http://ajplegacy.physiology.org.

Wells, Jonathan; Kao, Chris; Konrad, Peter; Milner, Tom; Kim, Jihoon; Mahadevan-Jansen, Anita; Jansen, E. Duco; "Application of Infared Light for In Vivo Neural Stimulation"; The Journal of Biomedical Optics; Nov./Dec. 2005; pp. 064003-1-064003-12; vol. 10(6).

Wells, Jonathan; Kao, Chris; Konrad, Peter; Milner, Tom; Kim, Jihoon; Mahadevan-Jansen, Anita; Jansen, E. Duco; "Biophysical Mechanisms of Transient Optical Stimulation of Peripheral Nerve"; Biophysical Journal; Oct. 2007; pp. 2567-2580; vol. 93.

Wells, Jonathan; Konrad, Peter; Kao, Chris; Jansen, E. Duco; Mahadevan-Jansen, Anita; "Pulsed Laser Versus Electrical Energy for Peripheral Nerve Stimulation"; Journal of Neuroscience Methods; 2007; pp. 326-337; located at: www.elsevier.com/locate/jneumeth.

Windle, Mary L.; "Anesthesia, Topical"; E-Medicine from WebMD; Mar. 14, 2007; pp. 1-4; located at: www.webmd.com.

Zhang, Xu; Roppolo, James R.; De Groat, William C.; Tai, Changfeng; "Mechanism of Nerve Conduction Block Induced by High-Frequency Biphasic Electrical Currents"; IEEE Transactions on Biomedical Engineering; Dec. 2006; pp. 2445-2454; vol. 53, No. 12.

Zhang, Xu; Roppolo, James R.; De Groat, William C.; Tai, Changfeng; "Simulation Analysis of Conduction Block in Myelinated Axons Induced by High-Frequency Biphasic Rectangular Pulses"; IEEE Transactions on Biomedical Engineering; Jul. 2006; pp. 1433-1436; ; vol. 53, No. 7.

"Device blocking stomach nerve signals shows promise in obesity", Physorg.com, Mayo Clinic, bearing a date of Jun. 26, 2008, pp. 1-2; located at http://www.physorg.com/news133701913.html.

U.S. Appl. No. 12/214,758, filed Jun. 18, 2008, Dacey, Jr. et al.
U.S. Appl. No. 12/214,559, filed Jun. 18, 2008, Dacey, Jr. et al.
U.S. Appl. No. 12/214,558, filed Jun. 18, 2008, Dacey, Jr. et al.
U.S. Appl. No. 12/214,557, filed Jun. 18, 2008, Dacey, Jr. et al.
U.S. Appl. No. 12/214,545, filed Jun. 18, 2008, Dacey, Jr. et al.
UK Intellectual Property Office Examination Report under Section 18(3); Application No. GB1010163.2; Jan. 26, 2012; pp. 1-2.

* cited by examiner

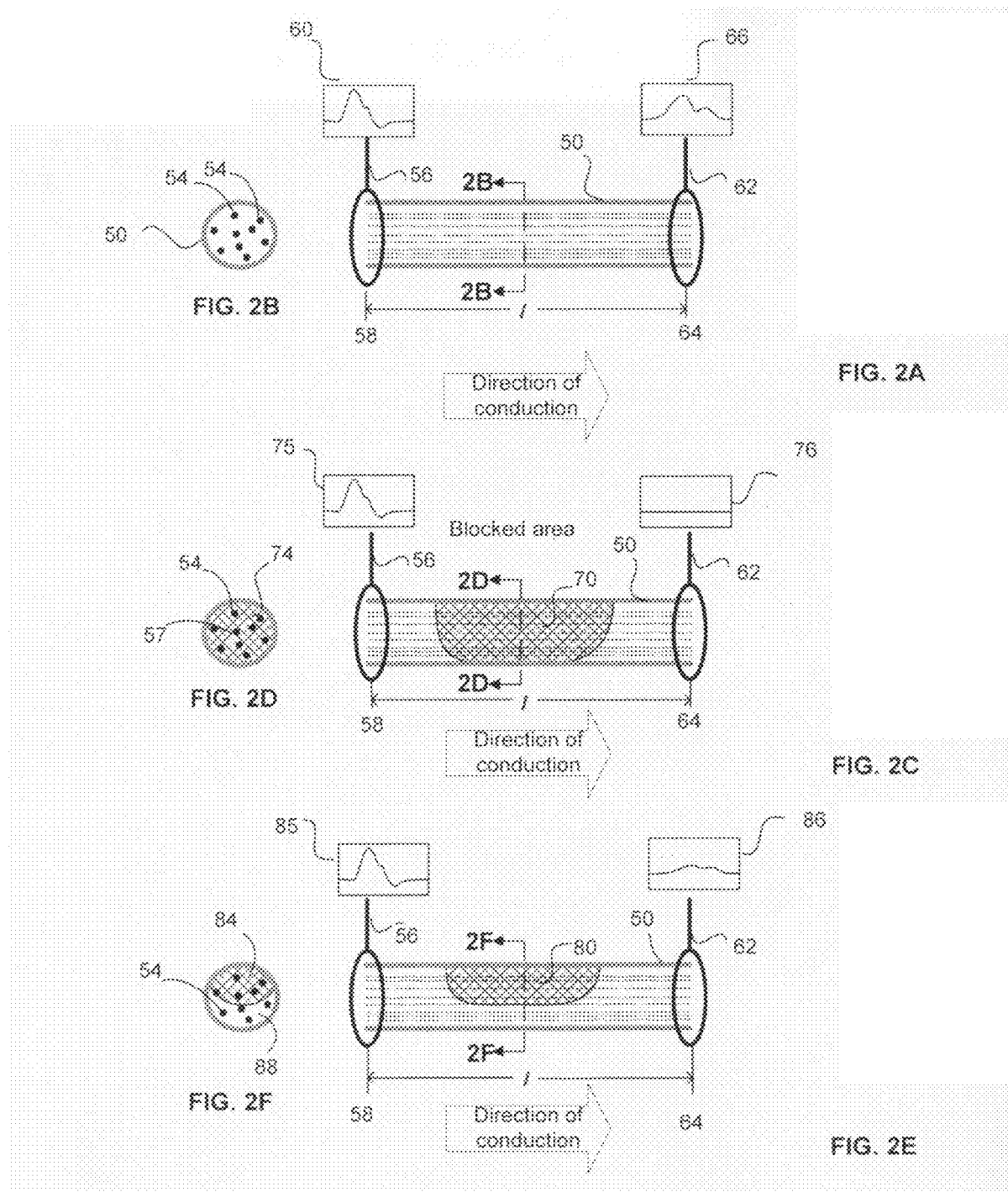

SYSTEM FOR CHEMICAL MODULATION OF NEURAL ACTIVITY

CROSS-REFERENCE TO RELATED APPLICATIONS

The present application is related to and claims the benefit of the earliest available effective filing date(s) from the following listed application(s) (the "Related Applications") (e.g., claims earliest available priority dates for other then provisional patent application or claims benefits under 35 USC §119(e) for provisional patent application, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 11/999,721, titled "METHOD AND SYSTEM FOR CYCLICAL NEURAL MODULATION BASED ON ACTIVITY STATE", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 5 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/070,332, titled "METHOD FOR MAGNETIC MODULATION OF NEURAL CONDUCTION", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 15 Feb. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/070,369, titled "SYSTEM FOR MAGNETIC MODULATION OF NEURAL CONDUCTION", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 15 Feb. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/070,361, titled "METHOD FOR ELECTRICAL MODULATION OF NEURAL CONDUCTION", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 15 Feb. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/070,331, titled "SYSTEM FOR ELECTRICAL MODULATION OF NEURAL CONDUCTION", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 15 Feb. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/080,787, titled "METHOD FOR THERMAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 4 Apr. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/080,789, titled "SYSTEM FOR THERMAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y. H. WOOD, AND GREGORY J. ZIPFEL as inventors, filed 4 Apr. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/214 559, titled "METHOD FOR CHEMICAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y.H. WOOD, AND GREGORY J. ZIPFEL as inventors, filed substantially contemporaneously herewith, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/214 758, titled "METHOD FOR REVERSIBLE CHEMICAL MODULATION OF NEURAL ACTIVITY", naming RALPH G. DACEY, JR., GREGORY J. DELLA ROCCA, COLIN P.

DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y.H. WOOD, AND GREGORY J. ZIPFEL as inventors, filed substantially contemporaneously herewith, which is currently co-pending, or is an application of which a currently co-pending application is entitled to the benefit of the filing date.

For purposes of the USPTO extra-statutory requirements, the present application constitutes a continuation-in-part of U. S. patent application Ser. No. 12/214 557, titled "SYSTEM FOR TRANSDERMAL CHEMICAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y.H. WOOD, AND GREGORY J. ZIPFEL as inventors, filed substantially contemporaneously herewith, which is currently co-pending, or is an application of which a currently co-pending application is entitled to the benefit of the filing date.

For purposes of the USPTO extra-statutory requirements, the present application constitutes a continuation-in-part of U. S. patent application Ser. No. 12/214 558, titled "IMPLANT SYSTEM FOR CHEMICAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y.H. WOOD, AND GREGORY J. ZIPFEL as inventors, filed substantially contemporaneously herewith, which is currently co-pending, or is an application of which a currently co-pending application is entitled to the benefit of the filing date.

For purposes of the USPTO extra-statutory requirements, the present application constitutes a continuation-in-part of U. S. patent application Ser. No. 12/214 545, titled "SYSTEM FOR REVERSIBLE CHEMICAL MODULATION OF NEURAL ACTIVITY", naming RALPH G. DACEY, JR., GREGORY J. DELLA ROCCA, COLIN P. DERDEYN, JOSHUA L. DOWLING, ELEANOR V. GOODALL, RODERICK A. HYDE, MURIEL Y. ISHIKAWA, JORDIN T. KARE, ERIC C. LEUTHARDT, NATHAN P. MYHRVOLD, MICHAEL A. SMITH, LOWELL L. WOOD, JR., VICTORIA Y.H. WOOD, AND GREGORY J. ZIPFEL as inventors, filed substantially contemporaneously herewith, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a method of modulating neural activity may include producing a reversible conduction block in a peripheral neural structure of a subject with a chemical blocking agent while the subject is in a first activity state, reversing the reversible conduction block in the peripheral neural structure of the subject to permit conduction in the peripheral neural structure when the subject is in a second activity state, and repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state.

In another aspect, a method of modulating neural activity may include producing a reversible conduction block in a peripheral neural structure of a subject with a chemical blocking agent while the subject is in a first activity state, reversing the reversible conduction block in the peripheral neural structure of the subject to permit conduction in the peripheral neural structure when the subject is in a second activity state by applying a reversing stimulus configured to counter the chemical blocking agent used to produce the reversible conduction block in the peripheral neural structure of the subject, and repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state.

In another aspect, a method of modulating neural activity may include producing a reversible conduction block in a peripheral neural structure of a subject with a chemical blocking agent while the subject is in a first activity state, reversing the reversible conduction block in the peripheral neural structure of the subject to permit conduction in the peripheral neural structure when the subject is in a second activity state, repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state, determining that producing the reversible conduction block in the peripheral neural structure of the subject while the subject is in a first activity state results in a desired effect in the subject, and producing a non-reversible conduction block in the peripheral neural structure of the subject.

In still another aspect, a method of modulating neural activity may include producing a reversible conduction block of a subset of nerve fibers in a peripheral neural structure of a subject with a chemical blocking agent while the subject is in a first activity state, reversing the reversible conduction block of the subset of nerve fibers in the peripheral neural structure of the subject to permit conduction in the subset of nerve fibers in the peripheral neural structure when the subject is in a second activity state, and repeating the steps of producing a reversible conduction block in the subset of nerve fibers in a peripheral neural structure of a subject while the subject is in a first activity state and reversing the reversible conduction block in the subset of nerve fibers in the peripheral neural structure of the subject to permit conduction in the subset of nerve fibers in the peripheral neural structure when the subject is in a second activity state.

In addition to the foregoing, other method aspects are as described in the claims, drawings, and text forming a part of the present disclosure.

In one aspect, a neural modulation system may include a signal input structure configured to receive a signal indicative of an activity state of at least a portion of a body of a subject innervated by a peripheral neural structure, a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure and generate a chemical blocking agent control signal for driving delivery of a chemical blocking agent adapted to reversibly block conduction in the peripheral neural structure of the subject during at least a portion of the first activity state, and a chemical blocking agent source configured to deliver a chemical blocking agent responsive to the chemical blocking agent control signal.

In another aspect, a neural modulation system may include a signal input structure configured to receive a signal indicative of an activity state of at least a portion of a body of a subject innervated by a peripheral neural structure, a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure and generate a chemical blocking agent control signal for driving delivery of a chemical blocking agent adapted to reversibly block conduction in the peripheral neural structure of the subject during at least a portion of the first activity state, and a chemical blocking agent source configured to be worn on the body of the subject and to deliver a chemical blocking agent responsive to the chemical blocking agent control signal.

In another aspect, a neural modulation system may include a signal input structure configured to receive a signal indicative of an activity state of at least a portion of a body of a subject innervated by a peripheral neural structure, a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure and generate a chemical blocking agent control signal for driving delivery of a chemical blocking agent adapted to reversibly block conduction in the peripheral neural structure of the subject during at least a portion of the first activity state, and a chemical blocking agent source configured to be positioned beneath at least a portion of the body of the subject and to deliver a chemical blocking agent responsive to the chemical blocking agent control signal.

In yet another aspect, a neural modulation system may include a signal input structure configured to receive a signal indicative of an activity state of at least a portion of a body of a subject innervated by a peripheral neural structure, a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure and generate a chemical blocking agent control signal for driving delivery of a chemical blocking agent adapted to reversibly block conduction in the peripheral neural structure of the subject during at least a portion of the first activity state, and a chemical blocking agent source configured to be implanted within the body of the subject and to deliver a chemical blocking agent responsive to the chemical blocking agent control signal.

In still another aspect, a neural modulation system may include a signal input structure configured to receive a signal indicative of an activity state of at least a portion of a body of a subject innervated by a peripheral neural structure; a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure, generate a chemical blocking agent control signal for driving delivery of a chemical blocking agent adapted to reversibly block conduction in the peripheral neural structure of the subject during at least a portion of the first activity state, and generate a reversing stimulus control signal for driving delivery of a reversing stimulus to counter the chemical blocking agent used to produce the reversible conduction block in the peripheral neural structure of the subject; a chemical blocking agent source configured to deliver a chemical blocking agent responsive to the chemical blocking agent control signal; and a reversing stimulus source configured to produce a reversing stimulus responsive to the reversing stimulus control signal.

In a further aspect, a neural modulation system may include a signal input structure configured to receive a signal indicative of an activity state of at least a portion of a body of a subject innervated by a peripheral neural structure; a signal processing portion configured to distinguish a first activity state of the at least a portion of the body of the subject innervated by the peripheral neural structure from a second activity state of the at least a portion of the body of the subject innervated by the peripheral neural structure from the signal received at the signal input structure, generate a chemical blocking agent control signal for driving delivery of a chemical blocking agent adapted to reversibly block conduction in the peripheral neural structure of the subject during at least a portion of the first activity state, determine that producing the reversible conduction block in the peripheral neural structure of the subject while the subject is in a first activity state results in a desired effect in the subject, and generate a non-reversible blocking source control signal for driving a non-reversible blocking source to perform an action adapted for producing a non-reversible conduction block in the peripheral neural structure of the subject; a chemical blocking agent source configured to deliver a chemical blocking agent responsive to the chemical blocking agent control signal; and a non-reversible blocking source configured to perform an action adapted for producing a non-reversible conduction block in the peripheral neural structure of the subject responsive to the non-reversible blocking source control signal.

In addition to the foregoing, other system aspects are described in the claims, drawings, and text forming a part of the present disclosure.

In one or more various aspects, related systems include but are not limited to circuitry and/or programming, including instructions carried on signal bearing media, for effecting the herein-referenced method aspects.

The foregoing is a summary and thus may contain simplifications, generalizations, inclusions, and/or omissions of detail; consequently, those skilled in the art will appreciate that the summary is illustrative only and is NOT intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2A is an illustration of conduction in nerve;

FIG. 2B is a cross-sectional view of the nerve depicted in FIG. 2A;

FIG. 2C is an illustration of the effect of a complete conduction block in the nerve depicted in FIG. 2A;

FIG. 2D is a cross-sectional view of the nerve depicted in FIG. 2C;

FIG. 2E is an illustration of the effect of a partial conduction block in the nerve depicted in FIG. 2A;

FIG. 2F is a cross-sectional view of the nerve depicted in FIG. 2E;

DETAILED DESCRIPTION

Figure 1A:
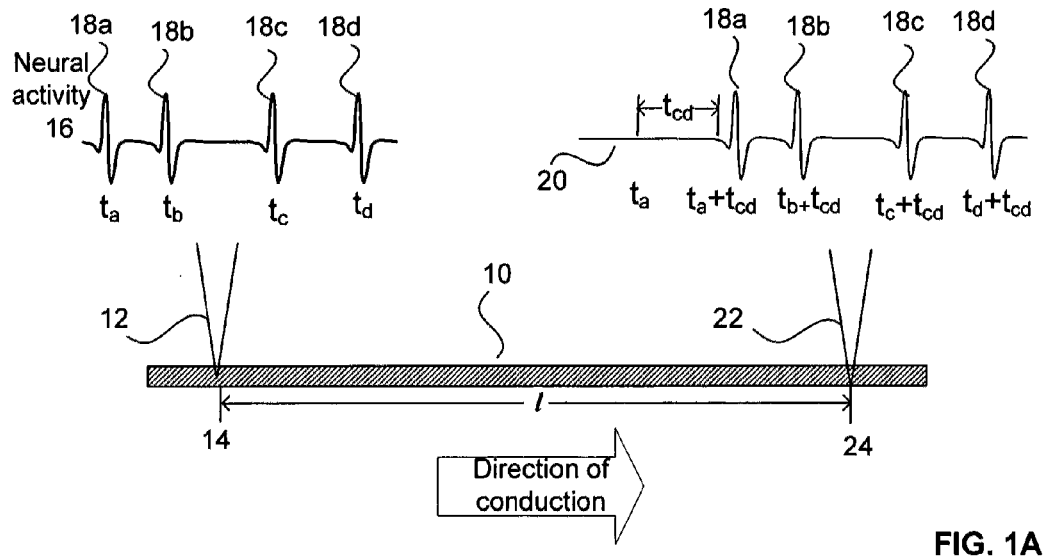
FIG. 1A is an illustration of conduction in a single nerve fiber.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Although the following terms are known in the art, they are generally defined below for the convenience of the reader:

Definitions

Central Nervous System (CNS)—the brain, spinal cord, optic nerves and retina.

Peripheral Nervous System (PNS)—all the nerves in the body that lie outside of the brain and spinal cord, i.e., the cranial nerves, spinal nerves, nerve plexuses, and their associated spinal and autonomic ganglia.

Autonomic Nervous System (ANS)—the portion of the nervous system that regulates involuntary body functions, including heart and circulation, respiration, digestion, temperature regulation, etc. The Autonomic nervous system includes two divisions, the sympathetic nervous system and the parasympathetic nervous system.

Sympathetic nervous system—the division of the autonomic nervous system, which, broadly speaking, functions to mobilize the body's energy and resources during times of stress and arousal to prepare for "fight or flight", e.g., it accelerates heart rate, constricts blood vessels, elevates blood pressure, etc.

Parasympathetic nervous system—the division of the autonomic nervous system that regulates body functions during relaxed states.

Neuron—a nerve cell, the basic functional unit of the nervous system. A neuron typically includes a cell body, and one or more processes called axons and dendrites.

Axon—An axon is a long slender process of a nerve cell that conducts electrical impulses away from the cell body.

Action Potential—a brief, regenerative change in membrane potential that propagates actively along membrane of neuron or other excitable cells.

Dendrite—A dendrite is a process of a nerve cell that conducts electrical impulses toward the cell body. Often, a neuron may have multiple, relatively short dendrites.

Nerve Fiber—The term "nerve fiber" may be used in connection with peripheral neurons to describe long slender processes (either axons or dendrites) that may conduct electrical impulses away from or toward the cell body.

Nerve—a cable-like bundle of multiple nerve fibers, capable of carrying signals between the central nervous system and other organs and tissues of the body. Cranial nerves may connect directly to parts of the brain.

Fascicle—a bundle of nerve fibers within a nerve. Each fascicle is surrounded by a dense sheath of tissue called perineurium, while a group of fascicles that make up a nerve are surrounded and held together by looser connective tissue called epineurium.

Nerve Plexus—a region of crossover and regrouping of nerve fibers from multiple nerves.

Ganglion—in the peripheral nervous system, a cluster of nerve cell bodies; sensory (afferent) ganglia lie along spinal column on the dorsal roots. Autonomic ganglia (containing the cell bodies of autonomic neurons) may lie parallel to the spinal column or in or near their target organs.

Spinal Root—root portion of spinal nerve, as it branches off of spinal cord and passes through bony canal through vertebra.

Methods and systems for modulating neural activity by producing conduction block in peripheral neural structures in a controlled fashion are disclosed herein. Effects of peripheral nerve block depend at least in part on the type of nerve or nerve fibers blocked and the target organ or tissue innervated by the blocked nerve or nerve fibers. It is believed that delivery of blocking stimuli to coincide at least in part with particular activity states in a subject may allow desired effects of blocking (e.g., modulation of immune or inflammatory response, decrease in pain, etc.) to be produced while limiting inconvenience, discomfort, and/or other undesired effects (numbness, diminished or altered sensation, decreased muscle force or control, interference with autonomic functions), or for other reasons. For example, blocking stimuli may be delivered during periods of reduced activity of the subject (including, but not limited to, physical activity, physiological activity, or other measures of activity, in all or a portion of the body of the subject). Effects of peripheral nerve block depend at least in part on the type of nerve or nerve fibers blocked and the target organ or tissue innervated by the blocked nerve or nerve fibers.

Figure 1B:
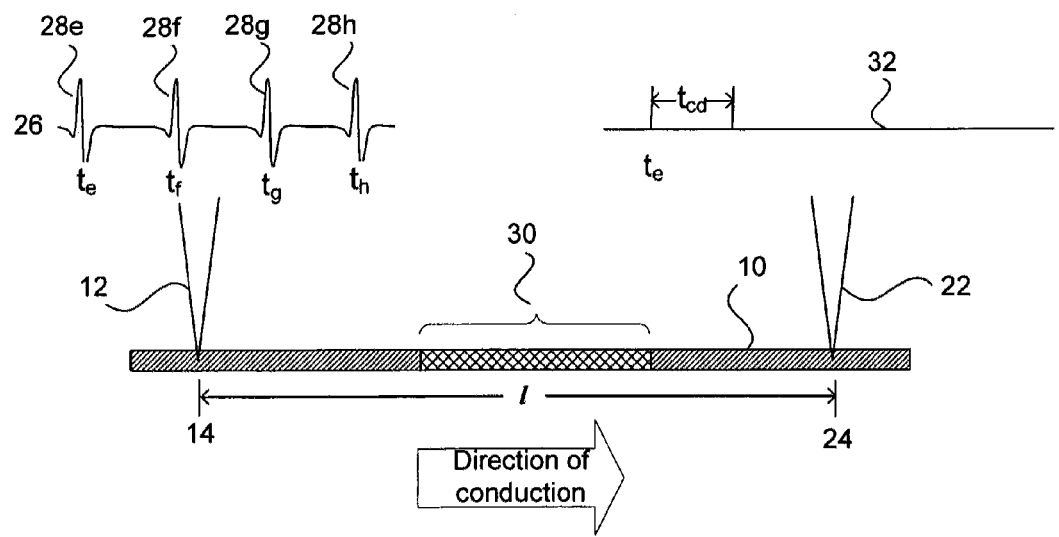
FIG. 1B is an illustration of conduction block in the single nerve fiber depicted in FIG. 1A.

By way of background, FIGS. 1A and 1B provide a conceptual illustration of the blocking of conduction of an action potential along a single nerve fiber. FIG. 1A depicts conduction of action potentials (referred to collectively as "neural activity") in a single nerve fiber 10 (an elongated nerve process, or axon or dendrite) when no conduction block is present. Neural activity may be sensed from nerve fiber 10 with, for example, an electrode 12 located at a first position 14 on nerve fiber 10. Sensed neural activity may be represented by trace 16, which includes action potentials 18a, 18b, 18c and 18d occurring at times $t_a$, $t_b$, $t_c$ and $t_d$. The direction of conduction of action potentials along nerve fiber 10 is indicated by the arrow. Trace 20, which may be sensed with electrode 22 at a second position 24 located at a distance l from first position 14 on nerve fiber 10, includes action potentials 18a, 18b, 18c and 18d occurring at times $t_a+t_{cd}$, $t_b+t_{cd}$, $t_c+t_{cd}$ and $t_d+t_{cd}$, where $t_{cd}$ is the conduction delay time, or the time for the action potentials to conduct down nerve fiber 10 from first position 14 to second position 24. Conduction delay time $t_{cd}$ is equal to l/v, where l is the distance between first position 14 and second position 24 and v is the conduction velocity.

FIG. 1B depicts the effect of a conduction block in nerve fiber 10, indicated by cross-hatching in blocked region 30. When conduction is blocked at region 30, action potentials 28e, 28f, 28g and 28h, occurring at times $t_e$, $t_f$, $t_g$ and $t_h$ in trace 26 may be sensed with electrode 12 at first position 14. However, conduction of the action potentials in the direction indicated by the arrow is blocked so they cannot travel past region 30 to second position 24. Accordingly, trace 32, which may be sensed with electrode 22 at second position 24, will not contain any action potentials.

FIGS. 2A-2F illustrate the effects of complete and partial conduction block on a nerve made up of multiple nerve fibers. A nerve 50 is shown in longitudinal section in FIG. 2A, and in cross section (taken at section line 2B-2B) in FIG. 2B. Nerve 50 contains multiple nerve fibers 54. An electrode 56 at first position 58 may record a compound signal 60 from nerve 50. Compound signal 60 is made up of the summation of action potentials produced by multiple individual nerve fibers (e.g., as may be produced in response to an electrical stimulus or other stimulus that activates multiple nerve fibers at substantially the same time). If the direction of conduction is as indicated by the arrow, an electrode 62 at second position 64 may record compound signal 66. Because action potentials on individual nerve fibers may travel at different conduction velocities, action potentials that sum to form compound signal 60 at first position 58 may not arrive at second position 64 at the same delays relative to each other. Accordingly, compound signal 66 may represent the summation of the same action potentials that made up compound signal 60, but because they arrive at second position 64 at different relative delays, compound signal 66 may have a different shape than compound signal 60.

FIG. 2C depicts nerve 50 in longitudinal section, with a complete conduction block in region 70, as indicated by cross-hatching. Conduction block is indicated in region 74 in the cross-section of the same nerve, taken at section line 2D-2D and shown in FIG. 2D. Compound signal 75 sensed at first position 58 is unchanged relative to compound signal 60 shown in FIG. 1A, but compound signal 76, sensed at second position 64 with electrode 62, includes no activity, because conduction of action potentials was blocked in all fibers at the blocked region as indicated at 70 and 74.

FIG. 2E depicts in longitudinal view nerve 50 with a partial conduction block, with blocked fibers in area 80, as indicated by cross-hatching. Conduction block is indicated by cross-hatching in area 84 in the cross-section shown in FIG. 2F, taken along section line 2F-2F in FIG. 2E. Compound signal 85 sensed at first position 58 is unchanged relative to compound signal 60 as shown in FIG. 2A, but compound signal 86, sensed at second position 64 with electrode 62, is of lower amplitude because conduction of action potentials was blocked in the subset of fibers passing through the blocked region as indicated at areas 80 and 84. Accordingly, compound signal 86 is formed by the summation of action potentials from those fibers lying outside of area 80, i.e. fibers lying within region 88 in cross-section of FIG. 2F. As seen in the cross-section of FIG. 2F, when a partial conduction block is produced in a nerve, a subset of the nerve fibers (lying within area 84) may be blocked, and another subset of the nerve fibers (lying within region 88) may conduct as usual. In the example shown in FIG. 2F, the blocked subset of nerve fibers falls within a particular spatial distribution. In some cases, a subset of nerve fibers within a nerve may be blocked based on fiber diameter, fiber type, presence of a biomarker, or other parameter instead of or in addition to the location of the nerve fiber with the nerve.

As used herein, the term "conduction" encompasses not only the conduction of action potentials along a nerve fiber, but also (unless the context dictates otherwise) the conduction or transmission of neural activity across a synapse from a pre-synaptic cell to a post-synaptic cell, e.g. from a pre-synaptic neuron to a post-synaptic neuron or from a pre-synaptic neuron to a muscle or other end organ. Synaptic transmission may be chemical or electrical (ionic) in nature. Similarly, producing a conduction block in a peripheral neural structure may include blocking conduction of an action potential along a nerve fiber, and/or blocking synaptic transmission from a pre-synaptic cell to a post-synaptic cell. Chemical blocking agents having various mechanisms or sites of action may be used, and unless specifically stated, systems and/or methods as claimed herein are not limited to the use of chemical blocking agents operating by specific mechanisms or at specific sites.

Conduction block in peripheral nerves may be produced by application of chemical blocking agents, as described elsewhere herein, or by various other approaches as known to those of skill in the art. For example, commonly owned U.S. patent application Ser. No. 11/999,721, titled "METHOD AND SYSTEM FOR CYCLICAL NEURAL MODULATION BASED ON ACTIVITY" filed 5 Dec. 2007, and listing as inventors Ralph G. Dacey, Jr., Gregory J. Della Rocca, Colin P. Derdeyn, Joshua L. Dowling, Eleanor V. Goodall, Roderick A. Hyde, Muriel Y. Ishikawa, Jordin T. Kare, Eric C. Leuthardt, Nathan P. Myhrvold, Michael A. Smith, Lowell L. Wood, Jr., Victoria Y. H. Wood, Gregory J. Zipfel, which is incorporated herein by reference in its entirety, describes various approaches for blocking conduction in peripheral neural structures.

Figure 3:
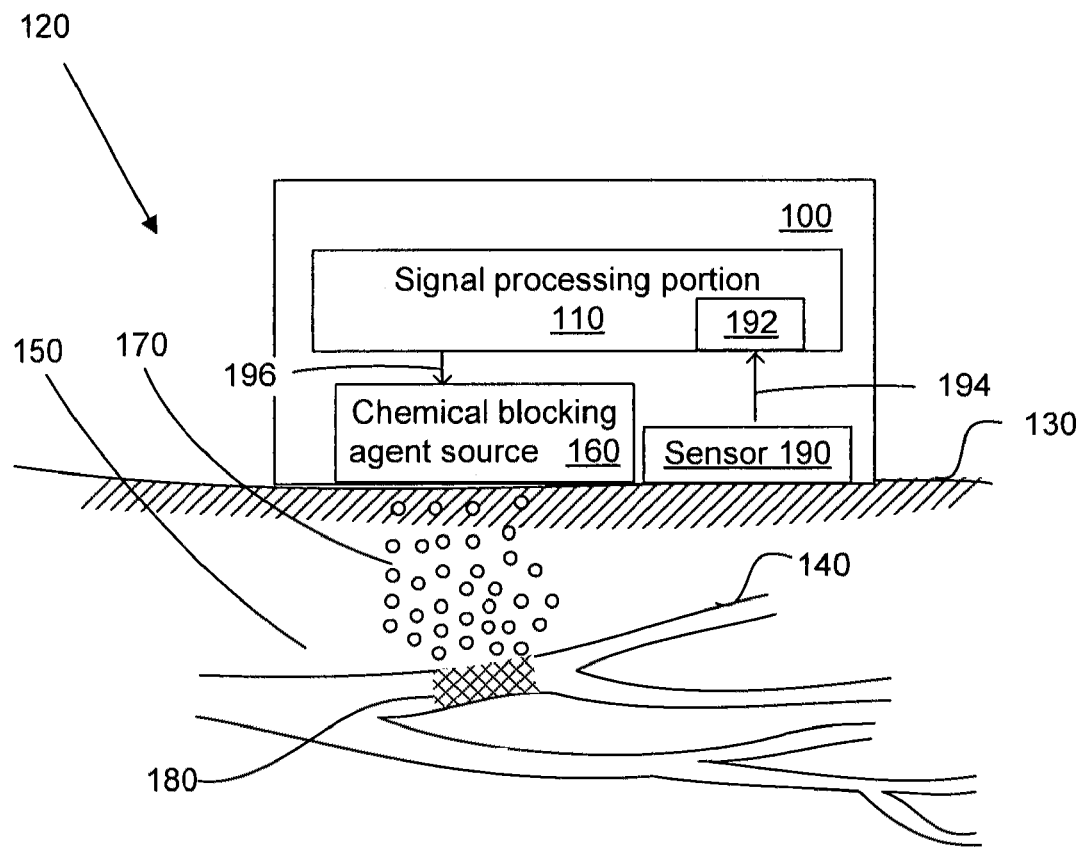
FIG. 3 is a schematic diagram of a transdermal system for producing conduction block in a peripheral neural structure.

FIG. 3 is a schematic diagram illustrating a neural modulation system 100 for modulating neural activity by blocking conduction in at least a portion of a peripheral neural structure 140. A body portion of a subject is indicated generally at 120, including skin surface 130 overlying peripheral neural structure 140 (in this example, a peripheral nerve) and surrounding tissue 150. Neural modulation system 100 includes chemical blocking agent source 160, which is capable of delivering chemical blocking agent 170 to block conduction in region 180 of peripheral neural structure 140. The neural modulation system 100 includes a signal input structure 192 configured to receive a signal 194 indicative of an activity state of at least a portion 120 of a body of a subject innervated by a peripheral neural structure 140, a signal processing portion 110 configured to distinguish a first activity state of the at least a portion 120 of the body of the subject innervated by peripheral neural structure 140 from a second activity state of the at least a portion 120 of the body of the subject innervated by the peripheral neural structure 140 from signal 194 received at the signal input structure 192 and generate a chemical blocking agent control signal 196 for driving delivery of a chemical blocking agent 170. Chemical blocking agent 170 may reversibly block conduction in the peripheral neural structure 140 of the subject during at least a portion of the first activity state. Chemical blocking agent source 160 may be configured to deliver a chemical blocking agent responsive to the chemical blocking agent control signal 196. Sensor 190 may sense at least one parameter indicative of an activity state in the subject, which may be an overall activity level of the subject, or a level of use or activity of a body portion innervated by peripheral neural structure 140. A signal 194 from sensor 190 may be connected to signal input structure 192 of signal processing portion 110.

Neural modulation system 100, as depicted in FIG. 3, delivers chemical blocking agent 170 transdermally under control of signal processing portion 110. In general, a chemical blocking agent may be delivered through or across the skin of a subject using either passive or active transdermal delivery. Passive transdermal delivery methods utilize passive diffusion of agents across the skin. In the case that passive transdermal delivery is used, signal processing portion 110 may control the release or delivery of chemical blocking agent 170 from chemical blocking agent source 160 to skin surface 130 and chemical blocking agent 170 may travel through or across the skin by passive diffusion. Active transdermal delivery methods utilize an energy source (which may be a component of chemical blocking agent source 160) to increase the flux of chemical blocking agent 170 across the skin either by altering the barrier function of the skin (primarily the stratum corneum) or by increasing the energy of the agent molecules. The rate of delivery of chemical blocking agent 170 through the skin of the subject may be proportional to the overall level of energy applied under control of signal processing portion 110.

Different methods of active transdermal agent delivery may use different forms of energy to increase the flux of an agent across the skin, including, but not limited to, electrical energy (e.g., iontophoresis and electroporation), ultrasonic energy (phonophoresis, sonophoresis), magnetic energy (magnetophoresis), and thermal energy (see, e.g., Gordon, R. D. and Peterson, T. A; "Transdermal Delivery: 4 Myths about transdermal drug delivery," Drug Delivery Technology; http://www.drugdeliverytech.com/cgi-bin/articles.cgi?idArticle=143, which is incorporated herein by reference in its entirety).

Figure 4:
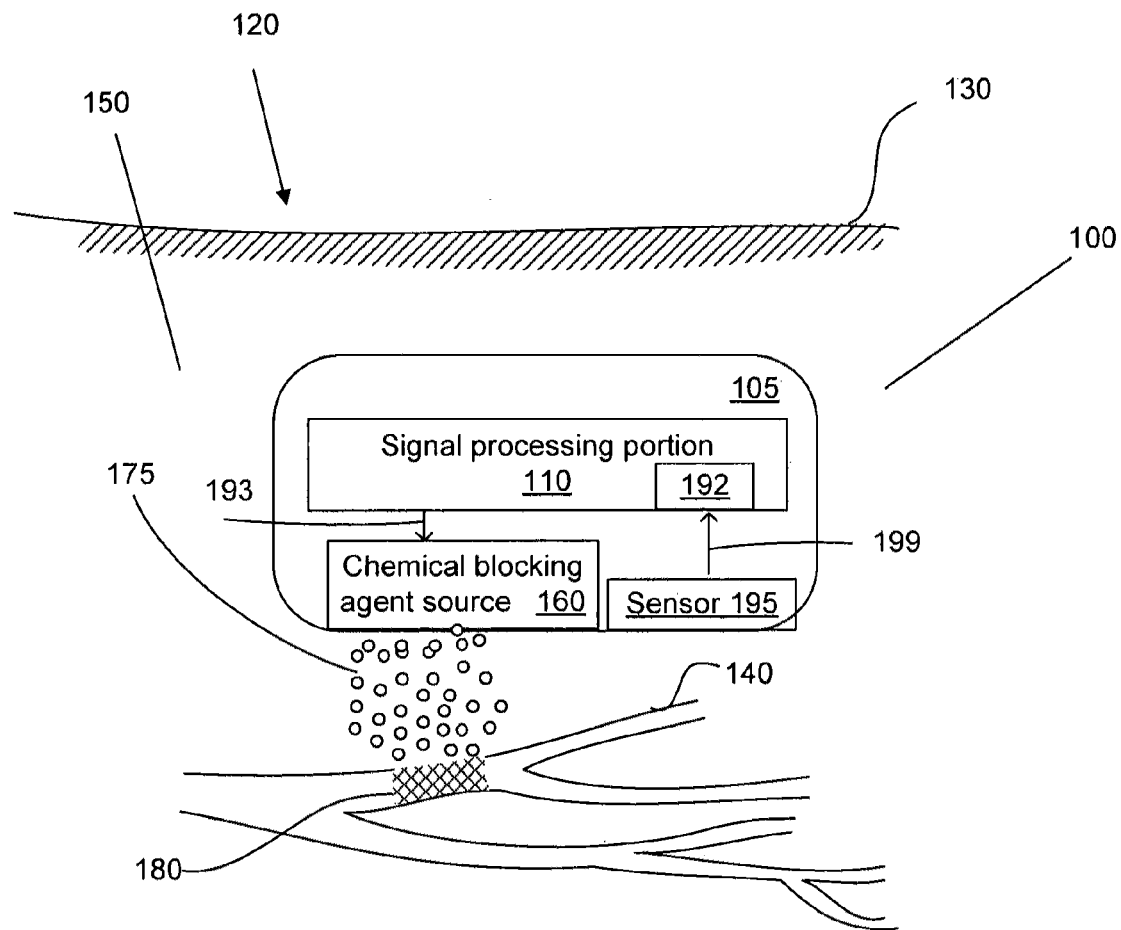
FIG. 4 is a schematic diagram of an implanted system for producing conduction block in a peripheral neural structure.

A chemical blocking agent may be delivered through or across the skin of the subject, as depicted in FIG. 3, or, alternatively, a chemical blocking agent may be delivered with an implanted (or partially implanted) system, as depicted in FIG. 4.

FIG. 4 depicts in schematic form a neural modulation system 100 including implantable neural modulation device 105 including chemical blocking agent source 160. Neural modulation system 100 for modulates neural activity by blocking conduction in at least a portion of a peripheral neural structure 140. A body portion of a subject is indicated generally at 120, including skin surface 130, peripheral neural structure 140 (here, a peripheral nerve), and surrounding tissue 150. Implantable neural modulation device 105 includes chemical blocking agent source 160, which is capable of delivering chemical blocking agent 175 to block conduction in region 180 of peripheral neural structure 140. Implantable neural modulation device 105 includes a signal input structure 192 configured to receive a signal 199 indicative of an activity state of at least a portion 120 of a body of a subject innervated by a peripheral neural structure 140, a signal processing portion 110 configured to distinguish a first activity state of the at least a portion 120 of the body of the subject innervated by peripheral neural structure 140 from a second activity state of the at least a portion 120 of the body of the subject innervated by the peripheral neural structure 140 from signal 199 received at the signal input structure 192 and generate a chemical blocking agent control signal 193 for driving delivery of a chemical blocking agent 175. Chemical blocking agent 175 may reversibly block conduction in the peripheral neural structure 140 of the subject during at least a portion of the first activity state; chemical blocking agent source 160 may be configured to deliver a chemical blocking agent responsive to the chemical blocking agent control signal 193. Sensor 195 may sense at least one parameter indicative of an activity state in the subject, which may be an overall activity level of the subject, or a level of use or activity of a body portion innervated by peripheral neural structure 140. A signal 199 from sensor 195 may be connected to signal input structure 192 of signal processing portion 115.

Various types of implanted devices may be used for delivering chemical blocking agents, as will be described in greater detail elsewhere herein. Whether a transdermal or implanted system is used for delivering a chemical blocking agent, the general approach for controlling delivery of the chemical blocking agent is similar and is based on an activity state in the subject, which as noted above may be an overall activity level of the subject, or a level of use or activity of a body portion innervated by peripheral neural structure 140.

The term "activity state" refers to one of at least two possible categories of activity that are characterized by and distinguishable from each other by one or more quantifiable parameters. Activity may refer to overall activity of the subject or use or activity of a body portion innervated by the peripheral neural structure. Activity may include or be reflected by physical activity, physiological activity, or other measures or indicators of activity, as described in greater detail elsewhere herein.

For purposes of methods as disclosed herein, at least two activity states may be defined, with appropriate values or value ranges of the one or more quantifiable parameters associated therewith. The different activity states may differ with regard to the level of activity, or, in some cases, the nature of the activity. In some cases, the overall activity of the subject may be lower in the first activity state than in the second activity state. For example, the first activity state may be a "sleep state" and the second activity state may be a "waking state." Alternatively, the first activity state may be a "resting," "lying down" or "sitting" activity state while the second activity state may be a "moving about," "standing" or "walking" activity state.

The activity or use of a specific portion of the subject's body, rather than the overall activity of the subject, may be of interest. For example, the first and second activity states may be defined such that the use of a body portion innervated by the peripheral neural structure by the subject is lower in the first activity state than in the second activity state. If the body portion innervated by the peripheral neural structure is the subject's arm, a low use state may be obtained when the arm is resting in the subject's lap, on an arm rest or table top, or in a sling, while the subject stands or walks. Low use or activity of the subject's arm may also be obtained while the overall activity of the subject is low, e.g. the subject is lying down or sleeping. Conversely, a moderate or high use or activity state of a body portion, e.g., the subject's arm, may be obtained while the subject's overall activity level is either high or low. For example, the subject could use the arm for writing, typing, holding a book, knitting, etc. while sitting quietly with a low overall activity level. A subject may also have a high use or activity state of, e.g., an arm, in combination with an overall high activity level. First and second activity states may be physical activity states of the subject, which in some cases may be overall physical activity states of the subject, and in some cases may be physical activity states of a portion of the body of the subject innervated by the peripheral neural structure. Activity states may be defined by various types of muscle activity, relating not only to gross motor activities, but to fine motor activities, and appropriately positioned sensors may detect muscle activity or other related parameters corresponding to particular facial expressions or eye motions, or corresponding to specific actions, such as eating, drinking, talking, or smoking, e.g. as indicated by specific mouth movements.

Figure 5:
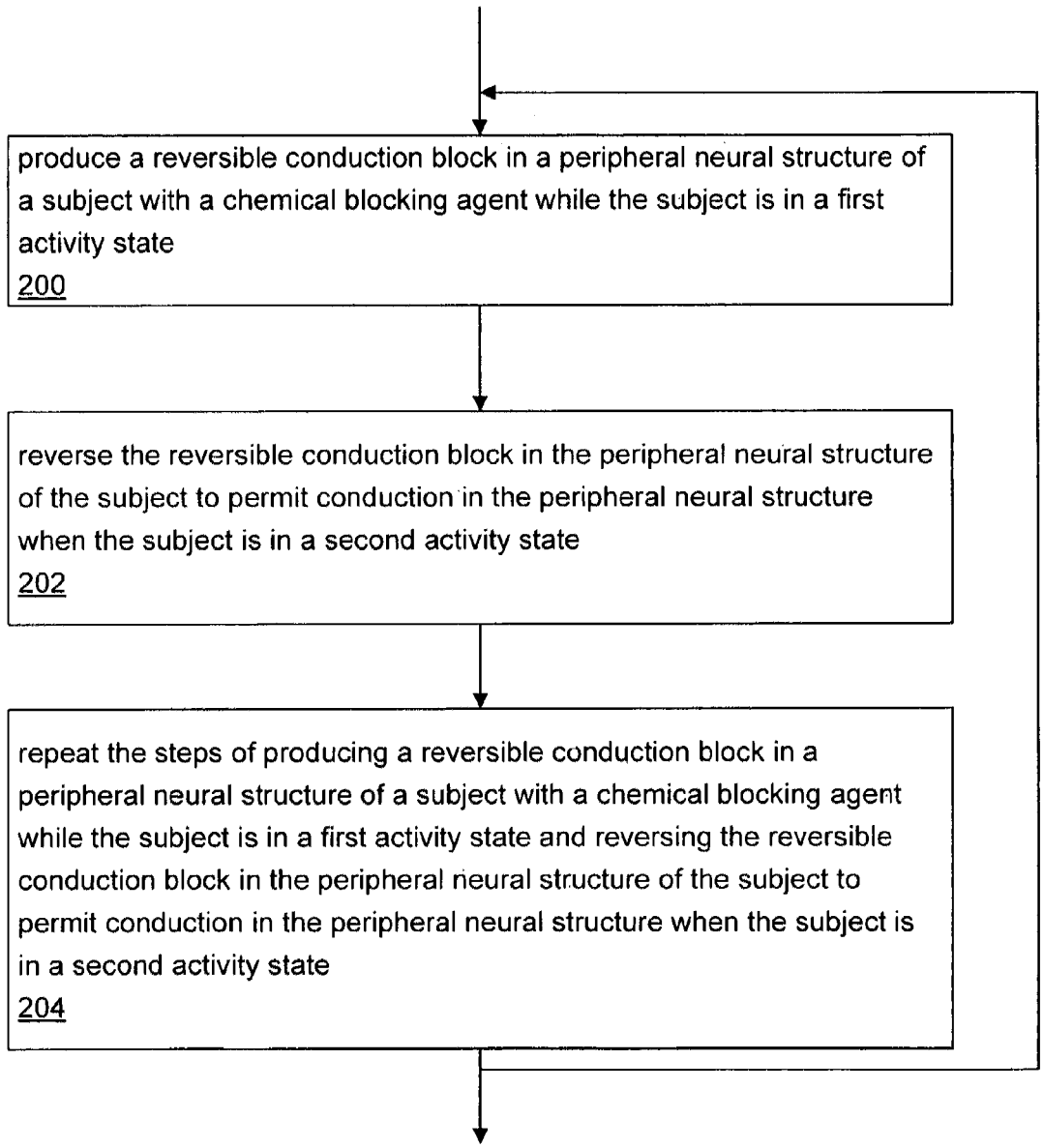
FIG. 5 is a flow diagram of method of modulating neural activity.

FIG. 5 illustrates a method of modulating neural activity that may be carried out, for example, using a system as depicted in FIG. 3 or FIG. 4. The method shown in FIG. 5 includes the steps of producing a reversible conduction block in a peripheral neural structure of a subject with a chemical blocking agent while the subject is in a first activity state (step 200), reversing the reversible conduction block in the peripheral neural structure of the subject to permit conduction in the peripheral neural structure when the subject is in a second activity state (step 202), and repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state (step 204).

The method of modulating neural activity as shown generally in FIG. 5 includes producing a reversible conduction block in a peripheral neural structure of a subject, which may be, for example, a peripheral nerve, a spinal root, an autonomic ganglion, or a nerve plexus. A peripheral nerve may be a sensory and/or motor nerve, an autonomic nerve (including sympathetic and/or parasympathetic nerve fibers, or a mixture of sensory, motor, sensory-motor, and/or autonomic nerve fibers). Examples of specific nerves that may be subject to reversible conduction block include the radial nerve, median nerve, ulnar nerve, femoral nerve, obturator nerve, sciatic nerve, popliteal nerve, tibial nerve, peroneal nerve, vagus nerve, and facial nerve. The geniculate ganglion is an example of a specific ganglion that may blocked reversibly.

In the practice of the method outlined in FIG. 5, the first activity state and the second activity state may be defined in several different ways, depending upon the intended application of the method. In some cases, as discussed previously, the first and second activity states may represent first and second overall activity states of the subject, and in other cases, the use of a body portion innervated by the peripheral neural structure may be of interest, and the first and second activity states may represent first and second states of use of the innervated body portion.

Figure 6:
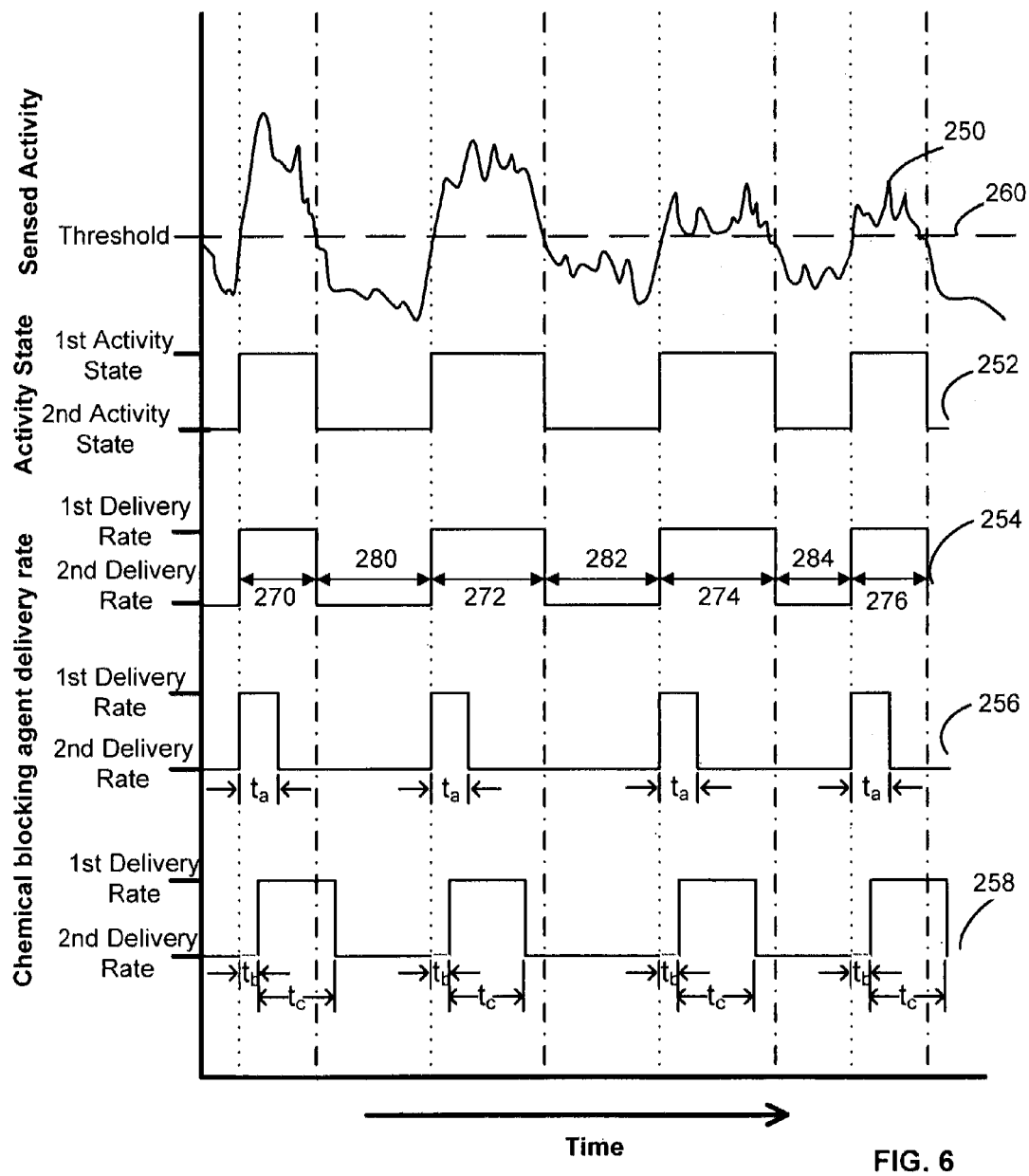
FIG. 6 is an illustration of delivery patterns for blocking stimuli.

FIG. 6 illustrates sensed activity, represented by trace 250; activity state as determined from sensed activity, represented by trace 252; and several examples of chemical blocking agent delivery patterns, which may be responsive to the sensed activity, represented by traces 254, 256 and 258. Time is indicated on the x-axis. Methods for delivering blocking stimuli (including but not limited to chemical blocking agents), responsive to and/or relative to sensed activity is described in greater detail in commonly owned U.S. patent application Ser. No. 11/999,721, which, as noted elsewhere herein, is incorporated herein by reference in its entirety. Trace 250 is an illustration of a sensed activity of the type that might be detected from a subject over a period of time. Trace 250 does not represent any specific type of signal (it could be, for example, a physiological signal such as a heart rate or respiration rate, or a physical signal such as motion detection or pressure signal). In this example, the activity in the subject is classified into one of two possible activity states, a first activity state and a second activity state, and it is assumed that higher values of the signal indicate that the subject is more active and lower values of the signal indicate that the subject is less active. By setting an appropriate threshold value, as indicated at 260, it may be possible to distinguish between the first activity state (during which the value of trace 250 is above the threshold value 260 and the second activity state (during which the value of trace 250 is below the threshold value 260). Trace 252 may be an overall activity state (which might be determined from heart rate, for example) or an activity or use state of a portion of the body of the subject (which might be determined from activity of a particular muscle, for example).

Examples of several representative patterns for application of blocking stimuli are also illustrated in FIG. 6. The horizontal axis represents time, while the vertical axis represents delivery rate (e.g., pumping rate, flux across skin, etc.) Trace 254 depicts a chemical blocking agent delivery pattern that corresponds directly to the activity state, with chemical blocking agent delivered (at first delivery rate, as indicated in FIG. 6) while the subject is in the first activity state and the delivery of the chemical blocking agent effectively discontinued (e.g., stopped, reduced, or rendered ineffective, as indicated by the lower, second delivery rate in FIG. 6) while the subject is in the second activity state. The second delivery rate may be zero, or non-zero but insufficient to block conduction in the peripheral neural structure. The chemical blocking agent pattern represented by trace 254 includes multiple blocking periods 270, 272, 274 and 276, during which a chemical blocking agent sufficient to produce a reversible conduction block of at least a portion of the peripheral neural structure of the subject is delivered at a first rate, separated by release periods 280, 282 and 284, during which delivery of the chemical blocking agent is effectively discontinued. Blocking periods 270, 272, 274 and 276 coincide with a first activity state in the subject and release periods 280, 282, 284 and 286 coincide at least in part with a second activity state in the subject.

Trace 256 depicts a chemical blocking agent delivery pattern in which a chemical blocking agent is delivered at the onset of the first activity state and discontinued after a time $t_a$ after the onset of the first activity state. Trace 258 depicts a chemical blocking agent pattern in which a chemical blocking agent is delivered at a time $t_b$ after the onset of the first activity state and removed at a time $t_c$ after it was delivered. In this example, the period during which the chemical blocking agent is delivered may extend into the second activity state in the subject.

In some applications, the steps of producing a reversible conduction block in a peripheral neural structure of a subject while the subject is in a first activity state and reversing the reversible conduction block (e.g., by stopping or significantly reducing delivery of the chemical blocking agent) in the peripheral neural structure of the subject to permit conduction in the peripheral neural structure when the subject is in a second activity state may be repeated over a period of time sufficient to produce a modulation of an immune response in a region innervated by the peripheral neural structure.

In some applications, the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state may be repeated over a period of time sufficient to produce a modulation of an inflammatory response in a region innervated by the peripheral neural structure.

A chemical blocking agent may be delivered intermittently responsive to activity state (for example according to a pattern as depicted in FIG. 6) until a desired modulation of an immune or inflammatory response is obtained. Modulation of an inflammatory or immune response may be produced using a method or system as described herein, and may involve producing a total or partial block to a sensory nerve innervating a limb, join, or digit, to produce an effect e.g. as described in Kane et al., "Protective effect of sensory denervation in inflammatory arthritis (evidence of regulatory neuroimmune pathways in the arthritic joint)," Annals of Rheumatic Disease 2005; 64:325-327. doi: 10.1136/ard.2004.022277, or as described in Razavi et al., "TRPV1+ sensory neurons control β cell stress and islet inflammation in autoimmune diabetes," (showing elimination of activity from sensory neurons innervating the pancreas may prevent development of diabetes); Cell; Dec. 15, 2006; pp. 1123-1135; Vol. 127, each of which is incorporated herein by reference in its entirety.

The amount of time needed to produce modulation of an immune response or inflammatory response may be determined prior to use of the method, based on experimental or clinical data, or the method may be carried out until an appropriate modulation of immune or inflammatory response is obtained as determined by measurement of indicators of immune or inflammatory response, as known to those of skill in the art. For example, inflammation may be indicated by one or more of swelling, color, temperature, or pain or tenderness, and these parameters may be determined qualitatively or quantitatively, as described in U.S. Pat. No. 7,226,426, which is incorporated herein by reference in its entirety. Inflammation may also be indicated by the presence of T-lymphocytes or macrophages, which may be detected immunohistochemically, for example as described in Rooney, T.; Bresnihan, B.; Andersson, U.; Gogarty, M.; Kraan, M.; Schumacker, H. R.; Ulfgren, A.-K.; Veale, D. J.; Youssef, P. P.; and Tak, P. P; "Microscopic measurement of inflammation in synovial tissue: inter-observer agreement for manual quantitative, semi-quantitative and computerized digital image analysis"; Annals of Rheumatic Disease; 2007; Vol. 66, pp. 1656-1660; doi:10.1136/ard.2006.0611430; by eosinophils, cytokines, chemokines, and/or leukotrienes, as described in Howarth, P. H.; Persson, C. G. A.; Meltzer, E. O.; Jacobson, M. R.; Durhan, S. R.; and Silkoff, P. E.; "Objective monitoring of nasal airway inflammation in rhinitis"; J. Allergy Clin. Immunol.; 2005; Vol. 115; pp. S414-S441; and by other biomarkers, such as certain 14-3-3 proteins, as described in Kilani, R. T.; Maksymowych, W. P.; Aitken, A.; Boire, G.; St. Pierre, Y.; Li, Y.; and Ghahary, A.; "Detection of high levels of 2 specific isoforms of 14-3-3 proteins in synovial fluid from patients with join inflammation"; J. Rheumatology; 2007; Vol. 34, No. 8; pp. 1650-1657; each of which is incorporated herein by reference in its entirety. Inflammation may also be indicated by products of tissue degradation, and/or immune response may be indicated by one or more of antibodies, immune cells, or chemical markers of immune response or inflammation, as described in Poole, A. R.; "Immunochemical markers of joint inflammation, skeletal damage and repair: where are we now?"; Annals of Rheumatic Disease; 1994; Vol. 53; pp. 3-5; doi:10.1136/ard.53.1.3, which is incorporated herein by reference in its entirety.

The amount of time needed to produce modulation of an immune response or inflammatory response will depend upon a number of factors, including the nature and pattern of delivery of the chemical blocking agent, the peripheral neural structure in which conduction block is produced, and the nature of the immune or inflammatory response of concern and the level of modulation that is to be produced.

Figure 7:
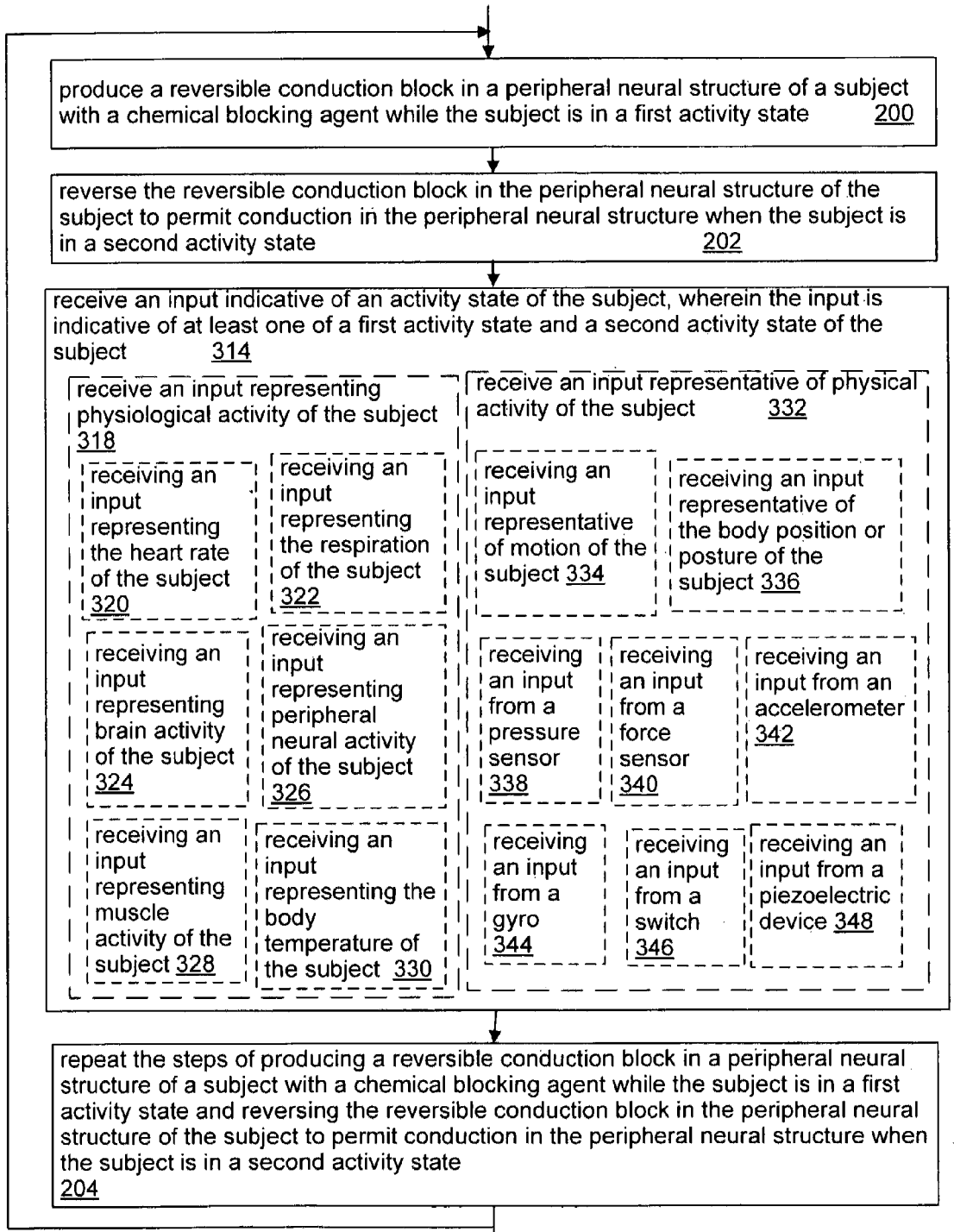
FIG. 7 is a flow diagram of method of modulating neural activity.

FIG. 7 illustrates variants of the method shown generally in FIG. 5. The method of FIG. 7 includes the steps of producing a reversible conduction block in a peripheral neural structure of a subject with a chemical blocking agent while the subject is in a first activity state (step 200), reversing the reversible conduction block in the peripheral neural structure of the subject to permit conduction in the peripheral neural structure when the subject is in a second activity state (step 202), receiving an input indicative of an activity state of the subject, wherein the input is indicative of at least one of a first activity state and a second activity state of the subject (314) and repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state (step 204). In some embodiments, the method may include receiving an input representing physiological activity of the subject, as indicated at 318, which may include, for example, receiving an input representing the heart rate (as indicated at 320), respiration of the subject (as indicated at 322), brain activity (as indicated at 324), peripheral neural (as indicated at 326), muscle activity (as indicated at 328), or body temperature of the subject (as indicated at 330). Methods and devices for sensing these and other physiological signals or parameters are well known to those of skill in the art.

A physiological sensor as used in the method of FIG. 7 may be configured to generate a signal indicative of activity of the heart of the subject, activity of the brain of the subject, activity of a peripheral neural system of the subject, activity of a muscle of the subject, respiration of the subject, body temperature of the subject, or other physiological signals that may be indicative of an activity state of all or a portion of the body of the subject. The detection of these and other physiological signals is known to those of skill in the art. Examples of some possible physiological signals that may indicate activity of all or a portion of a body of a subject include electroencephalographic signals (EEG), electromyographic signals (EMG), electrocardiographic signals (ECG), electrocardiogram morphology, heart rate, blood pressure, blood oxygenation, respiration rate, respiratory volume, skin conductivity, or body temperature (e.g., core temperature, subcutaneous temperature). Receiving an input indicative of an activity state of the subject may include receiving an input representing a rest or waking state of the subject; for example, rest or waking state of a subject may be determined based on physiological parameters (EEG, heart rate, respiration rate, etc.). Specific activity states such as sleep may be indicated by particular chemical indicators, e.g. concentration of melatonin or melanin-concentrating hormone (MCH) and orexin/hypocretin or other measures (see, for example, U.S. Patent Publication 2005/0215947, and Burdakov, D., Gerasimenko, O., and Verkhratsky, A. "Physiological changes in glucose differentially modulate excitability of hypothalamic melanin-concentrating hormone and orexin neurons in situ." J. Neurosci. 2005, Vol. 25, No. 9, pp. 2429-2433, both of which are incorporated herein by reference in their entirety).

In other embodiments, receiving an input indicative of an activity state of the subject may include receiving an input representative of physical activity of the subject (as indicated at 332 in FIG. 7). The method may include receiving an input representative of motion of the subject (as indicated at 334), receiving an input representative of the body position or posture of the subject (as indicated at 336), receiving an input from a pressure sensor (as indicated at 338), receiving an input from a force sensor (as indicated at 340), receiving an input from an accelerometer (as indicated at 342), receiving an input from a gyro (as indicated at 344), receiving an input from a switch (as indicated at 346), such as, for example a mercury switch, or receiving an input from a piezoelectric device (as indicated at 348). Other activity sensing devices, as known to those of skill in the art, may be used as well. In FIG. 7 and in other figures herein, boxes surrounded by dashed lines represent alternative or optional steps or system components.

A rest or waking state may be determined based on physical activity. For example, resting state may be associated with a lying down posture and/or low level of motion or activity, while a waking or active state may be associated with an upright posture and/or a higher level of activity. A physical activity sensor may be configured to generate a signal indicative of motion or acceleration of the at least a portion of the body of the subject innervated by the peripheral neural structure. In some embodiments, the physical activity sensor may be configured to generate a signal indicative of a body position or posture of the subject. Physical activity sensors may sense various aspects of posture or movement (amplitude, frequency, direction, etc.) and may include various types of sensors, singly or in combination. For example, see U.S. Pat. No. 5,031,618, which is incorporated herein by reference in its entirety.

Examples of physiological and physical sensors are provided in The Biomedical Engineering Handbook, Second Edition, Volume I, J. D. Bronzino, Ed., Copyright 2000, CRC Press LLC, section V, pp. V-1-51-9, which is incorporated herein by reference.

As such, a transdermal or implantable delivery system for delivery of chemical blocking agent may incorporate one or more sensors such as, for example, a temperature sensor, a pulse rate sensor, a blood glucose sensor, a blood pressure sensor or a pH sensor under closed-loop feedback control in which the chemical and/or physiological state of the subject is monitored to determine the appropriate time for dosing. Examples of transdermal delivery devices with sensors and closed loop feedback systems are described in U.S. Pat. Nos. 5,224,928 and 5,997,501, which are incorporated herein by reference in their entirety. Examples of implantable delivery devices with sensors and closed loop feedback systems are described in U.S. Pat. Nos. 6,464,687; 6,802,811; 7,072,802; and 7,108,680, which are incorporated herein by reference in their entirety. The implantable device may sense chemical or physiological states associated with the activity state of the subject and administer one or more chemical blocking agents accordingly. For example, analysis of nerve activity such as sympathetic and vagal tone balance may be used to assess whether a subject is awake or asleep as described in U.S. Pat. No. 7,319,899, which is incorporated herein by reference in its entirety. In some instances, an implantable delivery system may monitor a physiological parameter of a subject which varies as a function of the subject's activity state as described in U.S. Pat. No. 7,167,743, which is incorporated herein by reference in its entirety.

Figure 8:
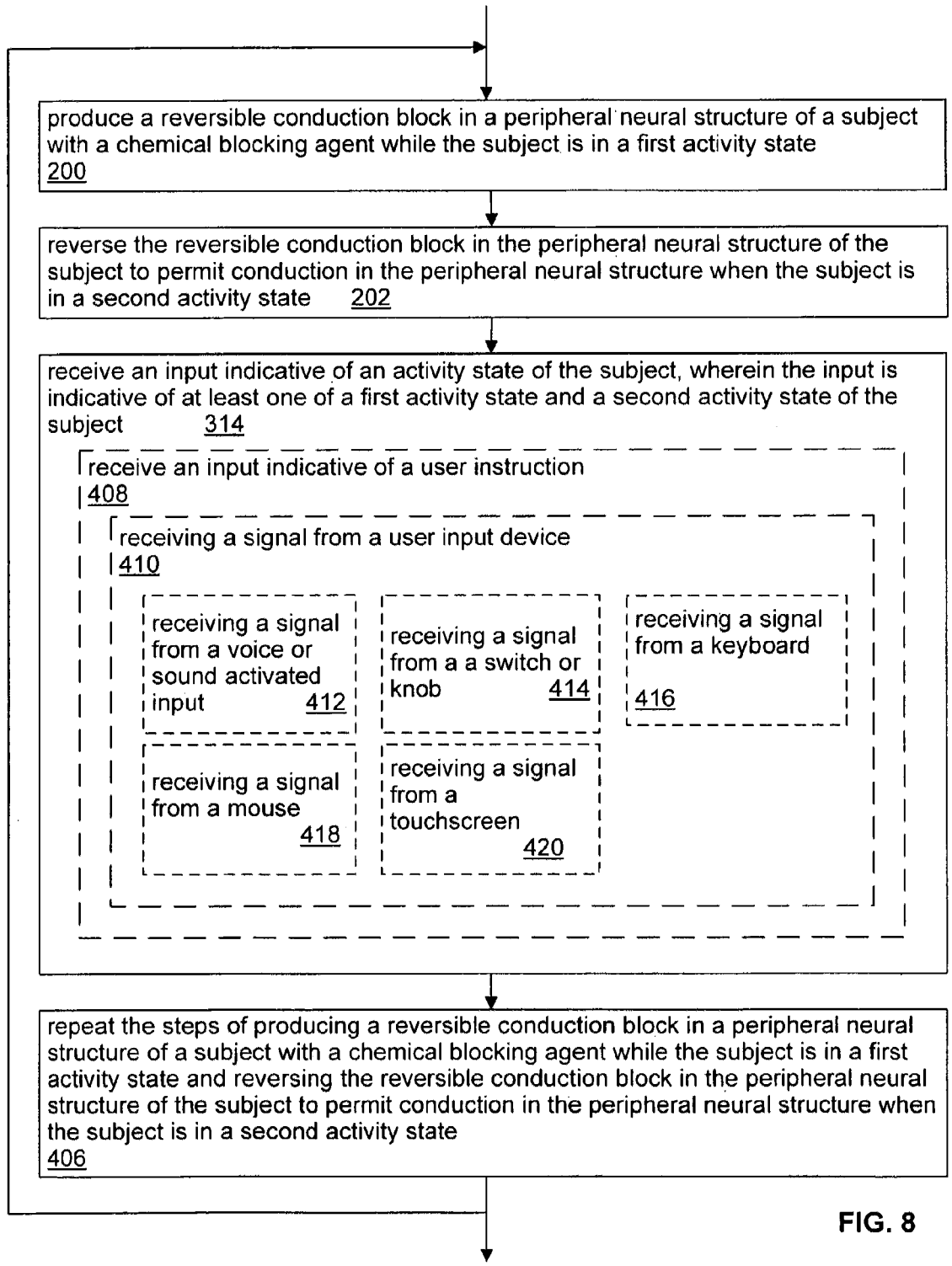
FIG. 8 is a flow diagram of method of modulating neural activity.

FIG. 8 illustrates further variants of the method shown generally in FIG. 5. The method of FIG. 8 includes the steps of producing a reversible conduction block in a peripheral neural structure of a subject with a chemical blocking agent while the subject is in a first activity state (step 200), reversing the reversible conduction block in the peripheral neural structure of the subject to permit conduction in the peripheral neural structure when the subject is in a second activity state (step 202), receiving an input indicative of an activity state of the subject, wherein the input is indicative of at least one of a first activity state and a second activity state of the subject (314) and repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state (step 406). The method further includes receiving an input indicative of a user instruction, as indicated at 408.

Receiving an input indicative of a user instruction may include receiving a signal from a user input device (as indicated at 410), which may include, for example, receiving a signal from a voice or sound activated input (as indicated at 412), a switch or knob (as indicated at 414), a keyboard (as indicated at 416), a mouse (as indicated at 418), a touch screen (as indicated at 420), or any sort of input device allowing a user to enter an instruction or select an option from a list of possible options, as known to those of skill in the art. User instructions may also be received from user-controlled intermediate device; e.g., a user instruction may be transmitted from a remote controller, a cell phone or remote computer operated by the user. The user may be a medical care provider, for example. Instructions may be transmitted electronically, electromagnetically, optically, acoustically, mechanically, or by other methods known to those of skill in the art, via one or more device or transmission media.

Delivery of a chemical blocking agent by a transdermal delivery system may be controlled either by the subject or other individual using on/off and/or high/low settings, for example, as described in U.S. Pat. No. 5,224,927, which is incorporated herein by reference in its entirety. For example, the subject may choose to turn on the transdermal delivery device during times of rest and turn off the device during times of activity. As an example, an iontophoresis transdermal delivery method has been described for on-demand, controlled dosing of the opioid analgesic fentanyl for pain management in response to activation of its electronic circuitry by the patient (Powers I. "Fentanyl HCl iontophoretic transdermal system (ITS): clinical application of iontophoretic technology in the management of acute postoperative pain." Br. J. Anaesth. 2007, Vol. 98, No. 1, pp. 4-11, which is incorporated herein by reference in its entirety). In the present context, delivery of chemical blocking agent would be responsive to activity level (overall activity level of the subject or activity level of a portion of the subject's body), rather than to sensation of pain. In some instances, it may be of benefit to limit the number of doses allowed by the subject. For example, the transdermal delivery method may incorporate a preprogrammed number of doses allowed during a given time period.

Receiving an input indicative of a user instruction may include receiving an input indicative of an instruction to modify a definition of a first activity state or receiving an input indicative of an instruction to modify a definition of a second activity state. For example, the definition of a first or second activity state may include a threshold level, e.g. as depicted in FIG. 6, at reference number 260.

As depicted in FIG. 8, receiving an input indicative of an activity state of the subject may in some embodiments include receiving an input indicative of a user instruction as an alternative to sensing a parameter indicative of the activity state of the subject (e.g., a physical or physiological activity).

In other embodiments (not depicted), receiving an input indicative of a user instruction may be performed in addition to sensing a parameter indicative of the activity state of the subject. For example, a user input may be used to override delivery of blocking stimuli determined from a sensed parameter, or to modify a pattern of delivery of blocking stimuli.

In a method as shown generally in FIGS. 5, 7 and 8, producing a reversible conduction block in a peripheral neural structure of a subject may include delivering a chemical blocking agent with a chemical blocking agent source positioned in proximity to the body of the subject. For example, the chemical blocking agent source may be located in or on a wrap adapted to be positioned around at least a portion of the body of the subject; in or on a bandage or patch configured to be adhered or secured to at least a portion of skin, tissue or mucous membrane of the subject; in or on a bracelet, anklet, or cuff configured to be worn on a limb of the subject; in or on a collar or necklace configured to be worn on a neck of the subject; or in or on a fitted garment or item of clothing configured to be worn by the subject.

Figure 9:
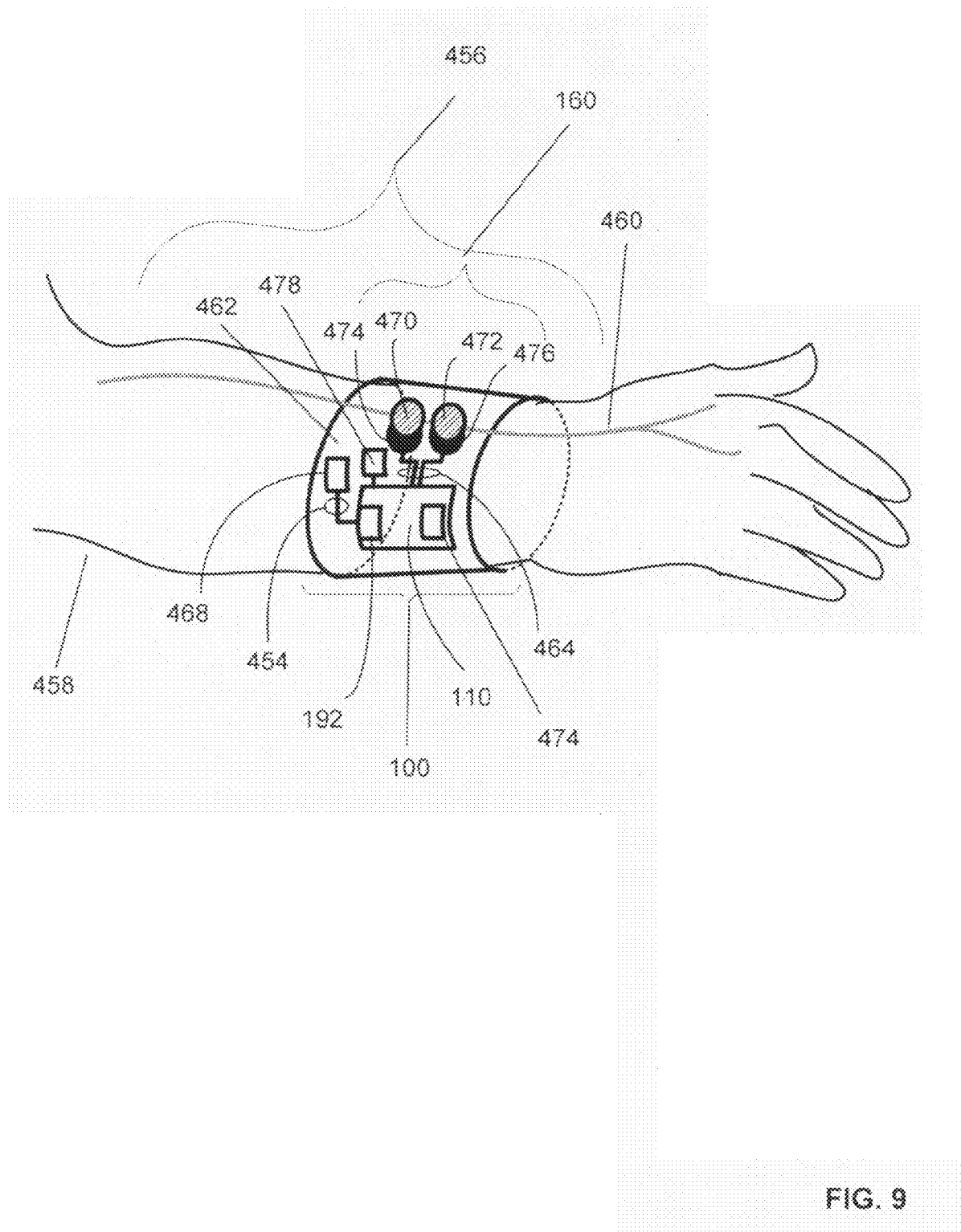
FIG. 9 is an illustration of an embodiment of a system in which a chemical blocking agent source is located in an arm band.

FIG. 9 illustrates an embodiment of a system in which a chemical blocking agent source 160 is located in an arm band (or bracelet/cuff) 462 configured to be worn on a forearm 456 of a subject. Neural modulation system 100 includes a signal input structure 192 configured to receive a signal 454 indicative of an activity state of at least a portion 456 (in this case, the forearm) of a body of a subject 458 innervated by a peripheral neural structure 460. Neural modulation system 100 includes signal processing portion 110 configured to distinguish a first activity state of the at least a portion 456 of the body of the subject 458 innervated by the peripheral neural structure 460 from a second activity state of the at least a portion 456 of the body of the subject 458 innervated by the peripheral neural structure 460 from the signal 454 received at the signal input structure 192 and generate a chemical blocking agent control signal 464 for driving delivery of a chemical blocking agent adapted to reversibly block conduction in the peripheral neural structure 460 of the subject during at least a portion of the first activity state. Neural modulation system 100 also includes chemical blocking agent source 160 configured to be worn on the body of the subject 458 and to deliver a chemical blocking agent responsive to the chemical blocking agent control signal 464. Signal 454 may be produced by sensor 468 in response to activity of portion 456 of body of subject 458. Sensor 468 may be, for example, an electrode for sensing electromyographic (EMG) activity reflective of muscle activity.

In the example of FIG. 9, chemical blocking agent source 160 includes an iontophoresis system that includes two electrodes, anode 470 and cathode 472, with associated reservoirs 474 and 476 of chemical blocking agent and electrolyte, respectively. The device may be powered by battery 478.

In other embodiments, a chemical blocking agent source may be located in or on a wrap adapted to be positioned around at least a portion of the body of the subject; in or on a bandage or patch configured to be adhered or secured to at least a portion of skin, tissue or mucous membrane of the subject; in or on a bracelet, anklet, or cuff configured to be worn on a limb of the subject (e.g. as shown in FIG. 9); in or on a collar or necklace configured to be worn on a neck of the subject; or in or on a fitted garment or item of clothing configured to be worn by the subject. In some embodiments, the signal processing portion may be configured to be worn on the body of the subject. The signal processing portion may be packaged with the chemical blocking agent source in a package configured to be worn on the body of the subject, e.g. as shown in FIG. 9. In other embodiments, the signal processing portion may be configured to be located at a location remote from the body of the subject.

Iontophoresis, as employed in the system of FIG. 9, uses low voltage electrical current to drive ionized agents or drugs across the skin. Electric current flows from an anode to a cathode with the skin completing the circuit, and drives ionized molecules into the skin from a reservoir associated with a transdermal delivery device. Other transdermal delivery methods include, for example, electroporation and phonophoresis or sonophoresis.

Electroporation uses short, high voltage, electrical pulses to create transient aqueous pores in the skin through which an agent or drug may be transported. Phonophoresis or sonophoresis uses low frequency ultrasonic energy to disrupt the stratum corneum. For example, Saliba et al. describe enhanced systemic levels of topical dexamethasone when applied in combination with ultrasound pulsed with an intensity of 1.0 W/cm$^2$ at a frequency of 3-MHz for 5 minutes (Saliba, S., Mistry, D. J., Perrin, D. H., Gieck, J., and Weltman, A. "Phonophoresis and the absorption of dexamethasone in the presence of an occlusive dressing." J. Athletic Training. 2007 Vol.43, No. 3, pp. 349-354, which is incorporated herein by reference in its entirety). Thermal energy may be used to facilitate transdermal delivery by making the skin more permeable and by increasing the energy of drug molecules.

In some instances, transdermal delivery of a chemical blocking agent may be facilitated using microporation induced by an array of microneedles. When applied to the skin, microneedles painlessly create micropores in the stratum corneum without causing bleeding and lower the resistance to drug diffusion through the skin. In some cases, microneedles may be used to abrade or ablate the skin prior to transport of an agent or drug. For example, a micro-array of heated hollow posts may be used to thermally ablate human skin in preparation for transdermal drug delivery by diffusion as described in U.S. Published Patent Application 2008/0045879, which is incorporated herein by reference in its entirety. Alternatively, an array of microneedles may be designed to actively inject drug into the skin as described in Roxhed, N., Samel, B., Nordquist, L., Griss, P., and Stemme, G. "Painless drug delivery through microneedle-based transdermal patches featuring active infusion." IEEE Transactions on Biomedical Engineering, 2008, Vol. 55, No, 3, pp. 1063-1071, which is incorporated herein by reference in its entirety.

Transdermal delivery of a chemical blocking agent facilitated by an energy source may be combined with a method that perforates or abrades the skin of a subject. For example, a transdermal delivery method may combine iontophoresis with the use of one or more microprojections to perforate the skin to enhance penetration and delivery of an agent, as described, for example, in U.S. Pat. No. 6,835,184 and U.S. Published Patent Application 2006/0036209, which are incorporated herein by reference in their entirety. In another example, an energy source as used in iontophoresis or electroporation may be combined with electrically-induced ablation of skin cells as described in U.S. Pat. No. 7,113,821, which is incorporated herein by reference in its entirety.

Delivery of a chemical blocking agent via transdermal methods may be controlled in a number of ways. Delivery may be performed completely automatically with a preset dosage regime, controlled by the subject or other individual (e.g., a medical caregiver), or controlled automatically by a feedback controller based on the sensed activity state of the subject. A preset dosage regime may assume active and inactive states of the subject such as, for example, during the daytime versus the nighttime and as such deliver drug only during the night when the subject is sleeping. A transdermal delivery system may automatically time the activation and deactivation of an electrical power supply, for example, for delivery and cessation of delivery of a drug at a variable controlled rate at preset or preprogrammed time intervals as described in U.S. Pat. No. 5,224,928, which is incorporated herein by reference in its entirety. The pre-set dosage regime may be programmed into the transdermal delivery method at the time of manufacture, and/or programmed or reprogrammed subsequent to manufacture one or more times. In some embodiments, the transdermal delivery method may have a removable computer interface component that can be externally programmed for a specific drug delivery regime and reinserted into the device, as described in U.S. Pat. No. 6,539,250, which is incorporated herein by reference in its entirety.

Figure 10:
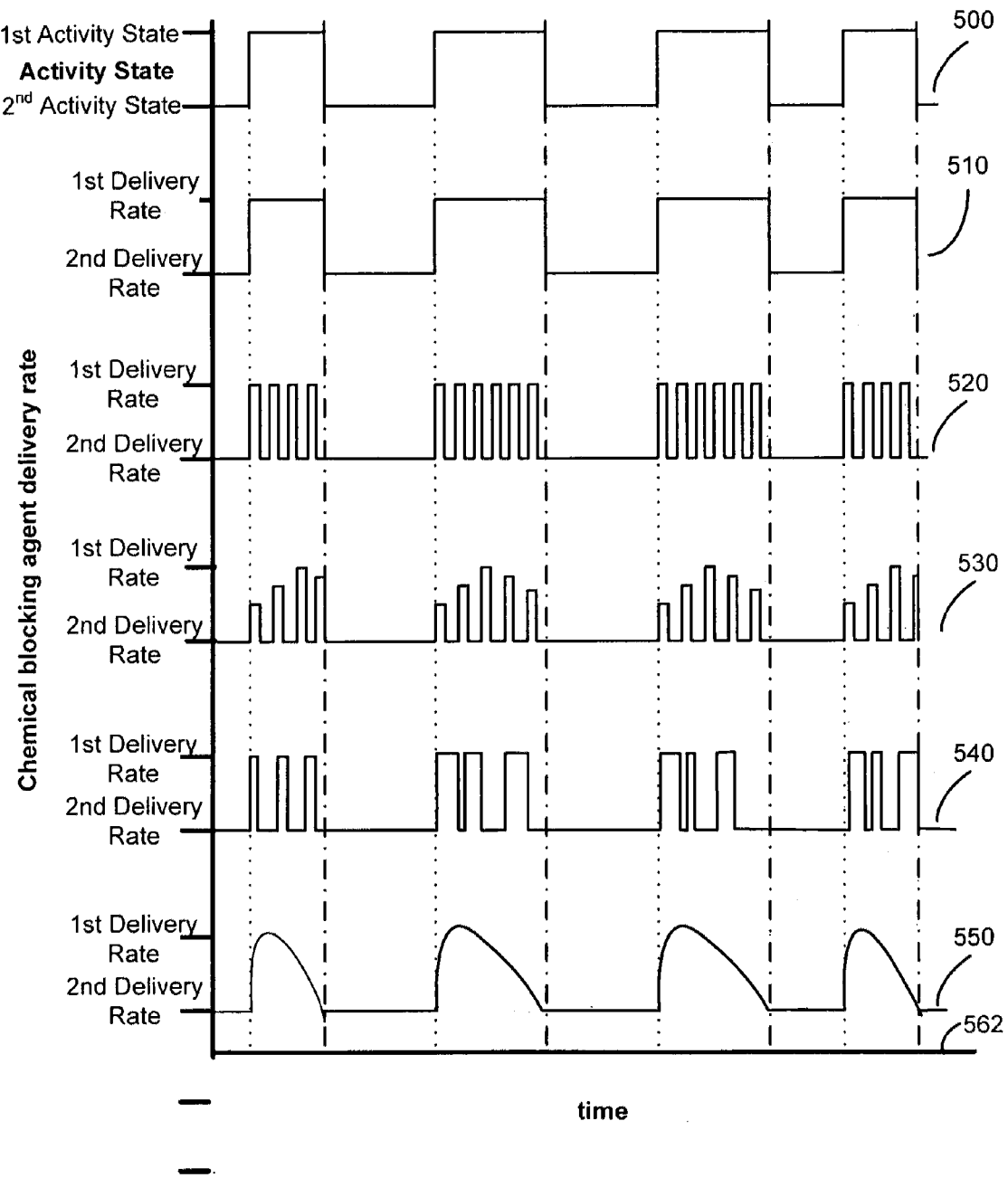
FIG. 10 is an illustration of types of blocking stimuli.

FIG. 10 illustrates a number of patterns of chemical blocking agent delivery. Trace 500 represents the activity state of a subject as a function of time, as indicated on axis 562. Trace 510 depicts an example of a chemical blocking agent that is delivered substantially continuously during each blocking period, with the blocking periods corresponding to occurrences of a first activity state, as indicated in trace 500.

In other embodiments, a chemical blocking agent sufficient to produce a reversible conduction block of at least a portion of a peripheral neural structure of a subject may be delivered intermittently in pulses during the blocking period. For example, a chemical blocking agent sufficient to produce a reversible conduction block of at least a portion of a peripheral neural structure of a subject may be delivered intermittently in pulses at a fixed repetition rate during the blocking period. Traces 520 and 530 in FIG. 10 are two examples of blocking stimuli delivered intermittently during the blocking period. In trace 530, rate of delivery of a chemical blocking agent during each pulse varies over time during the blocking period. In trace 540, duration of pulses of chemical blocking agent delivery and intervals between pulses vary over time during the blocking period. In some embodiments, the chemical blocking agent may be delivered according to a programmed pattern during at least a portion of the blocking period. The programmed pattern may specify a chemical blocking agent delivery rate that varies over time during the blocking period, as depicted in trace 550. In addition, a programmed pattern may specify rate of delivery of chemical blocking agent during pulses delivered intermittently during the blocking period, in which the amplitude of the stimulus pulses varies over time during the blocking period, as illustrated in trace 530, or in which one or both of the duration of the stimulus pulses or interval between the stimulus pulses varies over time during the blocking period, as illustrated in trace 540.

Various chemical blocking agents may be used to block nerve conduction. Examples of nerve blocking agents include local anesthetics (e.g. amino esters such as benzocaine, chloroprocaine, cocaine, cyclomethycaine, dimethocaine, procaine, proparacaine, propoxycaine, and tetracaine, and amino amides such as articaine, bupivacaine, carticaine, cinchocaine/dibucaine, etidocaine, levobupivacaine, lidocaine/lignocaine, mepivacaine, prilocaine, ropivacaine, and trimecaine), tricyclic antidepressants (e.g. amitriptyline, butriptyline, amoxapine, clomipramine, desipramine, dosulepin hydrochloride, doxepin, imipramine, iprindole, lofepramine, nortriptyline, opipramol, protryptyline, and trimipramine), neurotoxins (e.g. tetrodotoxin, saxitoxin, Botulinum toxin), or any other agent that blocks nerve conduction. See "Local anaesthetics and nerve conduction;" The Virtual Anaesthesia Textbook; http://www.virtual-anaesthesia-textbook.com; which is incorporated herein by reference in its entirety. Further examples of chemical blocking agents include anticholinergics, including muscarinic receptor antagonists (e.g. belladonna alkaloids such as atropine (hyoscyamine) and scopolamine (hyoscine), and or synthetic and semisynthetic substances such as darifenacin, dicyclomine, flavoxate, ipratropium, oxybutynin, pirenzepine, solifenacin, tiotropium, tolterodine, tropicamide, and trospium) and nicotinic receptor antagonists (e.g., ganglionic blocking agents such as mecamylamine and trimethaphan; nondepolarizing neuromuscular blocking agents such as atracurium, cisatracurium, doxacurium, metocurine, mivacurium, pancuronium, pipecuronium, rocuronium, tubocurarine, or vecuronium; or depolarizing neuromuscular blocking agents such as gallamine and succinylcholine). Chemical blocking agents may also include β-adrenergic receptor antagonists (beta blockers), including non-selective agents (e.g., alprenolol, carteolol, levobunolol, mepindolol, metipranolol, nadolol, oxprenolol, penbutolol, pindolol, propranolol, sotalol, or timolol), β1-selective agents (e.g., acebutolol, atenolol, betaxolol, bisoprolol, celiprolol, esmolol, metoprolol, or nebivolol), mixed α1/β-adrenergic antagonists (e.g., carvedilol, celiprolol, or labetalol), or β2-selective agents (e.g. butaxamine). Still other chemical blocking agents include analgesics, such as paracetamol, NSAIDs (non-steroidal anti-inflammatory drugs), COX-2 (cyclooxygenase-2) inhibitors, and opiates and morphinomimetics such as morphine, hydromorphone, oxymorphone, diamorphine, diacetylmorphine, methadone, fentanyl, sulfentanil, alfentanil, remifentanil, meperidine, levorphanol, codeine, oxycodone, dihydrocodeine, hydrocodone, and pethidine. Still other chemical agents may include benzodiazepines, e.g., alprazolam, bromazepam, chlordiazepoxide, clonazepam, diazepam, estazolam, flunitrazepam, flurazepam, lorazepam, lormetazepam, mexazolam, midazolam, nitrazepam, oxazepam, temazepam, or triazolam. Aside from the main neurotransmitters of the peripheral nervous system, acetylcholine and noradrenaline, other neurotransmitters exist, jointly labeled non-noradrenergic, non-cholinergic (NANC) transmitters, and drugs that alter their effects may also be used as chemical agents to block neural activity. Examples of such transmitters include non-peptides (e.g., adenosine triphosphate, gamma-amino butyric acid, dopamine, or nitric oxide), and peptides (e.g., neuropeptide Y, vasoactive intestinal peptide, gonadotropin releasing hormone, substance P and calcitonin gene-related peptide). Modulators of potassium channels, neurokinin (NK) receptors, and purinergic receptors may also be of use as chemical blocking agents.

A chemical blocking agent for delivery by a transdermal and/or implantable device may be formulated alone or in combination with one or more pharmaceutically acceptable carriers, diluents, excipients, and/or vehicles such as, for example, buffers, surfactants, preservatives, solubilizing agents, isotonicity agents, and stabilizing agents as appropriate. A "pharmaceutically acceptable" carrier, for example, may be approved by a regulatory agency of the state and/or Federal government such as, for example, the United States Food and Drug Administration (US FDA) or listed in the U.S. Pharmacopeia or other generally recognized pharmacopeia for use in animals, and more particularly in humans. Conventional formulation techniques generally known to practitioners are described in Remington: The Science and Practice of Pharmacy, 20$^{th}$ Edition, Lippincott Williams & White, Baltimore, Md. (2000), which is incorporated herein by reference in its entirety.

Acceptable pharmaceutical carriers include, but are not limited to, the following: sugars, such as lactose, glucose and sucrose; starches, such as corn starch and potato starch; cellulose and its derivatives, such as sodium carboxymethyl cellulose, ethyl cellulose, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions.

The chemical blocking agent may be formulated in a pharmaceutically acceptable liquid carrier. The liquid carrier or vehicle may be a solvent or liquid dispersion medium comprising, for example, water, saline solution, ethanol, a polyol, vegetable oils, nontoxic glyceryl esters, and suitable mixtures thereof. The solubility of a chemical blocking agent may be enhanced using solubility enhancers such as, for example, water; diols, such as propylene glycol and glycerol; monoalcohols, such as ethanol, propanol, and higher alcohols; DMSO (dimethylsulfoxide); dimethylformamide, N,N-dimethylacetamide; 2-pyrrolidone, N-(2-hydroxyethyl)pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones). The proper fluidity may be maintained, for example, by the formation of liposomes, by the maintenance of the required particle size in the case of dispersions or by the use of surfactants. One or more antimicrobial agent may be included in the formulation such as, for example, parabens, chlorobutanol, phenol, sorbic acid, and/or thimerosal to prevent microbial contamination. In some instances, it may be preferable to include isotonic agents such as, for example, sugars, buffers, sodium chloride or combinations thereof.

A chemical blocking agent for use in a transdermal delivery method may be formulated to enhance transit of the agent through the skin. For example, water-insoluble, stratum corneum-lipid modifiers such as for example 1,3-dioxanes, 1,3-dioxolanes and derivatives thereof, 5-, 6-, 7-, or 8-numbered lactams (e.g., butyrolactam, caprolactam), morpholine, cycloalkylene carbonate have been described for use in transdermal iontophoresis (see, e.g., U.S. Pat. No. 5,527,797, which is incorporated herein by reference in its entirety). Other lipid bilayer disrupters include but are not limited to ethanol, polyethylene glycol monolaurate, azacycloalkan-2-ones, linoleic acid, capric acid, lauric acid, neodecanoic acid (in ethanol or propylene glycol, for example).

In some instances, the chemical blocking agent may be formulated in a dispersed or dissolved form in a hydrogel or polymer associated with either an implantable or a transdermal delivery method. Examples of hydrogels and/or polymers include but are not limited to gelled and/or cross-linked water swellable polyolefins, polycarbonates, polyesters, polyamides, polyethers, polyepoxides and polyurethanes such as, for example, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Other suitable polymers include but are not limited to cellulose ethers, methyl cellulose ethers, cellulose and hydroxylated cellulose, methyl cellulose and hydroxylated methyl cellulose, gums such as guar, locust, karaya, xanthan gelatin, and derivatives thereof. For iontophoresis, for example, the polymer or polymers may include an ionizable group such as, for example, (alkyl, aryl or aralkyl) carboxylic, phosphoric, glycolic or sulfonic acids, (alkyl, aryl or aralkyl)

quaternary ammonium salts and protonated amines and/or other positively charged species as described in U.S. Pat. No. 5,558,633, which is incorporated herein by reference in its entirety.

Information regarding formulation of FDA approved chemical blocking agents may be found in the package insert and labeling documentation associated with each approved agent. A compendium of package inserts and FDA approved labeling may be found in the Physicians Desk Reference. Alternatively, formulation information for approved chemical blocking agents may be found on the internet at websites such as, for example, www.drugs.com and www.rxlist.com. For example, the liquid form of diazepam (Valium) contains active drug, benzyl alcohol as preservative, propylene glycol, ethanol, and is buffered with sodium benzoate and benzoic acid and the pH adjusted with sodium hydroxide. For those chemical blocking agents which do not currently have a formulation appropriate for use in an implanted device, an appropriate formulation may be determined empirically and/or experimentally using standard practices.

As an alternative to systems as illustrated in FIG. 9, in which a chemical blocking agent source is worn on the body of the subject, in other embodiments, a reversible conduction block may be produced in a peripheral neural structure of a subject with a chemical blocking agent source configured to be positioned beneath at least a portion of the body of the subject. For example, in various embodiments, the chemical blocking agent source may be located in or on a chair, bed, pad, cushion, or any other structure on which at least a portion of the body of the subject may rest. If only a portion of the subject's body is to be subjected to the chemical blocking agent, a structure having a size and structure suited to the portion of the body may be used. For example, if the body portion is the lower leg, the chemical blocking agent source may be included in a footstool, for example. If the body portion is the arm, the chemical blocking agent source may be included in a table top, arm rest, or sling. If the chemical blocking agent source is included in a pad or cushion of an appropriate size, the pad or cushion may be placed on any surface (a chair, stool, table top, the subject's lap, a bed, the ground, etc.) and the body portion may then be positioned above the pad or cushion.

For transdermal delivery methods as disclosed herein, close contact of at least a portion of the delivery device with the skin (sufficient for transmission of e.g., chemicals or electrical, magnetic, thermal, acoustic or other forms of energy) may be provided by placing the portion of the delivery device against bare skin, or by providing portions of the delivery device (e.g., needles or microneedles) that are capable of penetrating a layer of clothing or bedding interposed between the delivery device and the skin of the subject.

Figure 11B:
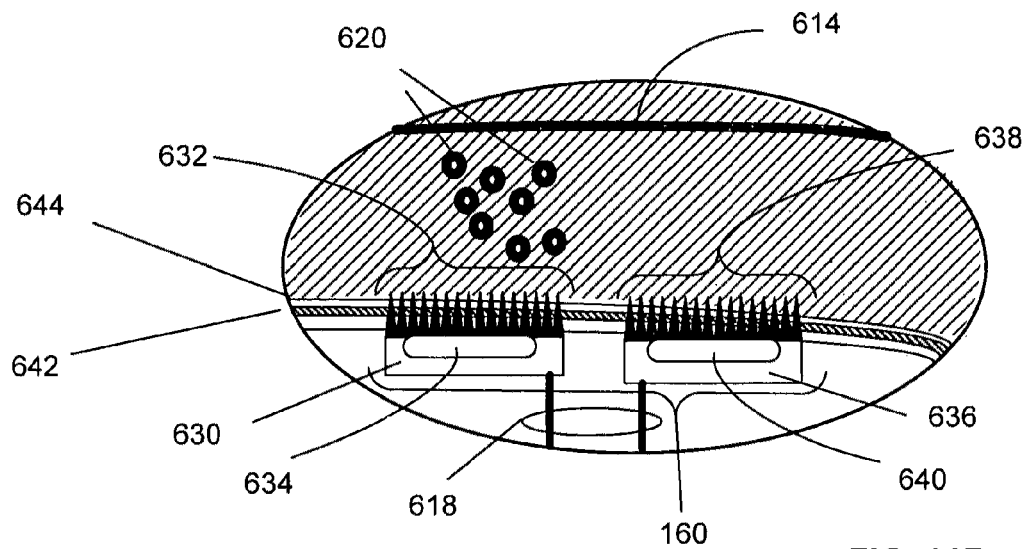
FIG. 11B is a detail view of a portion of the system of FIG. 11A.
Figure 11A:
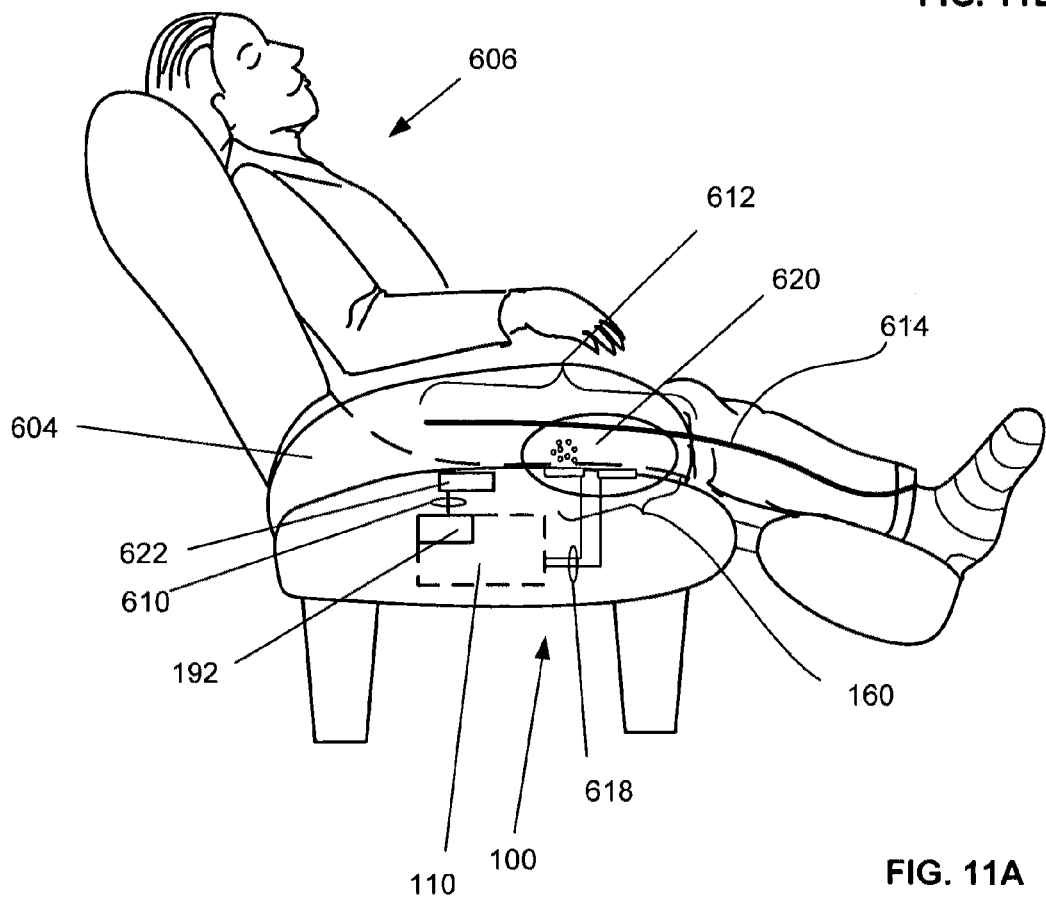
FIG. 11A is an illustration of an embodiment of a system in which a chemical blocking agent source is located in chair.

FIG. 11A depicts an embodiment of a neural modulation system 100 in which a chemical blocking agent source 160 is located in chair 604 on which the subject 606 may be seated. In the embodiment of FIG. 11A, neural modulation system 100 includes a signal input structure 192 configured to receive a signal 610 indicative of an activity state of at least a portion 612 of a body of a subject 606 (in this example, a portion of the leg of subject 606) innervated by a peripheral neural structure 614. Neural modulation system 100 may also include a signal processing portion 110 configured to distinguish a first activity state of the at least a portion 612 of the body of the subject 606 innervated by the peripheral neural structure 614 from a second activity state of the at least a portion 612 of the body of the subject 606 innervated by the peripheral neural structure 614 from the signal 610 received at the signal input structure 192, and generate a chemical blocking agent control signal 618 for driving delivery of a chemical blocking agent 620. Chemical blocking agent may reversibly block conduction in the peripheral neural structure 614 of the subject during at least a portion of the first activity state. As shown in FIG. 11A, and in greater detail in the expanded view of FIG. 11B, chemical blocking agent source 160 may be configured to be positioned beneath at least a portion 612 of the body of the subject 606 and to deliver a chemical blocking agent 620 responsive to the chemical blocking agent control signal 618. Chemical blocking agent source 160 may include anode 630, with associated microneedle array 632 and chemical blocking agent reservoir 634, and cathode 636, with associated microneedle array 638 and electrolyte reservoir 640. Microneedles in microneedle arrays 632 and 638 pass through clothing 642 and stratum corneum 644 to permit delivery of chemical blocking agent 620 to subject 606. Chemical blocking agent source 160 may be configured to be located in or on a chair 604, as depicted in FIG. 11.

Figure 12A:
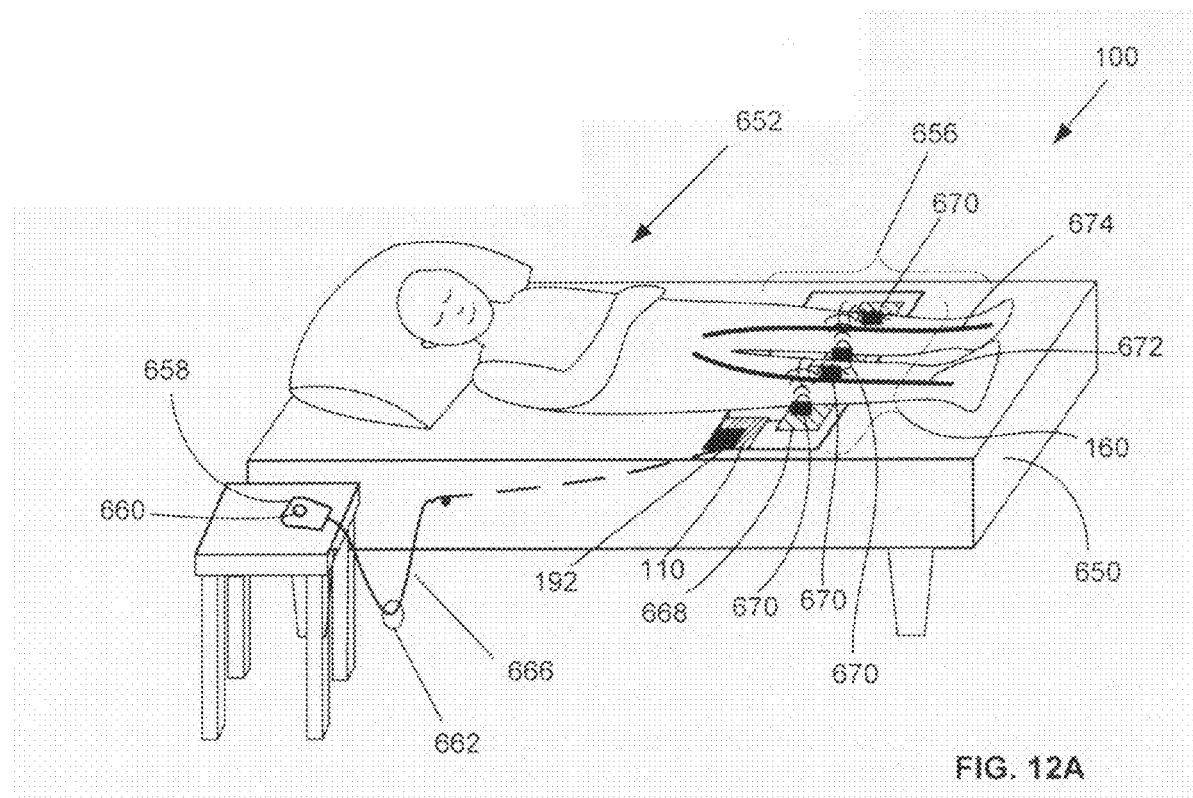
FIG. 12A is an illustration of an embodiment of a system in which a chemical blocking agent source is located in a bed.
Figure 12B:
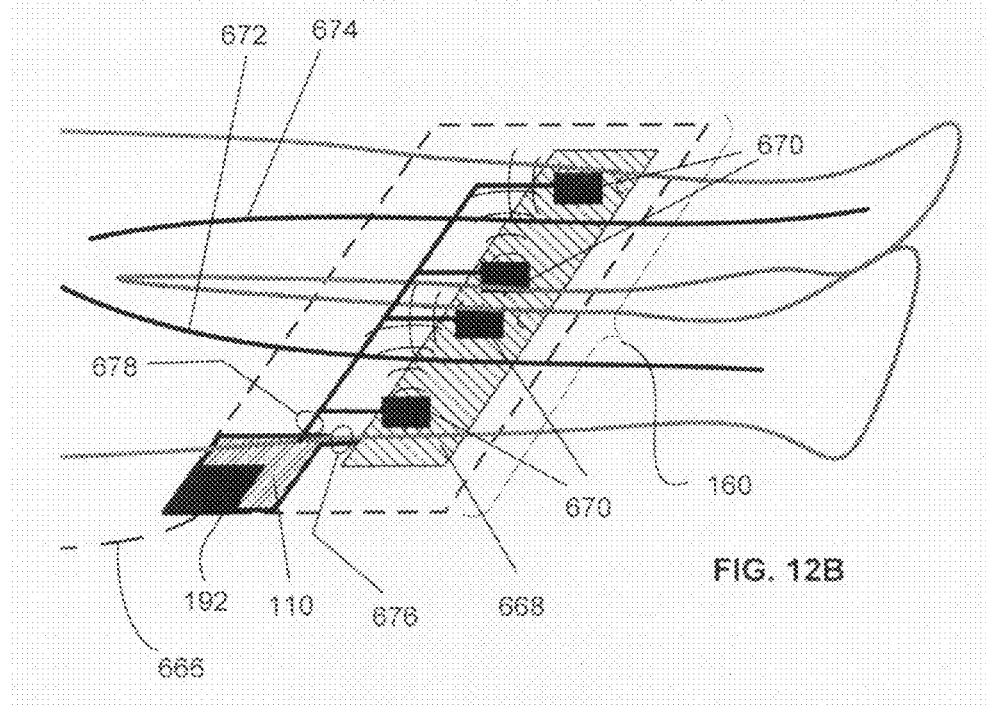
FIG. 12B is a close-up view of a portion of FIG. 12A.

FIG. 12A depicts an embodiment of a neural modulation system 100 in which a chemical blocking agent source 160 is located in a bed 650 upon which the subject 652 lies. FIG. 12B shows a portion of the system of FIG. 12A in greater detail. In the embodiment of FIGS. 12A and 12B, a subject 652 rests on a bed 650. Chemical blocking agent source 160 is positioned below a portion 656 of the body of subject 652. In the present example, chemical blocking agent source 160 includes pad 668 impregnated with chemical blocking agent. Multiple ultrasound transducers 670 serve to cause movement of chemical blocking agent through the skin of subject 652. Ultrasound transducers 670 may be aimed and focused so that acoustic pulses produce constructive interference to maximize acoustic energy at the areas of overlap. The general approach used in the system of FIGS. 12A and 12B is described in Saliba, S., Mistry, D. J., Perrin, D. H., Gieck, J., and Weltman, A. "Phonophoresis and the absorption of dexamethasone in the presence of an occlusive dressing." J. Athletic Training. 2007 Vol.43, No. 3, pp. 349-354, which is incorporated herein by reference in its entirety.

User input device 658 (in this example, a switch device including a push-button 660 that may be depressed by subject 652 to indicate the beginning and end of a rest period) provides a signal 662 to signal processing portion 110 on cable 666, via signal input structure 192, representing the activity state of the subject. As described in connection with other embodiments, signal processing portion 110 controls delivery of a chemical blocking agent by chemical blocking agent source 160.

As an alternative to transdermal delivery, in some embodiments a reversible conduction block may be produced in a peripheral neural structure of a subject with a chemical blocking agent source implanted within the body of the subject. An implantable chemical blocking agent source has been shown in schematic form in FIG. 4. Implantable devices may include, but are not limited to, polymeric structures, infusion pumps, or MEMS devices, or various other implantable delivery devices as are known to those of skill in the art. Implantable devices may be used to deliver chemical blocking agents systemically or locally to a specific site of action.

Figure 13:
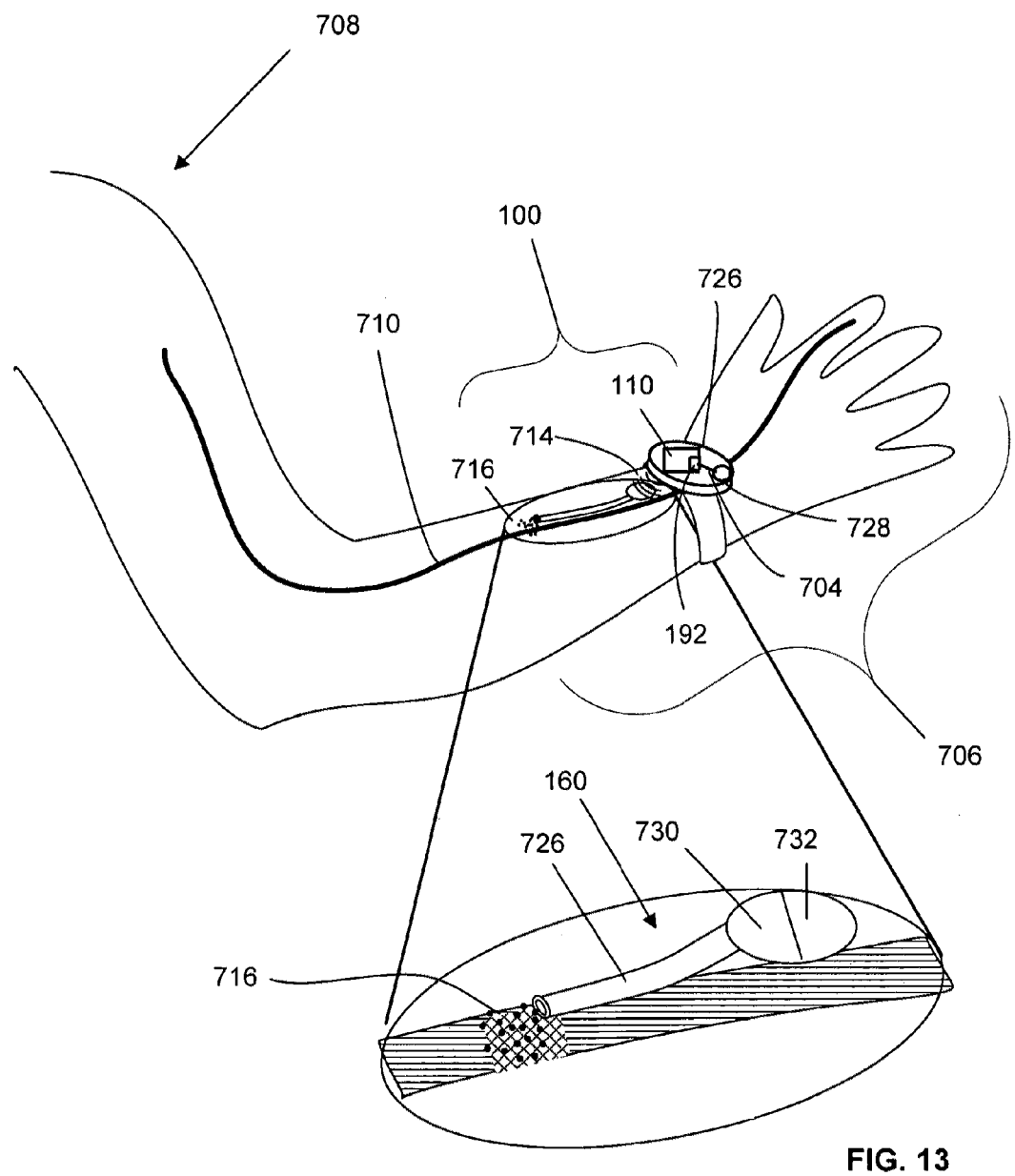
FIG. 13 is an illustration of an embodiment of a system in which a chemical blocking agent source is implanted within the body of a subject.

A chemical blocking agent may be delivered using an implantable delivery device that includes an infusion pump that actively moves the chemical blocking agent from an associated reservoir into a subject. FIG. 13 depicts an embodiment of a neural modulation system 100 in which a chemical blocking agent source 160 is implanted within the body of the subject 708, while signal processing portion 110 is located external to the body of the subject 708. Neural modulation system 100 as depicted in FIG. 13 includes signal input structure 192 configured to receive a signal 704 indicative of an activity state of at least a portion 706 of a body of a subject 708 innervated by a peripheral neural structure 710. Signal processing portion 110 is configured to distinguish a first activity state of the at least a portion 706 of the body of the subject 708 innervated by the peripheral neural structure 710 from a second activity state of the at least a portion 706 of the body of the subject 708 innervated by the peripheral neural structure 710 from signal 704 received at the signal input structure 192, and generate a chemical blocking agent control signal 714 for driving delivery of a chemical blocking agent 716, to reversibly block conduction in the peripheral neural structure 710 of subject 708 during at least a portion of the first activity state, and chemical blocking agent source 718. Chemical blocking agent source 718 is configured to be implanted within the body of the subject 708 and to deliver a chemical blocking agent 716 responsive to the chemical blocking agent control signal 714. In this example, chemical blocking agent source 718 includes reservoir 730 containing chemical blocking agent 716 and pump 732, which pumps chemical blocking agent 716 through cannula 734 to the vicinity of peripheral neural structure 710 (here, a nerve) under the control of chemical blocking agent control signal 714. Pump 732 may be driven by a power source within or external to the body of the subject, via a wired or wireless connection (see, e.g. US 2006/0190053, which is incorporated herein by reference in its entirety).

A variety of types of pumps may be incorporated into an implantable delivery systems such as, for example, a piston pump, rotary vane pump, osmotic pump, Micro Electro Mechanical Systems (MEMS) pump, diaphragm pump, peristaltic pump, or solenoid piston pump. For example, the infusion pump may be a vapor-pressure powered pump in which a fluorocarbon charging fluid such as freon is used to drive the pump as a vapor-liquid mixture at normal body temperature and atmospheric pressure. Alternatively, the infusion pump may be a battery powered peristaltic pump. The latter is exemplified by an intrathecal drug delivery device in which an infusion pump with a controllable receiver unit is implanted under skin and a catheter is fed into the target site, in this case the spine (see, e.g., Belverud, S., Mogilner, A., Schulder, M. "Intrathecal Pumps." Neurotherapeutics. 2008 Vol. 5, No. 1., pp. 114-122, which is incorporated herein by reference in its entirety). The reservoir associated with the pump may be refillable via percutaneous injection. An external controller may be used to wirelessly control the pump.

In some cases, methods of modulating neural activity as described herein, and as outlined, e.g. in FIG. 5, the step of producing a reversible conduction block in a peripheral neural structure of a subject with a chemical blocking agent while the subject is in a first activity state may include delivering the chemical blocking agent in an inactive form non-specifically relative to the peripheral neural structure and delivering an activating energy to the peripheral neural structure or vicinity thereof to convert the chemical blocking agent from the inactive form to an inactive form. That is, the inactive form of the chemical blocking agent may be delivered systemically by various methods, as known to those of ordinary skill in the art, or the inactive form may be delivering a portion of the body of the subject that includes the peripheral neural structure, but not in a finely targeted manner. Various types of activating energy may be delivered in a targeted fashion, including but not limited to thermal energy, acoustic energy, electromagnetic energy, optical energy, and applied electrical field, or an applied magnetic field.

External control of an implantable delivery device may be mediated by remote control through an electromagnetic wireless signal such as, for example, infrared or radio waves that are able to trigger an electrical stimulus within the implanted device. Examples of remote control drug delivery devices are described in U.S. Pat. Nos. 5,928,195; 6,454,759; and 6,551,235, which are incorporated herein by reference in their entirety. Delivery of a chemical blocking agent may be initiated in response to an "on" trigger and stopped in response to an "off" trigger, for example. Alternatively, a chemical blocking agent may be delivered as a microbolus, for example, in response to an "on" trigger as described in U.S. Pat. No. 6,554,822, which is incorporated herein by reference in its entirety. External control may be initiated by a caregiver. In some cases, a subject may initiate delivery of the chemical blocking agent. As such, the system may have a built in mechanism to limit the number of allowable doses by a subject and/or caregiver in a given time frame as described, for example, in U.S. Pat. No. 6,796,956, which is incorporated herein by reference in its entirety.

In the example of FIG. 13, chemical blocking agent source 716 is implanted, but the neural modulation system 100 includes an external portion 726, which may be worn on the wrist in a manner similar to a wristwatch. In the embodiment of FIG. 13, external portion 726 includes signal processing portion 110 and sensor 728, a motion sensor which detects movement of portion 706 of the body of subject 708, and generates signal 704, which is provided to signal input structure 192, as discussed above.

Figure 14:
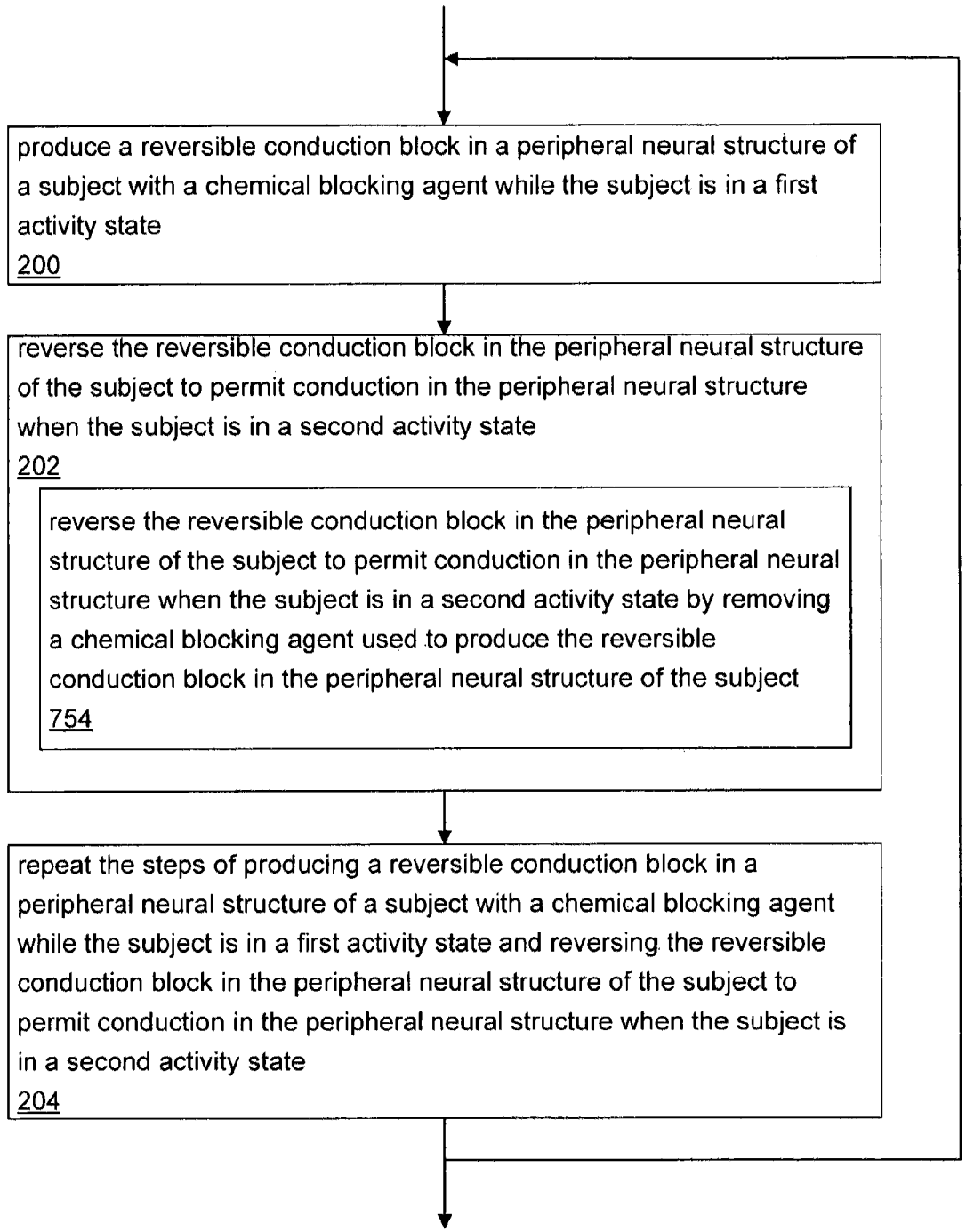
FIG. 14 is a flow diagram of a method of modulating neural activity.

FIG. 14 depicts a related method, which includes the steps of producing a reversible conduction block in a peripheral neural structure of a subject with a chemical blocking agent while the subject is in a first activity state at 200; reversing the reversible conduction block in the peripheral neural structure of the subject to permit conduction in the peripheral neural structure when the subject is in a second activity state at 202; wherein the method further includes reversing the reversible conduction block in the peripheral neural structure of the subject to permit conduction in the peripheral neural structure when the subject is in a second activity state by removing a chemical blocking agent used to produce the reversible conduction block in the peripheral neural structure of the subject, as indicated at 754; and repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state, as indicated at 204.

In the method of FIG. 14, chemical blocking agent is removed. A chemical blocking agent may be removed by discontinuing delivery of chemical blocking agent and permitting the chemical blocking agent to be removed through a naturally occurring process within the body of the subject (i.e., by permitting the concentration of chemical blocking agent at the peripheral neural structure to decrease through naturally occurring processes), e.g. by degradation or metabolism of the chemical blocking agent, dispersal, diffusion, or transport of the chemical blocking agent away from the peripheral neural structure that is to be blocked, or uptake or binding of the chemical blocking agent by tissue. Alternatively, the chemical blocking agent may be removed by a further intervention or action, typically by the introduction of a material (chemical compound or mixture) or energy (including but not limited to light, heat, acoustic energy, electromagnetic radiation, an electrical field, a magnetic field) to the peripheral neural structure or vicinity that causes or influences modification, degradation, metabolism, dispersal, diffusion, transport, uptake, or binding of the chemical blocking agent so that it is no longer effective or available to produce blocking of conduction in the peripheral neural structure. In some cases, the chemical blocking agent may be removed by removing energy from the peripheral neural structure or its vicinity (e.g., by cooling), rather than delivering energy to the peripheral neural structure or its vicinity. Removal of a chemical blocking agent by the introduction of material or energy may also be referred to as "reversal" of blocking and the introduced material or energy may be termed a "reversing stimulus."

Figure 15:
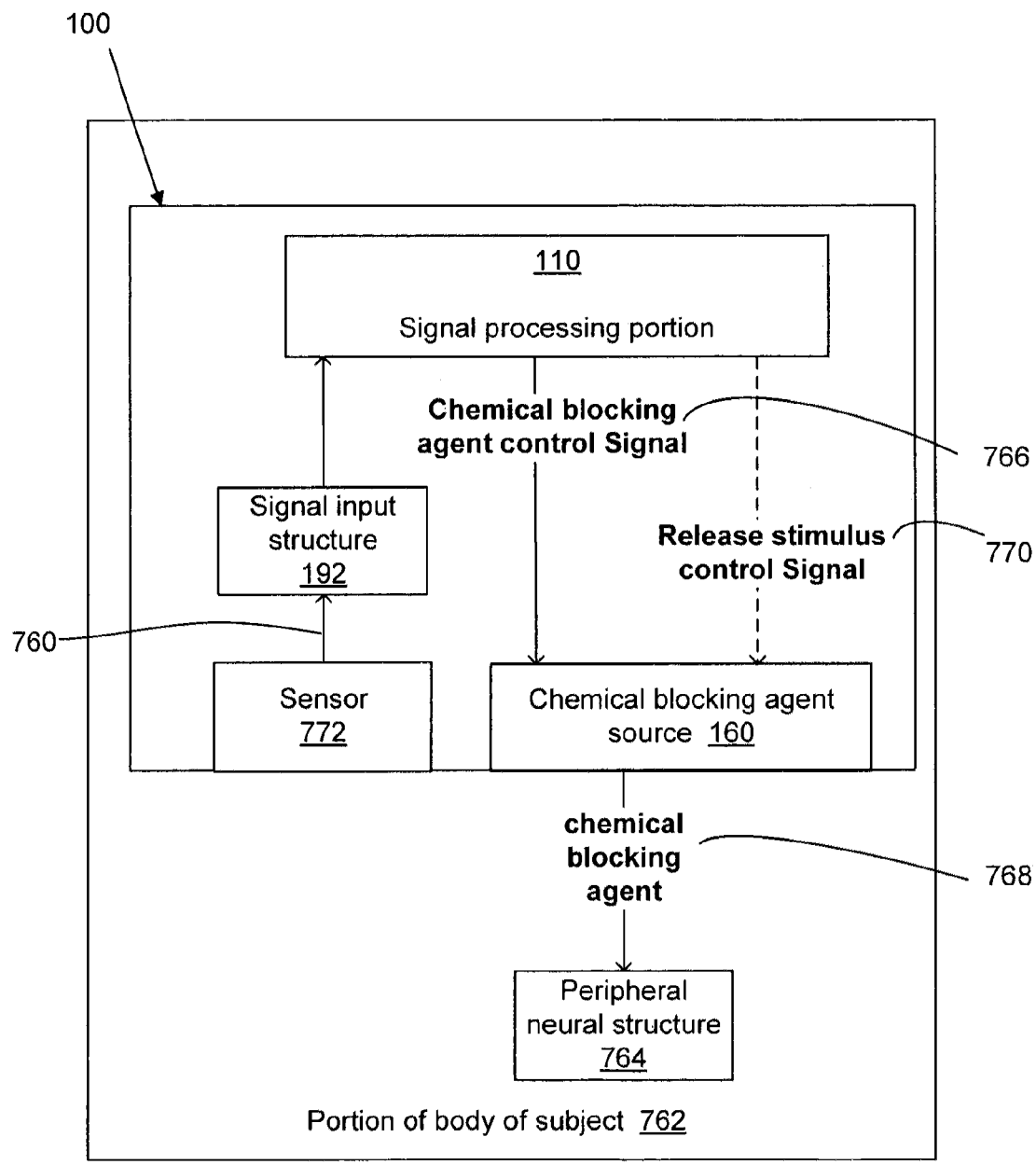
FIG. 15 is a block diagram of an example of a neural modulation system.

FIG. 15 illustrates a neural modulation system 100 that includes a signal input structure 192 configured to receive a signal 760 indicative of an activity state of at least a portion 762 of a body of a subject innervated by a peripheral neural structure 764. Neural modulation system 100 also includes a signal processing portion 110 configured to distinguish a first activity state of the at least a portion 762 of the body of the subject innervated by the peripheral neural structure 764 from a second activity state of the at least a portion 762 of the body of the subject innervated by the peripheral neural structure 764 from the signal 760 received at the signal input structure 192, and generate a chemical blocking agent control signal 766 for driving delivery of a chemical blocking agent 768 adapted to reversibly block conduction in the peripheral neural structure 764 of the subject during at least a portion of the first activity state. In some embodiments, as disclosed elsewhere herein, discontinuation of generation of chemical blocking agent control signal may stop release of chemical blocking agent 768. As indicated in FIG. 15, the signal processing portion may optionally generate a release stimulus control signal 770 for controlling discontinuation of delivery of the chemical blocking agent 768 when the subject is in the second activity state. Neural modulation system 100 further includes sensor 772, which is operatively connected to the signal input structure 192 and configured to generate the signal 760 indicative of an activity state of at least a portion 762 of a body of a subject innervated by a peripheral neural structure 764 responsive to an activity of the at least a portion 762 of the body of the subject, and a chemical blocking agent source 160 configured to deliver a chemical blocking agent 768 responsive to the chemical blocking agent control signal. A release stimulus control signal 770 may be delivered to the chemical blocking agent source 160 from the signal processing portion 110 on the same line or channel as the chemical blocking agent control signal 766, or it may be provided on a separate line or channel.

The signal processing portion may be configured to repetitively generate the chemical blocking agent control signal for driving delivery of a chemical blocking agent adapted to reversibly block conduction in the peripheral neural structure of the subject during at least a portion of the first activity state and the release stimulus control signal for controlling discontinuation of delivery of the chemical blocking agent when the subject is in the second activity state.

In some embodiments, the signal processing portion may be configured to repetitively generate the chemical blocking agent control signal for driving delivery of a chemical blocking agent adapted to reversibly block conduction in the peripheral neural structure of the subject during at least a portion of the first activity state and the release stimulus control signal for controlling discontinuation of delivery of the chemical blocking agent when the subject is in the second activity state over a period of time sufficient to produce modulation of an immune response in a region innervated by the peripheral neural structure. Modulation of immune response may be assessed according to methods as discussed elsewhere herein.

In some embodiments, the signal processing portion may be configured to generate the chemical blocking agent control signal for driving delivery of a chemical blocking agent adapted to reversibly block conduction in the peripheral neural structure of the subject during at least a portion of the first activity state and the release stimulus control signal for controlling discontinuation of delivery of the chemical blocking agent when the subject is in the second activity state cyclically, wherein each cycle includes a blocking period during which a chemical blocking agent sufficient to produce reversible conduction block in a peripheral neural structure of a subject is produced while the subject is in a first activity state and a release period during which no chemical blocking agent is delivered, e.g., as illustrated in FIG. 6.

The signal processing portion may be configured to generate the chemical blocking agent control signal for driving delivery of a chemical blocking agent adapted to reversibly block conduction in the peripheral neural structure of the subject during at least a portion of the first activity state and the release stimulus control signal for controlling discontinuation of delivery of the chemical blocking agent when the subject is in the second activity state cyclically at a rate of one cycle per day.

The signal processing portion may be configured to generate the chemical blocking agent control signal for driving delivery of a chemical blocking agent adapted to reversibly block conduction in the peripheral neural structure of the subject during at least a portion of the first activity state and generate the release stimulus control signal for controlling discontinuation of delivery of the chemical blocking agent when the subject is in the second activity state in alternation according to a pre-set schedule.

Repetitive or cyclical generation of blocking stimuli may be performed as described herein, under the control of software, hardware, or other electrical circuitry by methods known to those of skill in the art.

Figure 16:
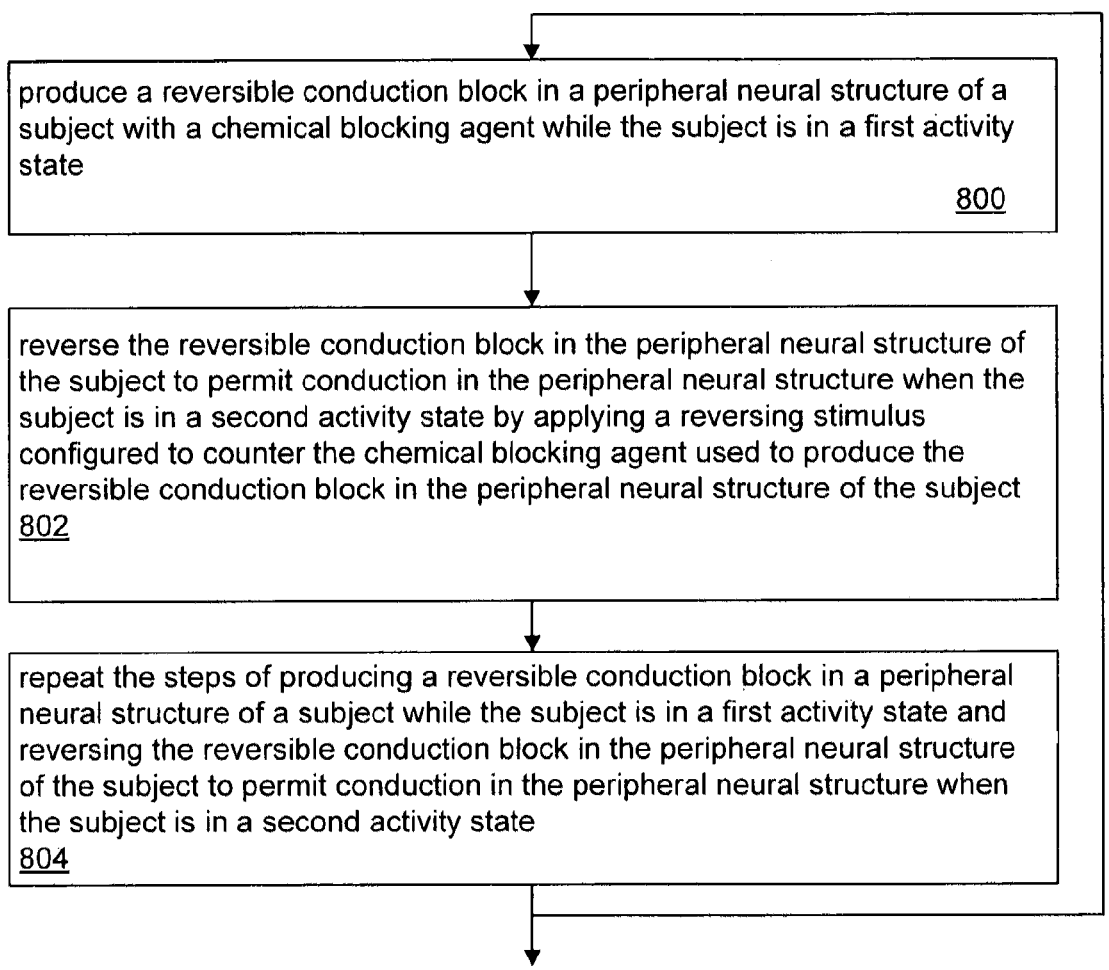
FIG. 16 is a flow diagram of a method of modulating neural activity.

As shown in FIG. 16, a method of modulating neural activity may include producing a reversible conduction block in a peripheral neural structure of a subject with a chemical blocking agent while the subject is in a first activity state (step 800), reversing the reversible conduction block in the peripheral neural structure of the subject to permit conduction in the peripheral neural structure when the subject is in a second activity state by applying a reversing stimulus configured to counter the chemical blocking agent used to produce the reversible conduction block in the peripheral neural structure of the subject (step 802), and repeating the steps of producing a reversible conduction block in a peripheral neural structure of a subject while the subject is in a first activity state and reversing the reversible conduction block in the peripheral neural structure of the subject to permit conduction in the peripheral neural structure when the subject is in a second activity state (step 804).

A reversing stimulus may be any stimulus sufficient to counter the chemical blocking agent and return the nerve to a normally conductive state. A reversing stimulus may be a chemical reversing agent or a reversing stimulus may be a non-chemical agent (e.g., an electrical field, a magnetic field, an acoustic stimulus, a thermal stimulus, or an electromagnetic stimulus). The reversing stimulus may cancel or oppose the effect of the chemical blocking agent. For example, chemical reversing agent may cause or influence modification, degradation, metabolism, dispersal, diffusion, transport, uptake, or binding of the chemical blocking agent to oppose the effect of the chemical blocking agent. The chemical reversing agent may reverse the effect of the chemical blocking agent by influencing the same or different cellular mechanisms as the chemical blocking agent, to restore or unblock conduction in the peripheral neural structure. A chemical reversing agent may be delivered with either the same chemical agent source as the chemical blocking agent, or with a different source.

Figure 17:
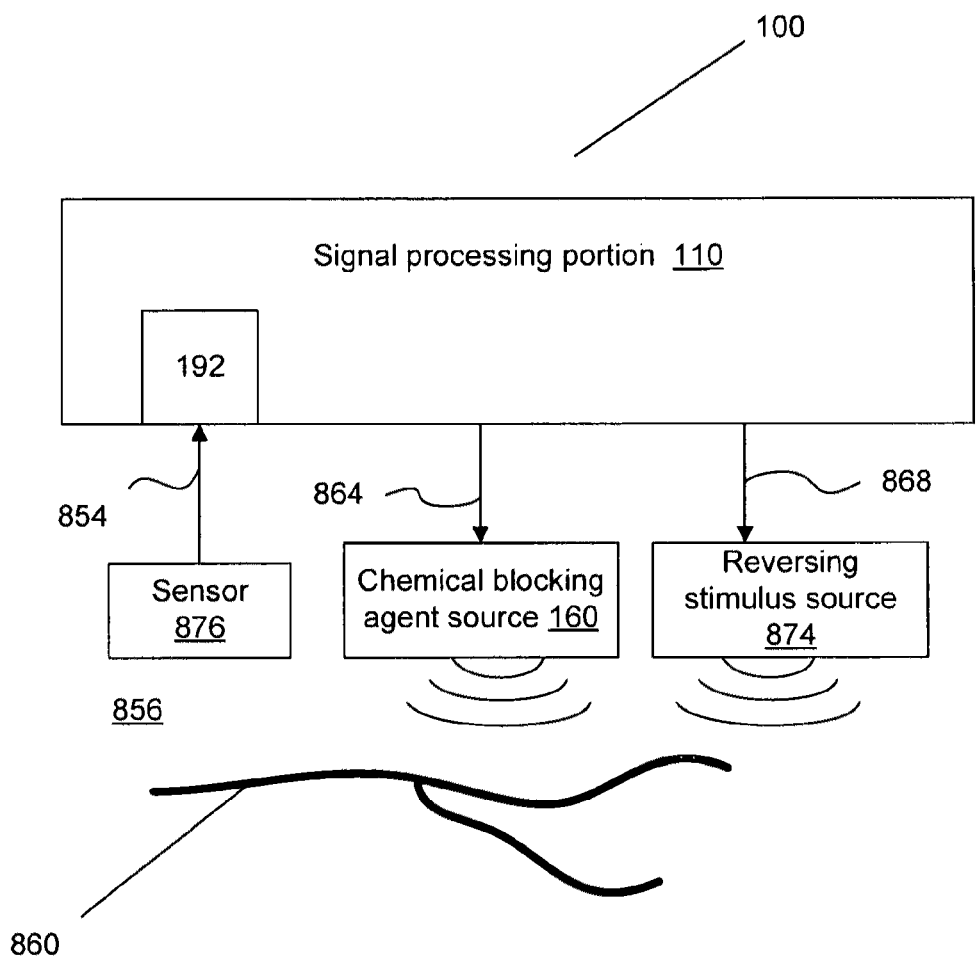
FIG. 17 is an illustration of an embodiment of a neural modulation system with a reversing stimulus source.

FIG. 17 illustrates an embodiment of a neural modulation system 100 that includes separate chemical blocking agent source 160 and reversing stimulus source 874. Neural modulation system 100 includes a signal input structure 192 configured to receive a signal 854 indicative of an activity state of at least a portion 856 of a body of a subject innervated by a peripheral neural structure 860, signal processing portion 110, chemical blocking agent source 160, and reversing stimulus source 874. Signal processing portion 110 may be configured to distinguish a first activity state of the at least a portion 856 of the body of the subject innervated by the peripheral neural structure 860 from a second activity state of the at least a portion 856 of the body of the subject innervated by the peripheral neural structure 860 from signal 854 received at signal input structure 192, generate chemical blocking agent control signal 864 for driving delivery of a chemical blocking agent 866 to reversibly block conduction in the peripheral neural structure 860 of the subject during at least a portion of the first activity state, and generate a reversing stimulus control signal 868 for driving production of a reversing stimulus 870 to counter chemical blocking agent 866 used to produce the reversible conduction block in the peripheral neural structure 860 of the subject. A chemical blocking agent source 160 may be configured to deliver a chemical blocking agent 866 responsive to the chemical blocking agent control signal 864, and a reversing stimulus source 874 may be configured to produce a reversing stimulus 870 responsive to the reversing stimulus control signal 868.

As noted previously, the action of a primary chemical blocking agent may be reversed by the addition of a chemical reversing agent. In some instances, the chemical reversing agent may be an antagonist that competes with the agonist chemical blocking agent at the active site on the neuromuscular target, resulting in a decrease in the response to the chemical blocking agent. For example, the nerve blocking activity of an opioid receptor agonist such as, for example, morphine may be reversed by an opioid antagonist such as, for example, nalmefene, naloxone, and naltrexone. Naloxone, for example, has been used to treat acute opioid overdose as well as the adverse effects associated with intravenous or epidural opioids during and post surgical intervention (Basic and Clinical Pharmacology, $10^{th}$ Edition. 2007; edited by Bertram Katzung, McGraw Hill Medical, New York, N.Y., which is incorporated herein by reference in its entirety). As another example, the benzodiazepine antagonist flumazenil may be used to reverse the effects of a benzodiazepine such as diazepam, lorazepam or midazolam. The prolonged action of a local anesthetic such as lidocaine in combination with an alpha adrenergic receptor agonist such as epinephrine or norepinephrine may be reversed by adding an alpha adrenergic receptor antagonist such as phentolamine, phentolamine hydrochloride, phentolamine mesylate, tolazoline, yohimbine, rauwolscine, doxazosin, labetolol, prazosin, tetrazosin and trimazosin as described in U.S. Pat. No. 6,764,678, which is incorporated herein by reference in its entirety. Alternatively, the chemical reversing agent may be an agonist that competes with the antagonist chemical blocking agent, resulting in a decrease in response to the chemical blocking agent. For example, a beta agonist such as isoproterenolol may be used to reverse the effects of a beta blocker. In some instances, the action of a chemical blocking agent such as a local anesthetic may be reversed using an inorganic or organic salt solution with a pH of 7 or higher as described in U.S. Pat. No. 5,192,527, which is incorporated herein by reference in its entirety.

The reversing stimulus may be any type of stimulus that serves to reverse the effect of the chemical blocking agent to bring the neural structure back to (or toward) its previous conductivity state. In some embodiments, the reversing stimulus source may be a chemical agent source generally of the same type as the chemical blocking agent source. In some embodiments, the reversing stimulus source may include at least a portion of the chemical blocking agent source, while in other embodiments, the reversing stimulus source may be a different or separate stimulus source of the same type as the chemical blocking agent source. In some embodiments, the reversing stimulus source may include a different type of stimulus source than the chemical blocking agent source. For example, the reversing stimulus source may include one or more of a magnetic field source, an electric field source, an electromagnetic transducer, an optical photon source, an acoustic energy source, a heat source or a cooling source.

Applying a reversing stimulus to counter the chemical blocking agent used to produce the reversible conduction block in the peripheral neural structure of the subject may include applying an electric or magnetic field to at least a portion of the peripheral neural structure. The electric or magnetic field used as a reversing stimulus may be a pulsed electric or magnetic field delivered to at least a portion of the peripheral neural structure, or it may be cyclical or time-varying electric or magnetic field.

In some embodiments, applying a reversing stimulus to counter the chemical blocking agent used to produce the reversible conduction block in the peripheral neural structure of the subject may include applying electromagnetic energy to at least a portion of the peripheral neural structure. Applying a reversing stimulus to counter the chemical blocking agent used to produce the reversible conduction blocking in the peripheral neural structure of the subject may include heating or cooling at least a portion of the peripheral neural structure.

Figure 18:
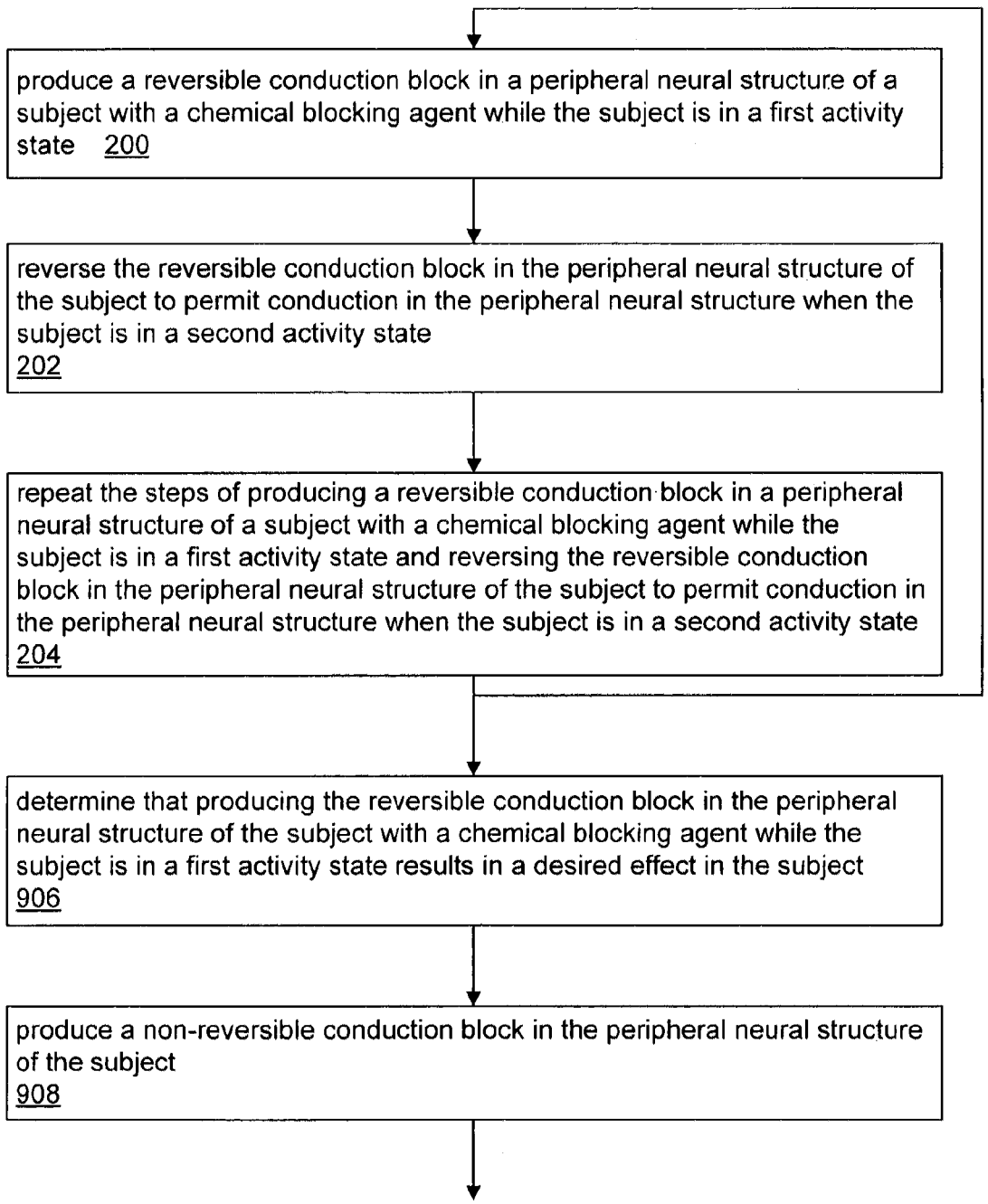
FIG. 18 is a flow diagram of a method of modulating neural activity.

FIG. 18 shows a further extension of the method of modulating neural activity outlined in FIG. 5. The method includes producing a reversible conduction block in a peripheral neural structure of a subject with a chemical blocking agent while the subject is in a first activity state (step 200), reversing the reversible conduction block in the peripheral neural structure of the subject to permit conduction in the peripheral neural structure when the subject is in a second activity state (step 202), repeating the steps of producing a reversible conduction block in a peripheral neural structure of a subject with a chemical blocking agent while the subject is in a first activity state and reversing the reversible conduction block in the peripheral neural structure of the subject to permit conduction in the peripheral neural structure when the subject is in a second activity state (step 204), determining that producing the reversible conduction block in the peripheral neural structure of the subject with a chemical blocking agent while the subject is in a first activity state results in a desired effect in the subject (step 906), and producing a non-reversible conduction block in the peripheral neural structure of the subject (step 908). A desired effect may be, for example, reduction or elimination of pain, undesired sensations, inflammation, immunological or physiological problems caused or contributed to by peripheral neural activity in the blocked peripheral neural structure. Determination that a desired effect has been produced may be made through sensing of various physiological or physical parameters, or by qualitative or subjective reporting obtained from the subject.

Figure 19:
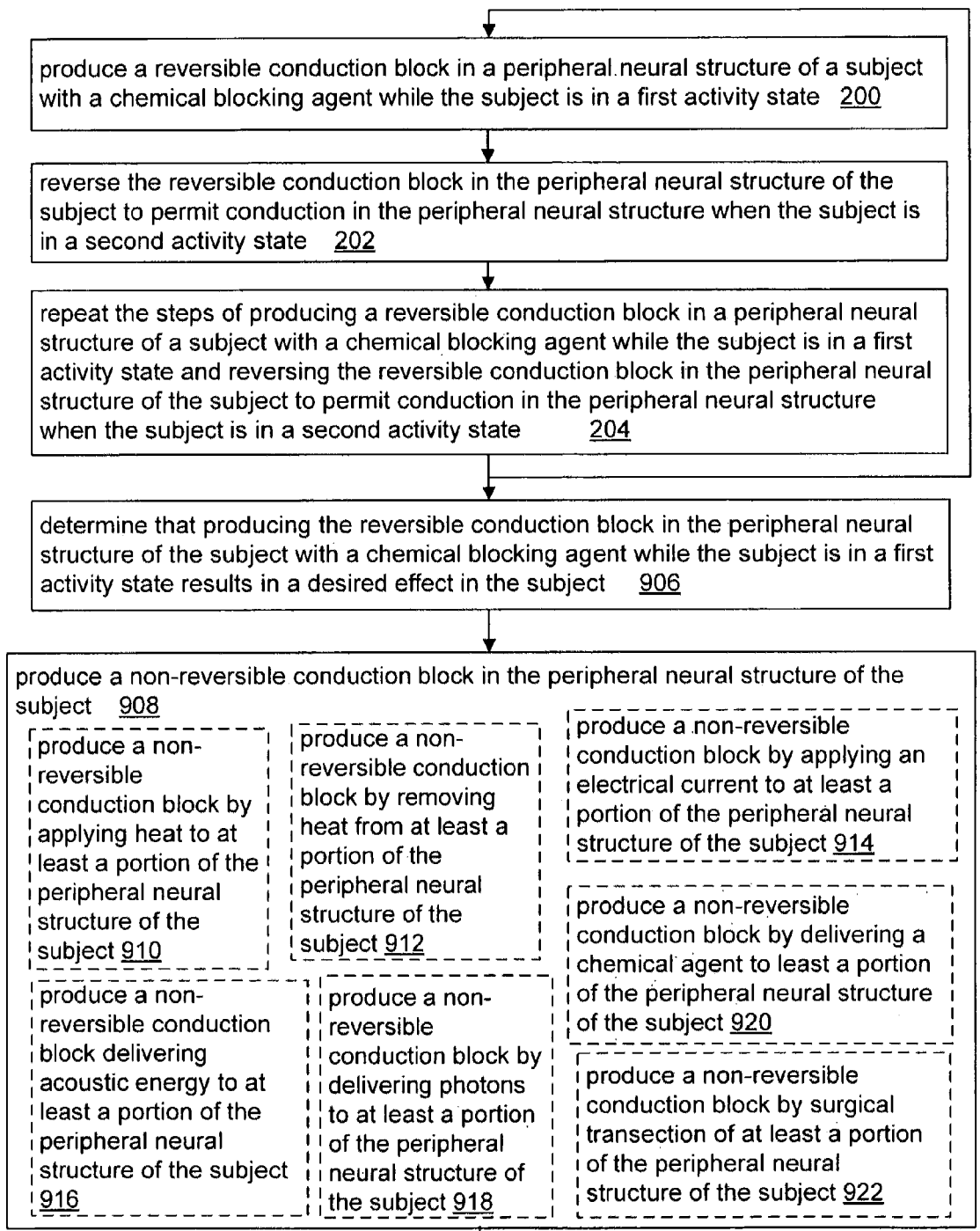
FIG. 19 is a flow diagram of a method of modulating neural activity.

A non-reversible conduction block may be produced in various ways. As shown in further detail in FIG. 19, a method including steps 200, 202, 204, 906 and 908 (as described in connection with in FIG. 18) may include producing a non-reversible conduction block by applying heat to at least a portion of the peripheral neural structure of the subject (as indicated at 910), for example with a Peltier device. Various other techniques can be used to apply heat, without limitation, as are known to those of skill in the art. Some examples include: electrical current, optical photons, ultrasound, the use of a resistive heater, an exothermic reaction device, etc. See, for example, U.S. Published Patent Application 2005/0288730, which is incorporated herein by reference. Heat may cause non-reversible conduction block by various mechanisms, e.g. chemical ablation of tissue or stimulation of apoptosis. See, for example, the method as disclosed in U.S. Pat. No. 6,405,732, which is incorporated herein by reference in its entirety. The present method is not limited to any particular mechanism of producing a non-reversible conduction block through application of heat. A non-reversible conduction block may be produced by cooling or removing heat from at least a portion of the peripheral neural structure of the subject (as indicated at 912), for example with a Peltier device, fluid heat transfer device, or endothermic reaction device; applying an electrical current to at least a portion of the peripheral neural structure of the subject (as indicated at 914); delivering acoustic energy to at least a portion of the peripheral neural structure of the subject (as indicated at 916); delivering photons to at least a portion of the peripheral neural structure of the subject (as indicated at 918); delivering a chemical agent (e.g. capsaicin) to at least a portion of the peripheral neural structure of the subject (as indicated at 920); or by surgical transection of at least a portion of the peripheral neural structure of the subject (as indicated at 922).

Producing a reversible conduction block may include producing substantially complete blockage of conduction in the peripheral neural structure of the subject. Alternatively, in some cases only partial blockage of conduction may be obtained, e.g. as depicted in FIGS. 2E and 2F. Completeness of blockage may be assessed by measuring neural activity by known methods, e.g., by delivering a well-defined stimulus on one side of the blocked region and measuring the evoked neural activity on the other side of the blocked region and, optionally, comparing the evoked activity to activity measured at the same site prior to blocking of conduction or at an location upstream of the block, either before or after blocking.

Figure 20:
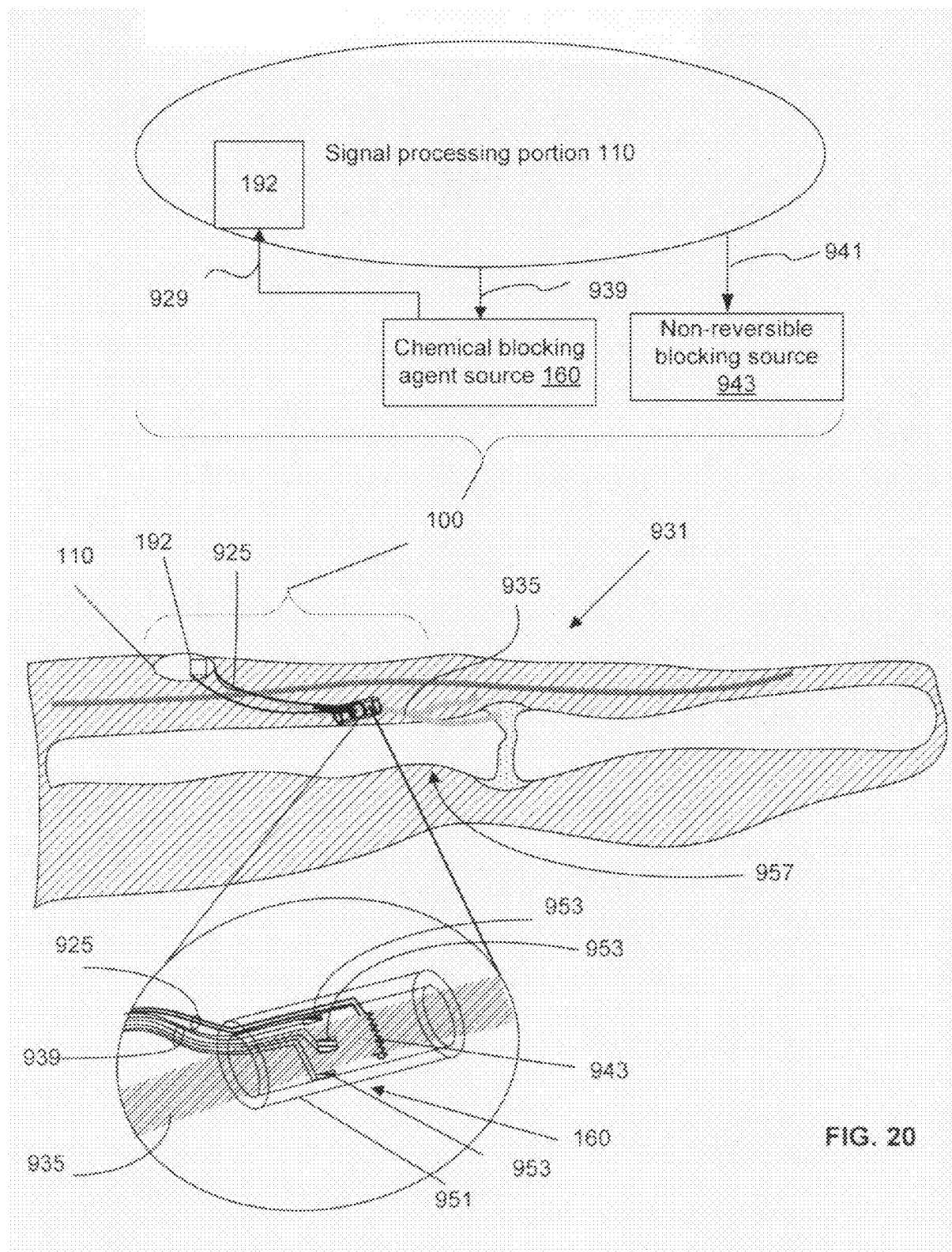
FIG. 20 is an illustration of an embodiment of a neural modulation system with a non-reversible blocking source.

FIG. 20 depicts a further embodiment of a neural modulation system that is similar to previously described systems, but in addition includes a non-reversible blocking source. The upper portion of FIG. 20 includes a block diagram of system 100, while the lower portion illustrates system 100 in situ in an appendage of a subject. Neural modulation system 100 may include signal input structure 192 configured to receive signal 929 indicative of an activity state of at least a portion 931 of a body of a subject innervated by a peripheral neural structure 935, and a signal processing portion 110 configured to distinguish a first activity state of the at least a portion 931 of the body of the subject innervated by the peripheral neural structure 935 from a second activity state of the at least a portion 931 of the body of the subject innervated by the peripheral neural structure 935 from signal 929 received at signal input structure 192. Signal 929 may be carried on line 925, as shown in the expanded view at the bottom of FIG. 20.

Signal processing portion is further configured to generate a chemical blocking agent control signal 939 for driving delivery of a chemical blocking agent adapted to reversibly block conduction in the peripheral neural structure 935 of the subject during at least a portion of the first activity state, determine that producing the reversible conduction block in peripheral neural structure 935 of the subject while the subject is in a first activity state results in a desired effect in the subject, and generate a non-reversible blocking source control signal 941. Neural modulation system 225 also includes chemical blocking agent source 160 configured to deliver a chemical blocking agent responsive to the chemical blocking agent control signal 939, and a non-reversible blocking source 943. Chemical blocking agent source 160 includes a plurality of chemical blocking agent reservoirs 953 distributed circumferentially around peripheral neural structure 935. Non-reversible blocking source control signal 941 drives non-reversible blocking source 943 to perform an action adapted for producing a non-reversible conduction block in peripheral neural structure 935 of the subject. Non-reversible blocking source control signal 941 is also carried on line 925, shown in the expanded view in the lower portion of FIG. 20. Non-reversible blocking source 943 may be configured to perform an action adapted for producing a non-reversible conduction block in the peripheral neural structure of the subject responsive to the non-reversible blocking source control signal 941. In the example shown in FIG. 20, non-reversible blocking source 943 is an electrode which can function as a heating element and which may also be used for sensing neural activity from peripheral neural structure 935. The sensed neural activity may be provided as signal 929 to signal input structure 192 on line 925, to serve as a source of information regarding activity of the portion 931 of the body of the subject innervated by peripheral neural structure 935, which in the present example is the region of joint 957 in body portion 931. Non-reversible blocking source 943 may be configured to produce thermal ablation of at least a portion of the peripheral neural structure of the subject, or to stimulate apoptosis in the peripheral neural structure, for example. The practice of the invention is not limited to any particular mechanism for producing non-reversible blocking. Alternatively, a heat source may include, but is not limited to, an appropriately configured Peltier device, a light source, a fluid heat-transfer device, an exothermic reaction device, or an acoustic element.

In other embodiments, the non-reversible blocking source may include a cooling source, such as an appropriately configured Peltier device or a reservoir containing a chemical composition or mixture capable of undergoing a controllable endothermic reaction. In other embodiments, the non-reversible blocking source may include an electrical current source, and acoustic energy source, a photon source, or a chemical blocking agent source. In general, a non-reversible blocking source may be any source of any type of energy, material, or action sufficient to damage or destroy the peripheral neural structure to produce permanent (or substantially permanent) blockage of nerve conduction. As a further example, in some embodiments, the non-reversible blocking source may include a surgical transection mechanism.

In some embodiments, a chemical blocking agent source may be configured to produce a spatially varying chemical blocking stimulus. A spatially varying chemical blocking stimulus may be produced, for example, by a chemical blocking agent source that includes a plurality of spatially distributed chemical agent sources, which may be distributed circumferentially around the nerve, as depicted in FIG. 20, or in other distributions, including but not limited to, a longitudinal distribution along the nerve or an array disposed over or around the nerve. A plurality of spatially distributed chemical agent sources may include a plurality of stimulus sources all of the same type, or may include different types of chemical agent sources. In some cases, a plurality of spatially distributed chemical agent sources may deliver different types of chemical agents.

Figure 21:
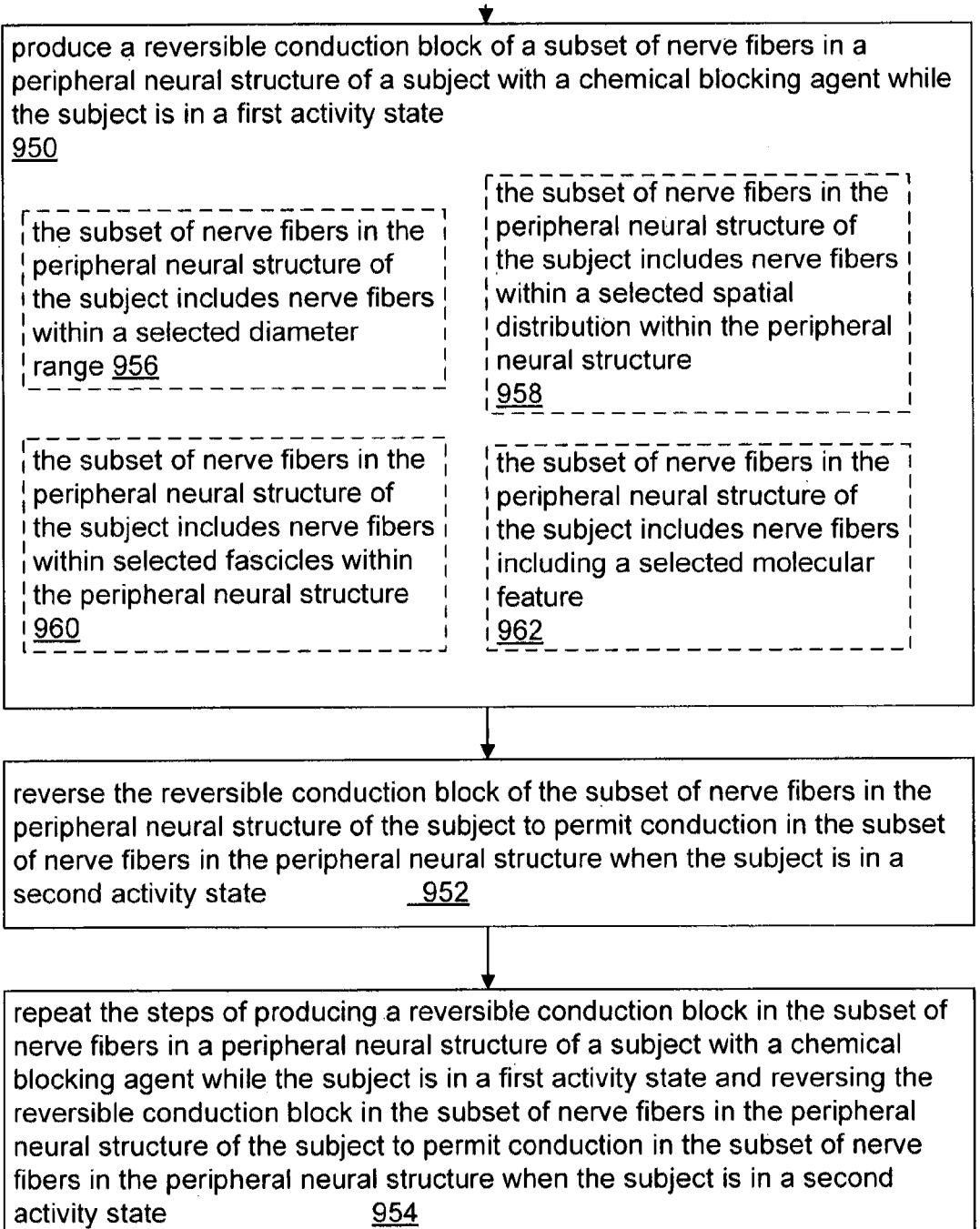
FIG. 21 is a flow diagram of a method of modulating neural activity.

FIG. 21 illustrates a further variant of a method of modulating neural activity, which may include producing a reversible conduction block of a subset of nerve fibers in a peripheral neural structure of a subject with a chemical blocking agent while the subject is in a first activity state (step 950), reversing the reversible conduction block of the subset of nerve fibers in the peripheral neural structure of the subject to permit conduction in the subset of nerve fibers in the peripheral neural structure when the subject is in a second activity state (step 952), and repeating the steps of producing a reversible conduction block in the subset of nerve fibers in a peripheral neural structure of a subject with a chemical blocking agent while the subject is in a first activity state and reversing the reversible conduction block in the subset of nerve fibers in the peripheral neural structure of the subject to permit conduction in the subset of nerve fibers in the peripheral neural structure when the subject is in a second activity state (step 954). In different variations of the method (indicated with dashed boxes in FIG. 21) the subset of nerve fibers in the peripheral neural structure of the subject may include nerve fibers within a selected diameter range, as indicated at 956, within a selected spatial distribution within the peripheral neural structure, as indicated at 958, within selected fascicles and/or within the peripheral neural structure, as indicated at 960, based upon location of delivery of chemical agent or differential sensitivity of different diameter fibers to chemical blocking agents.

Alternatively, or in addition, the subset of nerve fibers in the peripheral neural structure of the subject may include nerve fibers including a selected molecular feature (as indicated at 962). Selective blocking of nerve fibers having particular molecular features has been described in Binshtok, A. M.; Bean, B. P. and Woolf, C. J.; "Inhibition of nociceptors by TRPV1-mediated entry of impermeant sodium channel blockers"; Nature, Vol. 449, 2007; pp. 607-611; doi:10.1038/nature06191 and McCleskey, E. M. "A local route to pain relief"; Nature; Vol. 449; 2007; pp. 545-546, which are incorporated herein by reference. Responsiveness of nerve fibers having selected molecular features to chemical blocking agents may be modulated, for example, by materials targeted to nerve fibers having the molecular feature. A variety of molecular markers for specific types of nerve fibers are known. For example, neurofilament (NF) is a highly specific marker for myelinated nerve fibers; substance P and calcitonin gene-related protein (CGRP) are markers for sensory nerve fibers (both A and c-type); Acetylcholine (Ach) is a marker for cholinergic nerve fibers, which may be sympathetic pre-ganglionic fibers or parasympathetic pre-ganglionic or post-ganglionic fibers; tyrosine hydroxylase (TH) is specific for adrenergic nerve fibers (sympathetic postganglionic neurons). For example, see Tokushige, N.; Markham, R.; Russell, P. and Fraser, I. S.; "Nerve fibres in peritoneal endometriosis"; Human Reproduction; 2006; Vol. 21; No. 11; pp. 3001-3007, which is incorporated herein by reference in its entirety. Cyclin dependent kinase 5 (Cdk5) is expressed in nociceptive fibers (Pareek, T. K.; Keller, J.; Kesavapany, S.; Pant, H. C.; Iadarola, M. J.; Brady, R. O.; and Kulkarni, A. B.; "Cyclin-dependent kinase 5 activity regulates pain signaling"; PNAS; Jan. 17, 2006; Vol. 103, No. 3; pp. 791-796), incorporated herein by reference in its entirety. Similarly, capsaicin receptor (vanilloid receptor type 1 (VR1) and variants thereof, e.g. vanilloid receptor homologue (VRL1) are expressed in A and C fiber sensory neurons, as described in Ma, Q.-P.; "Vanilloid receptor homologue, VRLl, is expressed by both A- and C-fiber sensory neurons"; Neuro Report; Vol. 12, No. 17; 4 Dec. 2001; pp. 3693, which is incorporated herein by reference in its entirety.

In some embodiments of a neural modulation system, a chemical blocking agent source may be configured to produce substantially complete blockage of conduction in the peripheral neural structure of the subject responsive to the chemical blocking agent control signal. In other embodiments, a chemical blocking agent source may be configured to produce blockage of a subset of nerve fibers in the peripheral neural structure of the subject responsive to the chemical blocking agent control signal, based, for example, upon approaches as described above. The subset of nerve fibers in the peripheral neural structure of the subject may include nerve fibers within a selected diameter range, nerve fibers within a selected spatial distribution within the peripheral neural structure, or nerve fibers including a selected molecular feature.

Figure 22A:
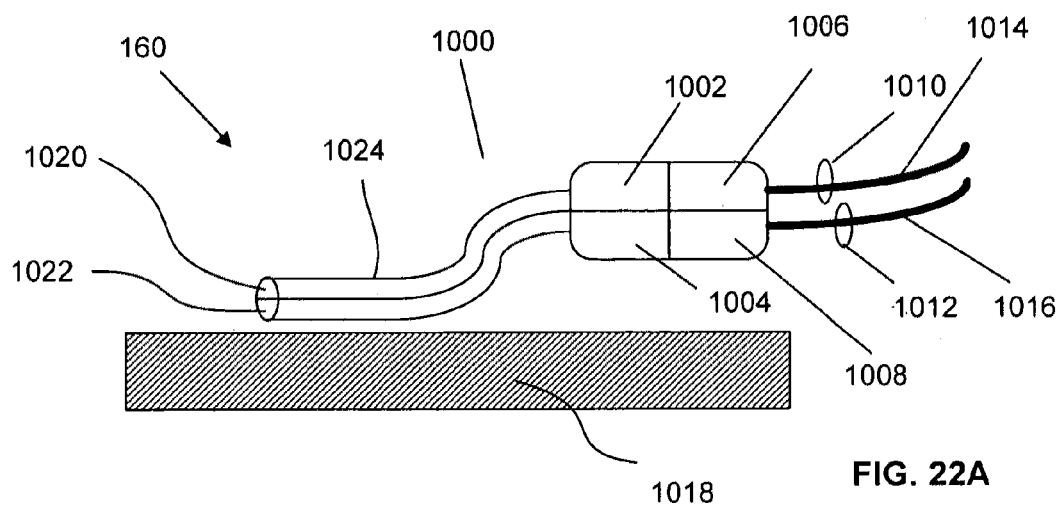
FIGS. 22A-22C depict examples of chemical blocking agent sources.
Figure 22B:
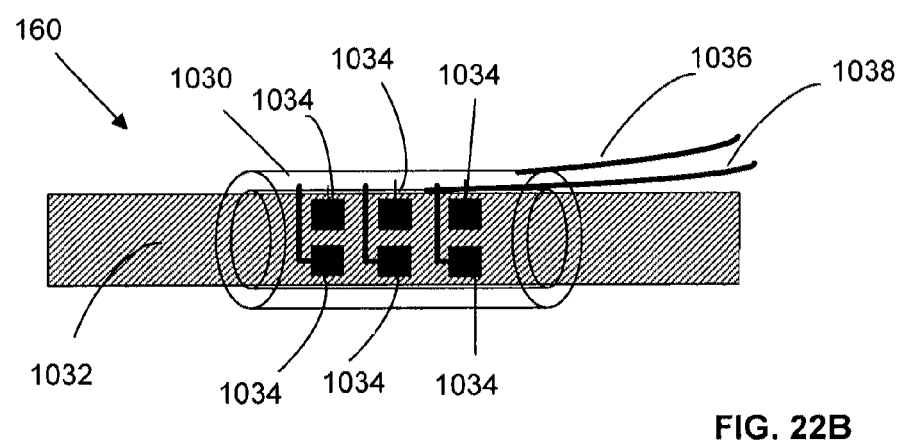
Figure 22C:
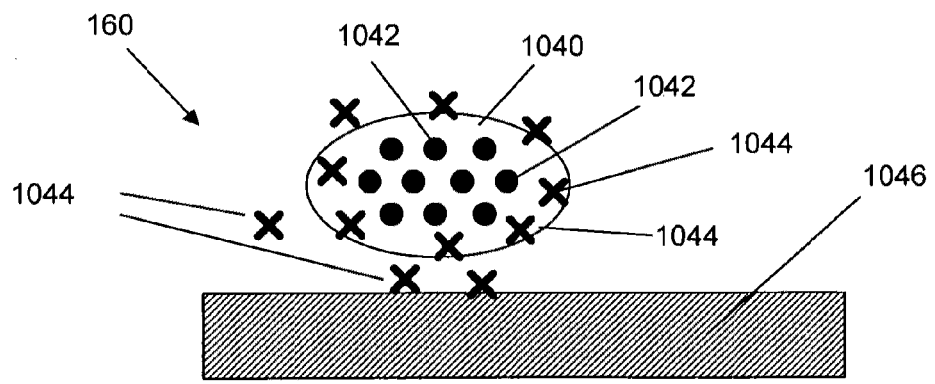

FIGS. 22A-22C depict examples of chemical blocking agent sources 160 that may be used in neural modulation systems as described and depicted generally herein.

In FIG. 22A, chemical blocking agent source 160 is an infusion pump 1000, similar to that depicted in FIG. 13, but configured to deliver two chemical agents. Infusion pump 1000 includes reservoir 1002 containing a first chemical agent and reservoir 1004 containing a second chemical agent. Chemical agents are driven from reservoirs 1002 and 1004 by pumps 1006 and 1008, respectively, under the control of one or more control signals 1010 and 1012, which may be provided to pumps 1006 and 1008 from a controller (not shown) via either leads 1014 and 1016 as depicted in FIG. 22A, or, alternatively, via a wireless connection. First and second chemical agents are delivered in the vicinity of peripheral neural structure 1018 through first lumen 1020 and second lumen 1022, respectively of dual lumen catheter 1024.

In some embodiments, a neural modulation system may deliver a combination of chemical blocking agent components. The components may be delivered from a single chemical blocking agent source, or, alternatively, from multiple sources. For example, the infusion pump 1000 depicted in FIG. 22A may be used in such a system. Such a system may include a primary chemical blocking agent source configured to deliver a primary chemical blocking agent component and a secondary chemical blocking agent source configured to deliver a secondary chemical blocking agent component. The primary chemical blocking agent component and the secondary chemical blocking agent component act together to reversibly block conduction in the peripheral neural structure. For example, referring to FIG. 22A, the signal processing portion (not shown) may be configured to generate a chemical blocking agent control signal including a primary chemical blocking agent control signal 1010 for driving delivery of the primary chemical blocking agent component (from reservoir 1002) and a secondary chemical blocking agent control signal 1012 for driving delivery of the secondary chemical blocking agent component (from reservoir 1004).

Producing a reversible conduction block in a peripheral neural structure of a subject with a chemical blocking agent may include delivering a primary chemical blocking agent component and delivering a secondary chemical blocking agent component, wherein the primary chemical blocking agent component and the secondary chemical blocking agent component act together to reversibly block conduction in the peripheral neural structure.

A primary chemical blocking agent may be used in combination with one or more secondary chemical blocking agents. Primary and secondary chemical blocking agents may have the same method of action such as, for example, two or more opiates. Alternatively, the primary and secondary chemical blocking agents may have different methods of action such as one or more opioid agonist in combination, for example, with a local anesthetic, an NSAID, and/or a benzodiazepine. For example, a primary chemical blocking agent such as the opiate hydrocodone might be used in combination with a secondary chemical blocking agent such as the NSAID ibuprofen as exemplified by the therapeutic combination drug Vicoprofen. Similarly, a sodium channel blocker such as tetrodotoxin or saxitoxin may be used in combination with a local anesthetic, vasoconstrictor, glucocorticoid, alpha agonist (e.g., epinephrine, phenylephrine), beta-blockers (e.g., propranalol), and mixed central-peripheral alpha-2 agonists (e.g., clonidine) to enhance the neural blockade as described in U.S. Pat. No. 6,326,020, which is incorporated herein by reference in its entirety.

A chemical blocking agent may be delivered using an implantable delivery device or system that incorporates a MEMS (Micro Electro Mechanical Systems) fabricated microchip. Examples of MEMS and/or microfabricated devices for potential delivery of a therapeutic agent are described in U.S. Pat. Nos. 5,993,414; 6,454,759; and 6,808,522, which are incorporated herein by reference in their entirety. The MEMS implantable delivery method may have one or more microfabricated drug reservoirs such as, for example, microparticle reservoirs, silicon microarray reservoirs, and/or polymer microreservoirs as described by Grayson, A. C. R, Shawgo, R. S., Johnson, A. M., Flynn, N. T., Yawen, L., Cima, M. J., and Langer, R. "A bioMEMS review: MEMS technology for physiologically integrated devices." Proceedings of the IEEE, 2004, Vol. 92, No. 1, pp. 6-21, which is incorporated herein by reference in its entirety. Microparticles fabricated from silicon may be used that contain an internal space which is loaded with drug using a microinjector and capped, for example, with a slow dissolving gelatin or starch. Polymer microreservoirs may be fabricated by micromolding poly(dimethylsiloxane) or by patterning in multilayer poly(D-lactic acid) and (vinyl alcohol), for example. In some instances, the polymer microreservoirs may be capped with polymers that degrade at various rates in vivo depending upon the length of the polymer, allowing for controlled release of multiple doses. Alternatively, an array of microreservoirs on a microchip may be used in which each dose of chemical blocking agent is contained in its own reservoir and capped by an environmentally sensitive material. For example, the microreservoirs may be capped with a gold membrane which is weakened and ruptured by electrochemical dissolution in response to application of an anode voltage to the membrane in the presence of chloride ions, resulting in release of drug as described in U.S. Pat. No. 5,797,898 and in Prescott, J. H., Lipka, S., Baldwin, S., Sheppard, N. F., Maloney, J. M., Coppeta, J., Yomtov, B., Staples, M. A., and Santini, J. T., "Chronic, programmed polypeptide delivery from an implanted, multireservoir microchip device." Nat. Biotech. 2006, Vol. 24, No. 4, pp. 437-438, which are incorporated herein by reference in their entirety. Alternatively, the microreservoirs may be capped by a temperature sensitive material that may be ruptured in response to selective application of heat to one or more of the reservoirs as described in U.S. Pat. No. 6,669,683, which is incorporated herein by reference in its entirety. Wireless induction of a voltage or thermal trigger, for example, to a given reservoir of the microarray by a subject would enable on-demand release of a chemical blocking agent. Alternatively, the microchip array may incorporate a sensor component that signals release of a chemical blocking agent by a closed-loop mechanism in response to a chemical or physiological state as described in U.S. Pat. No. 6,976,982, which is incorporated herein by reference in its entirety. FIG. 22B depicts a chemical blocking agent source 160 that includes a cuff 1030 positioned around peripheral neural structure 1032 and includes a plurality of reservoirs 1034, each containing a chemical blocking agent. Each reservoir may be separately addressable by control lines 1036 and 1038, though in some cases it may be desirable to control more than one reservoir with a single control line.

In further embodiments, an implantable delivery device may incorporate a polymer or other matrix that releases a chemical blocking agent. For example, FIG. 22C illustrates a chemical blocking agent source 160 of this type. In FIG. 22C, polymeric matrix 1040 contains embedded ferromagnetic particles 1042 and chemical blocking agent 1044. Chemical blocking agent 1044 may be released from polymeric matrix 1040 applying a magnetic field to produce heating of ferromagnetic particles 1042, to cause polymeric matrix 1040 to release chemical blocking agent 1044 in the vicinity of peripheral neural structure 1046. See for example, Hsieh, D. S. T., Langer, R., Folkman, J. "Magnetic modulation of release of macromolecules from polymers," Proc. Natl. Acad. Sci. U.S.A., 1981, Vol. 78., No. 3., pp. 1863-1867, which is incorporated herein by reference in its entirety. Alternatively, in related embodiments, a biologically active compound may be formulated with a solid hydrophilic polymer that swells by osmotic pressure after implantation, allowing interaction with a solubilizing agent and release of the biologically active compound through a non-porous rate-controlling membrane as described in U.S. Pat. No. 5,035,891, which is incorporated herein by reference in its entirety.

In some instances, an implantable delivery system may incorporate a natural and/or synthetic stimulus-responsive hydrogel or polymer which changes confirmation rapidly and reversibly in response to environmental stimuli such as, for example, temperature, pH, ionic strength, electrical potential, light, magnetic field or ultrasound (see, e.g., Stubbe, B. G., De Smedt, S. C., and Demeester, J. "'Programmed polymeric devices' for pulsed drug delivery," Pharmaceutical Res. 2004, Vol. 21, No. 10, pp. 1732-1740, which is incorporated herein by reference in its entirety). Examples of polymers are described in U.S. Pat. Nos. 5,830,207; 6,720,402; and 7,033,571, which are incorporated herein by reference in their entirety. In some instances, the chemical blocking agent to be delivered by the implantable delivery method may be dissolved or dispersed in the hydrogel or polymer. Alternatively, a hydrogel and/or other stimulus-responsive polymer may be incorporated into an implantable delivery device. For example, a hydrogel or other polymer or other smart material may be used as an environmentally sensitive actuator to control flow of a therapeutic agent out of an implantable device as described in U.S. Pat. Nos. 6,416,495; 6,571,125; and 6,755,621, which are incorporated herein by reference in their entirety. As such, an implantable delivery device may incorporate a hydrogel or other polymer that modulates delivery of one or more chemical blocking agents in response to environmental conditions.

An implantable chemical blocking agent source as illustrated in FIGS. 22A-22C, or alternatively, as described and depicted elsewhere herein, may be powered by a current source, which may be fully implantable. Alternatively, current may be supplied by via a wireless transcutaneous link (e.g., as described in U.S. Pat. No. 7,236,822, which is incorporated herein by reference in its entirety). An implantable device for delivery of a chemical blocking agent may be powered by a standard lithium battery. In some instances, the battery may be rechargeable. For example, a battery associated with an implantable device may be recharged transcutaneously via inductive coupling from an external power source temporarily positioned on or near the surface of the skin as described in U.S. Pat. No. 7,286,880, which is incorporated herein by reference in its entirety. Alternatively, the energy source for an implantable device may come from within the subject. For example, an implantable device may be powered by conversion of thermal energy from the subject into an electrical current as described in U.S. Pat. No. 7,340,304, which is incorporated herein by reference in its entirety.

The pattern of delivery of the chemical blocking agent may vary spatially as well as temporally, and in some embodiments it may vary both spatially and temporally. A single neural modulation system as depicted, for example, in FIGS. 22A and 22B may deliver chemical blocking agents at multiple locations, and by varying the rate of delivery of chemical blocking agents from each chemical blocking agent source, a spatially and/or time varying pattern of delivery may be produced. Alternatively, multiple neural modulation systems, distributed spatially with regard to one or more peripheral neural structures may be used to produce a spatially varying delivery pattern in other embodiments.

Various configurations and combinations of devices/structures for delivering chemical agents may be used to produce conduction block by the approaches described herein, and the invention is not limited to any particular type/configuration of chemical agent sources. In order to control delivery of a chemical agent to produce either blocking or excitation, a chemical agent source may be connected (via a wired or wireless connection) to an energy source such as an electrical current or voltage source. Accordingly, the term "chemical agent source", as used herein, is considered to include at least one supply of a chemical agent and a mechanism for affecting delivery of the chemical agent, and may also include one or more source of energy for enabling delivery of the chemical agent(s).

Figure 23:
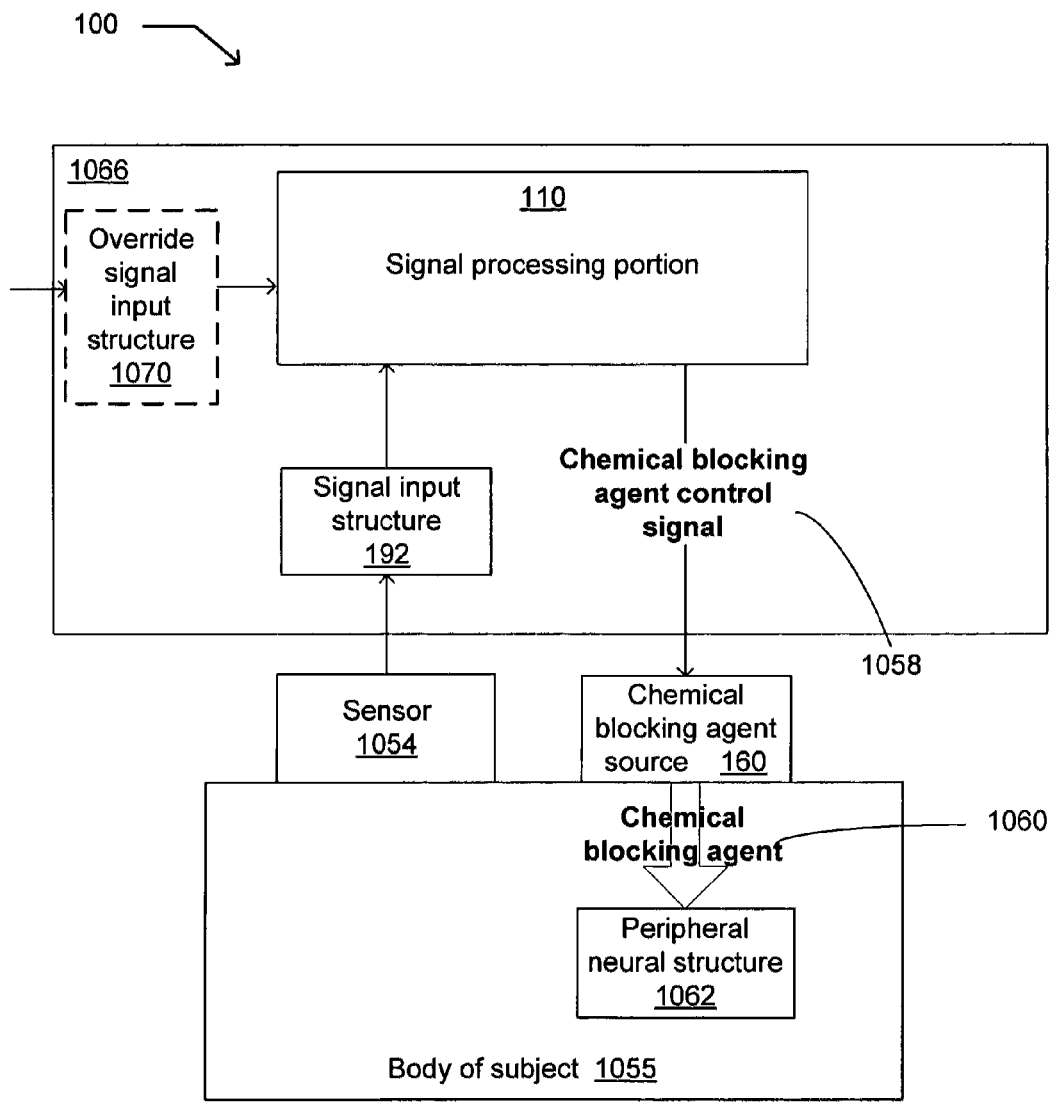
FIG. 23 is a block diagram of an example of a neural modulation system.

Methods of neural modulation as described herein may be implemented with a neural modulation system 100 as illustrated generally in FIG. 23, which depicts a variation of the system shown in FIG. 3. Basic components of neural modulation system 100 include a signal input structure 192, sensor 1054, and signal processing portion 110. Signal input structure 192 may be operatively connected to sensor 1054 and configured to receive a signal indicative of an activity state of at least a portion of a body of a subject 1055 innervated by a peripheral neural structure. Signal input structure 192, and other signal input structures described elsewhere herein, may be of various types configured to accept or receive signals of various types. Such signal input structures are known to those of skill in the art, and may include, but are not limited to, analog or digital inputs capable of accepting or receiving electrical, optical, acoustic, electromagnetic, or other types of signals. Signals may be accepted or received at a signal input structure through direct physical contact (e.g., an electrical contact), or by reception of a signal transmitted through or across a medium (e.g., via an inductive, optical, or electromagnetic link). Sensor 1054 may be operatively connected to the signal input structure 192 and configured to generate a signal indicative of an activity state of a portion of the body of the subject 1055 innervated by the peripheral neural structure responsive to an activity of the portion of the body. Signal processing portion 110 may be configured to distinguish a first activity state at least partially based on the signal received by the signal input structure 192, and to generate a chemical blocking agent control signal 1058 for driving delivery of a chemical blocking agent 1060 by chemical blocking agent source 160.

FIG. 23 depicts in schematic form an embodiment of a neural modulation system 100, in which signal processing portion 110 and signal input structure 192 are packaged together in package 1066 and sensor 1054, and chemical blocking agent source 160 is packaged separately. In some embodiments, chemical blocking agent source 160 or portion thereof may be located outside the body of the subject, and the chemical blocking agent may pass through the skin and underlying tissue to reach the neural structure that is to be blocked. In other embodiments, a chemical blocking agent source may be positioned within the body of the subject, either permanently or temporarily. Suitable positioning of the chemical blocking agent source will depend upon the type of chemical blocking agent source being used and the type and location of the neural structure to be blocked.

Neural modulation system 100 may optionally include override signal input structure 1070, as indicated by the dashed box in FIG. 23. Override signal input structure 1070 may be configured to receive a signal indicative of a condition of the body of the subject, and signal processing portion 110 may be configured to override generation of the chemical blocking agent control signal 1058 responsive to a signal indicative of an override condition of the body of the subject on override signal input structure 1070. Alternatively, override signal input structure 1070 may be configured to receive a signal indicative of a condition external to the body of the subject, and signal processing portion 110 may be configured to override generation of the chemical blocking agent control signal responsive to a signal indicative of an override condition external to the body of the subject on the override signal input. As a further alternative, or in addition, override signal input structure 1070 may be configured to receive a signal from a user input device, and the signal processing portion may be configured to override generation of the chemical blocking agent control signal responsive to a signal indicative of a user override request on the override signal input. The override signal may indicate that it is no longer desirable to apply the chemical blocking agent, for reasons of safety, comfort, or convenience, for example, and may be indicative of a condition of the body of the subject, or of a condition external to the body of the subject (e.g., in the environment of the subject). If the override signal is detected from a user input device, it may be the same user input device used in normal operation of the system, and the override signal input structure may be the same as the signal input structure that normally receives input from a user input device.

Sensor 1054 as depicted generally in FIG. 23 (as well as sensors used in other embodiments depicted and/or described herein) may be any of a variety of different types of sensors, including, but not limited to, pressure sensors, force sensors, chemical sensors (including but not limited to sensors capable of sensing pH, gas, ions, proteins, or biomolecules), temperature sensors, electrical sensors (for sensing current, potential, charge, resistance, resistivity, capacitance, or other electrical parameters), magnetic sensors, optical sensors, motion sensors, etc. A single sensor or multiple sensors, of the same or multiple different types, may be used.

The signal processing portion 110, as depicted in FIG. 23, may be configured to determine the onset of the first activity state and generate the chemical blocking agent control signal for driving delivery of a chemical blocking agent adapted to reversibly block conduction in the peripheral neural structure of the subject at least intermittently responsive to detecting the onset of a first activity state in the subject. In some cases, the signal processing portion may be configured to generate the chemical blocking agent control signal for driving delivery of a chemical blocking agent adapted to reversibly block conduction in the peripheral neural structure of the subject substantially immediately upon detecting the onset of the first activity state in the subject. In other cases, the signal processing portion may be configured to generate the chemical blocking agent control signal for driving delivery of a chemical blocking agent adapted to reversibly block conduction in the peripheral neural structure of the subject at a delay interval after detecting the onset of the first activity state in the subject. The signal processing portion may be configured to initiate a release period during which no chemical blocking agent control signal is generated after an interval determined relative to the onset of generation of the chemical blocking agent control signal.

In some cases, the signal processing portion may be configured to determine the onset of the second activity state in the subject and initiate a release period during which no chemical blocking agent control signal is generated responsive to detecting the second activity state in the subject. The signal processing portion may be configured to initiate the release period substantially immediately upon detection of the onset of the second activity state in the subject, or to initiate the release period at a delay interval after detection of the onset of the second activity state in the subject.

Components of neural modulation systems of the type described herein may be packaged in various manners. In some cases, all components of a system may be packaged together. Such a package may be designed for use outside the body, or designed for use inside the body in an implantable system. However, in many cases it may be desirable to package certain components of the system separately. Communication between system components may be wireless, e.g. as described in US. Pat. No. 6,208,894, which is incorporated herein by reference in its entirety. The system may include the capability for remote programming, interrogation, or telemetry, for example as described in U.S. Pat. No. 7,263,405, which is incorporated herein by reference in its entirety.

Figure 24:
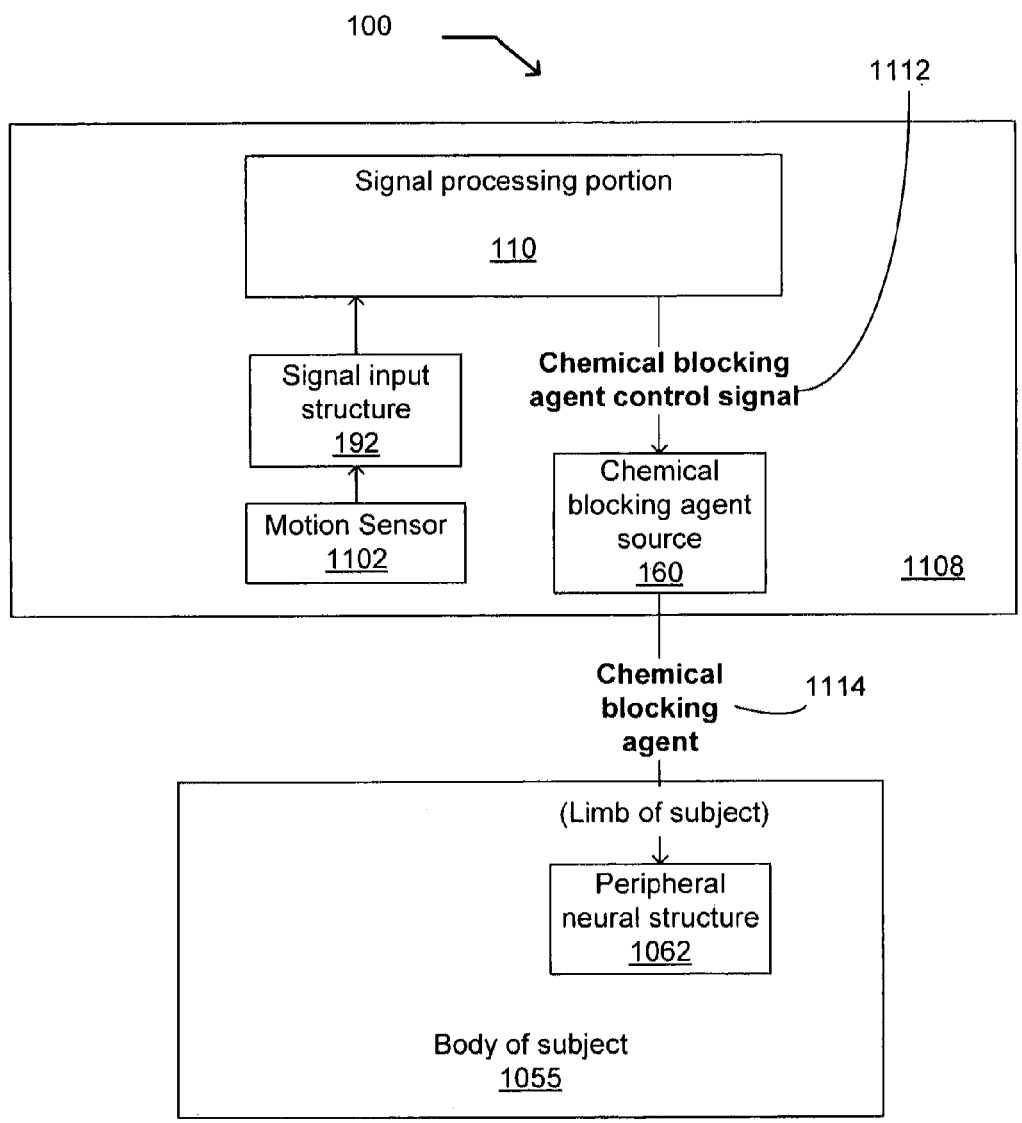
FIG. 24 is a block diagram of an example of a neural modulation system.

FIG. 24 depicts an example of a neural modulation system 100 in which a sensor (motion sensor 1102) and chemical blocking agent source are packaged with signal processing portion 110 in package 1108. Motion sensor 1102 provides an input to signal processing portion 110 via signal input structure 192. Signal processing portion 110 generates chemical blocking agent control signal 1112 which drives delivery of chemical blocking agent 1114 by chemical blocking agent source 160. Package 1108 may be adapted to be positioned external to the body of subject 1055, and chemical blocking agent 1114 may pass through body tissues to reach peripheral neural structure 1062. Chemical blocking agent source 160 may include, for example, components of an iontophoresis, electroporation, phonophoresis, sonophoresis, or other system configured to deliver a chemical blocking agent to the body of the subject sufficient to produce blocking of a nerve, as described elsewhere herein. Package 1108 may be configured to secured to a limb (e.g., with a strap or elastic band) over a peripheral neural structure 1062, so that the chemical blocking agent may be delivered to the peripheral neural structure. Generation of chemical blocking agent control signal 1112 by signal processing portion 110 may be responsive to a signal from motion sensor 1102, such that a chemical blocking agent may be delivered to the peripheral neural structure when the limb is not in motion, for example. The peripheral neural structure may be, for example, a sensory nerve, and blockage of neural activity therein may, for example, reduce or limit pain or inflammation, e.g. of arthritis, peripheral vascular disease, etc. In related embodiments, sensor 1102 may be any of various types of sensors, as described elsewhere herein.

Figure 25:
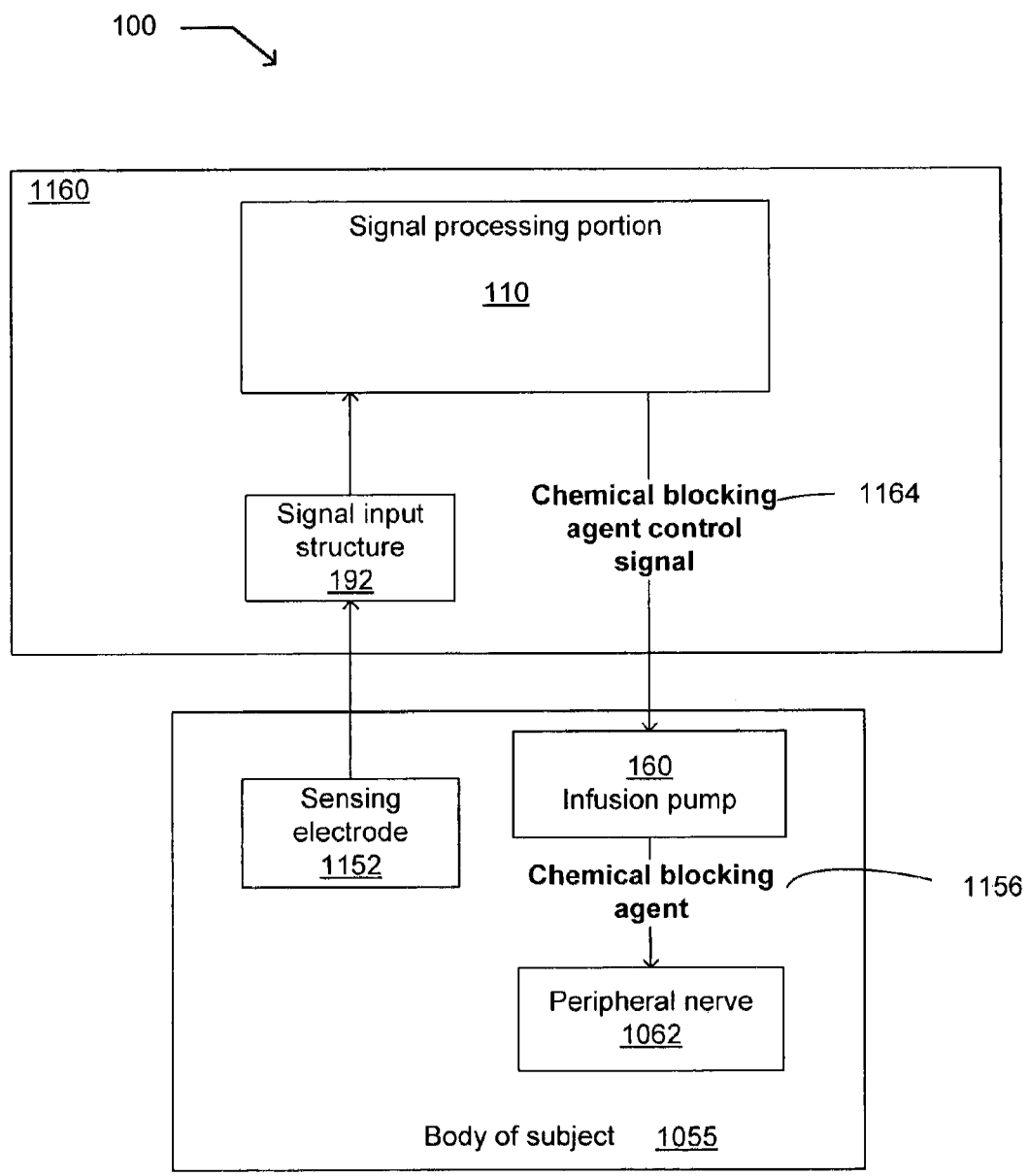
FIG. 25 is a block diagram of another example of a neural modulation system.

FIG. 25 depicts an example of a neural modulation system 100 in which an implanted sensor and implanted chemical blocking agent source are used. In this example, the implanted sensor may be sensing electrode 1152, and the chemical blocking agent source 160 may be an infusion pump. The infusion pump may, for example, be as described in U.S. Pat. Nos. 5,814,019 and 6,666,845, which are incorporated herein by reference in their entirety. In other implanted devices, other chemical agent delivery devices/mechanisms may be used, as described elsewhere herein. Sensing electrode 1152 and infusion pump (chemical blocking agent source 160) may be implanted within the body of subject 1055, such that sensing electrode 1152 may sense neural or muscular activity representative of activity of at least a portion of the body of the subject, and the infusion pump (160) may deliver chemical blocking agent 1156 to a peripheral neural structure, peripheral nerve 1062. As used herein, "implanted" means located or positioned, either temporarily or permanently, within the body of the subject. Signal processing portion 110 may be packaged separately, e.g. in package 1160. Sensing electrode 1152 may provide an input to signal processing portion 110 via signal input structure 192. Signal processing portion 110 may generate chemical blocking agent control signal 1164 for driving delivery of chemical blocking agent 1156 by infusion pump 1154. Package 1160 may be implanted within the body of subject 1055, or located external to body of subject 1055. In either case, signals may be transmitted between signal processing portion 110 and sensing electrode 1152 and chemical blocking agent source 160 (infusion pump) via a wire or cable, optical ink, acoustic link, radio frequency or other electromagnetic link, or other wireless communication link, as is known to those of skill in the art.

Blockage of neural activity may reduce or limit pain or inflammation. In an application, as depicted in FIG. 25, for example, sensing electrode 1152 and chemical blocking agent source 160 (the infusion pump) may be implanted adjacent a sensory nerve innervating a limb, appendage, or joint (for example, a knee) that has suffered injury and/or damage, with the goal of limiting the progression of arthritis that would otherwise be associated with the injury or damage.

Figure 26:
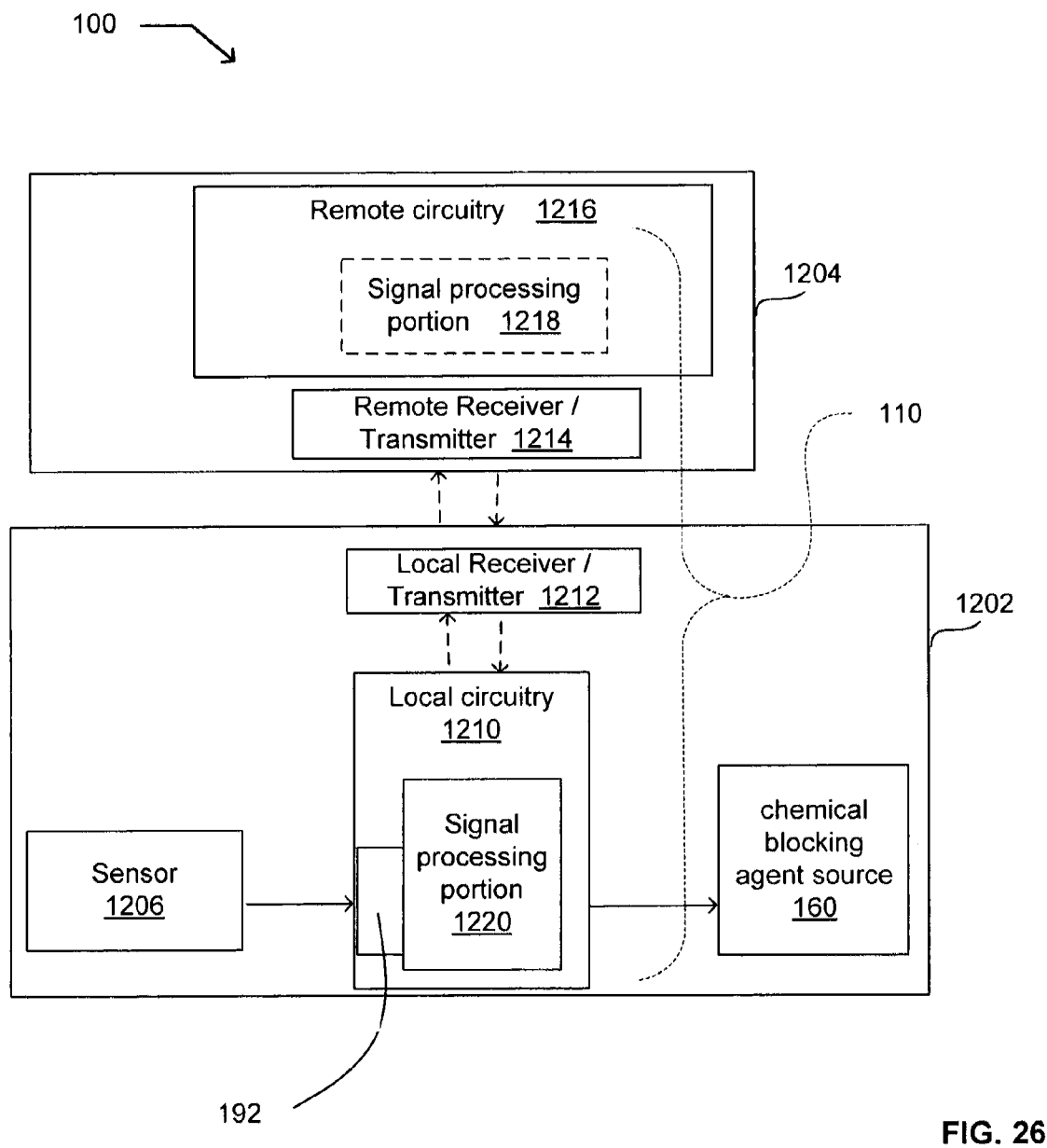
FIG. 26 is a block diagram of a further example of a neural modulation system.

FIG. 26 depicts in further detail an example of a neural modulation system 100 in which components are packaged so that some can be used locally (e.g. implanted in the body or positioned on or near the body surface) while others are used remotely, which in this context may be in a separate package located relatively close by (i.e. in, on or near the body), or at a distant location such as across a room, in a separate room, or in a separate building). Neural modulation system 100 includes local portion 1202 and remote portion 1204. Local portion 1202 may be implanted in the body of a subject or positioned on or near the body surface, while remote portion 1204 may be located remotely from local portion 1202. Local portion 1202 may include sensor 1206 and chemical blocking agent source 160. Local portion 1202 may also include local circuitry portion 1210 and local receiver/transmitter 1212. A corresponding remote receiver/transmitter 1214 in remote portion 1204 permits the transmission of data and instructions between local portion 1202 and remote portion 1204. In some embodiments, power may also be transmitted between remote portion 1204 and local portion 1202. Alternatively, or in addition, one or both of local portion 1202 and remote portion 1204 may include a power source (e.g., a battery or other power source as known to those of skill in the art). Remote portion 1204 may include remote circuitry 1216, which may include signal processing portion 1218. The signal processing portion of the system may include only signal processing portion 1218 in remote portion 1204, or it may include both signal processing portion 1218 in remote portion 1204 and signal processing circuitry 1220 in local portion 1202. Alternatively, in some embodiments, the signal processing portion may include signal processing portion 1220 in local portion 1202 and remote circuitry 1216 may be devoted to other functions.

Components packaged separately may be operatively connected to other components by cables, a wireless link (which may be optical, electromagnetic, acoustic, etc.). Separately packaged components may be suited for use outside or inside the body. In some embodiments, some components may be positioned inside the body while other are positioned outside the body during use. In some embodiments, the signal processing portion may be configured to perform encryption of signals transmitted to separately packaged and/or remote components or device portion, e.g. a chemical blocking agent control signal. Similarly, the signal processing portion may be configured to perform decryption of signals received from, e.g., a user input device, via a signal input structure or override signal input structure. Encryption/decryption may be performed by standard methods as known to those of skill in the art, for example, as used in computers, networks, mobile telephones, wireless microphones, wireless intercom systems, Bluetooth devices, and so forth. Encryption/decryption may be used in order to provide secure transmission of information, for example for protecting privacy of personal information and/or for avoiding interference between multiple devices used in the same area.

Figure 27:
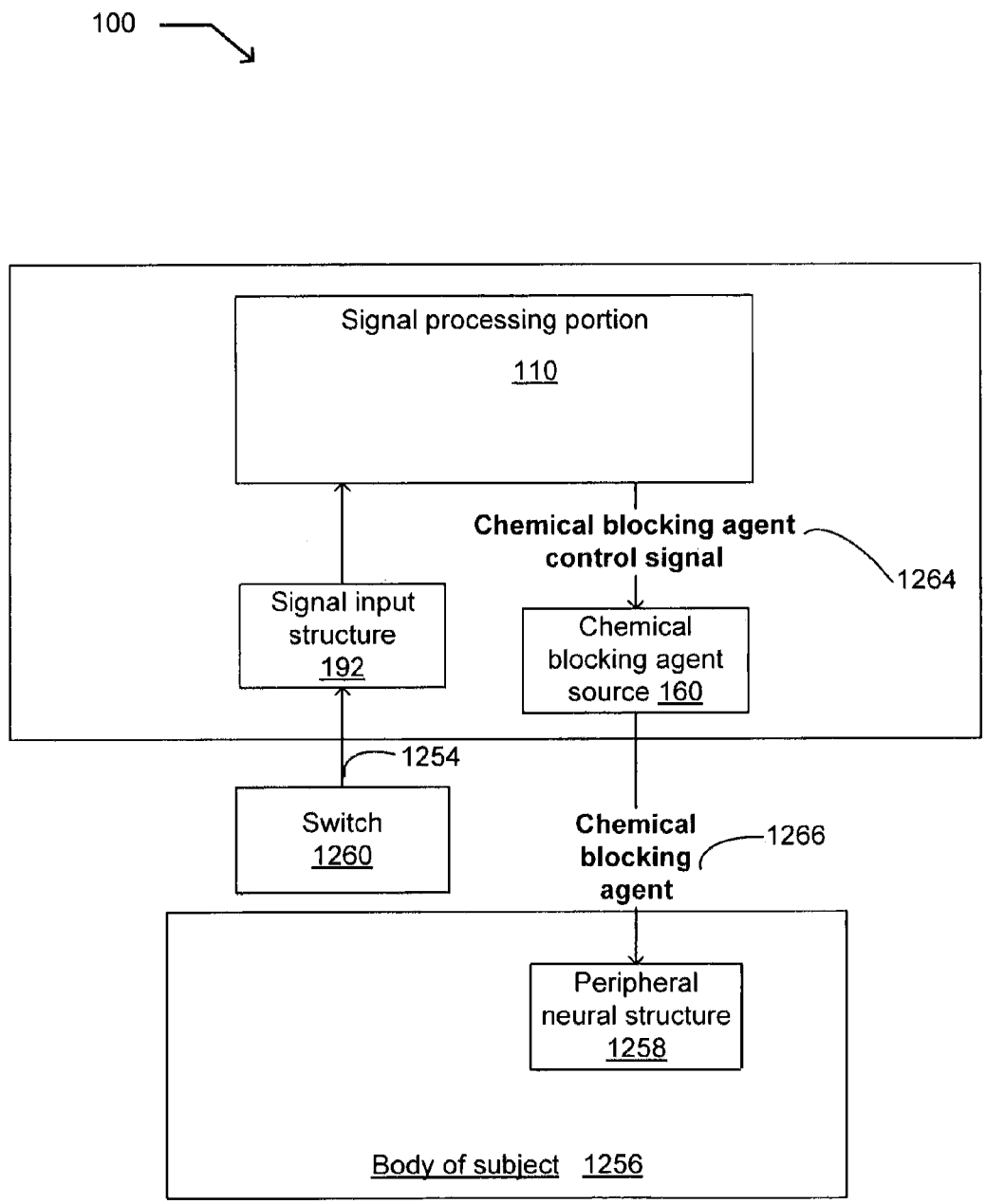
FIG. 27 is a block diagram of a further example of a neural modulation system.

In some embodiments, a user input device may be used in place of (or in addition to) a sensor in order to provide indication of an activity or use state of all or a portion of the body of the subject. Such a system is depicted in schematic form in FIG. 27. As shown in FIG. 27, neural modulation system 100 may include a signal input structure 192 configured to receive a signal 1254 indicative of an activity state of at least a portion of a body of a subject 1256 innervated by a peripheral neural structure 1258; a user input device (switch 1260) operatively connected to the signal input structure 192 and configured to generate a signal 1254 responsive to a user input indicative of an activity state of at least a portion of the body of a subject 1256 innervated by the peripheral neural structure 1258. For example, switch 1260 may be set to the "on" setting when the subject is entering a first activity state, and set to the "off" setting when the subject is entering a second activity state. Neural modulation system 100 also includes signal processing portion 110 configured to distinguish a first activity state of the at least a portion of the body of the subject 1256 innervated by the peripheral neural structure 1258 from a second activity state of the at least a portion of the body of the subject 1256 innervated by the peripheral neural structure 1258 from the signal 1254 received at the signal input structure 192 (e.g., by detecting the "on" or "off" setting of switch 1260); and generate a chemical blocking agent control signal 1264 for driving delivery of a chemical blocking agent 1266 configured to reversibly block conduction in the peripheral neural structure 1258 of the body of subject 1256 during at least a portion of the first activity state. Chemical blocking agent 1266 is delivered by a chemical blocking agent source 160 responsive to chemical blocking agent control signal 1264.

A user of the neural modulation system depicted in FIG. 27 (the subject or another party, such as a medical care-giver or assistant) may use user input device (e.g., switch 1260) to indicate that the subject is currently resting or inactive (e.g., sitting in a chair or lying in bed) or about to begin a period of rest or inactivity, e.g., by changing the setting of switch, as described above. Similarly, a user of the system may also use the user input device to indicate the end of a period of rest or inactivity. The user input device may include various types of user input devices, as are known to those of skill in the art. For example, the user input device may include one or more of the following: a voice-activated or other sound-activated input device, e.g. a microphone, a user-activated switch or knob, a keyboard, a mouse or other pointing device, a touch-screen or other user activated input devices.

The foregoing are examples, and various other devices that allow the subject or other user to signal a change (or expected change) in activity state may be used in practice.

As discussed in connection with systems in which sensors are used to provide indication of an activity or use state of all or a portion of the body of the subject, the various components of the system may be packaged together or separately, located locally or remotely, inside or outside the body of the subject, as depicted in FIGS. 23-28. For example, FIG. 27 shows an example of a neural modulation system in which switch 1260 is packaged separately from the signal processing portion 110 and is located outside of the body of subject 1256, while chemical blocking agent source 160 is packaged with signal processing portion 110. Signal processing portion 110 and chemical blocking agent source 160 may be in a package configured to be placed against the subject's body as the subject rests, while switch 1260 may be connected to signal processing portion 110 with a cable, for example (or, alternatively, a wireless connections such as an optical or RF connection). The subject may toggle switch 1260 to indicate the beginning or end of a rest period during which the chemical blocking agent is to be delivered. Chemical blocking agent source 160 may be configured to generate a chemical blocking agent sufficient to block conduction in peripheral neural structure. Peripheral neural structure 1258 may be blocked with the goal of producing a particular beneficial effect, such as to limit the progression of an inflammatory process (e.g. in diabetes, arthritis, vascular disease).

Figure 28:
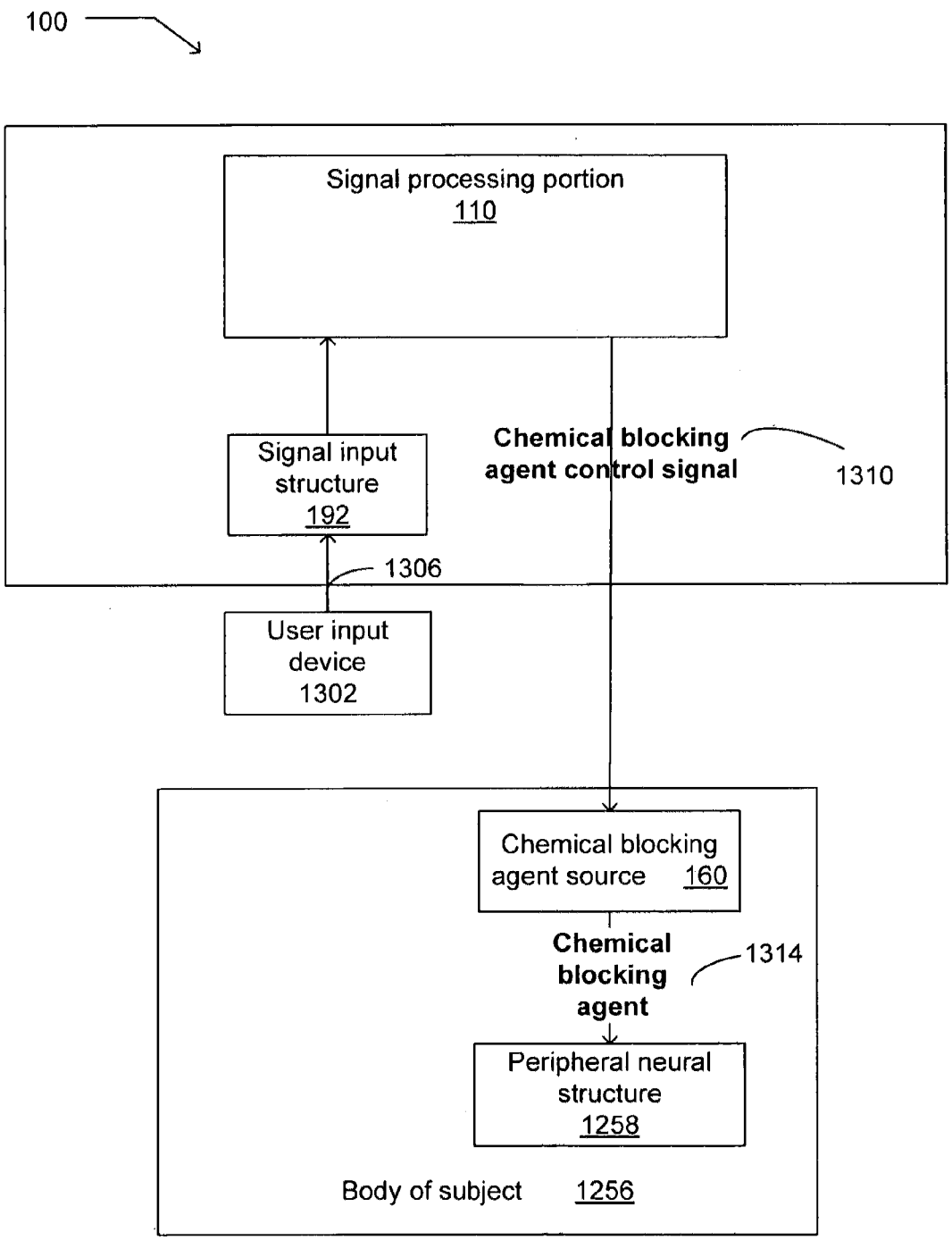
FIG. 28 is a block diagram of another example of a neural modulation system.

FIG. 28 depicts a further example of a neural modulation system 100 in which user input device 1302 is packaged separately from signal processing portion 110, providing signal 1306 to signal input structure 192. Signal processing portion 110 generates chemical blocking agent control signal 1310, which is provided (e.g., transmitted) to chemical blocking agent source 160, which is implanted within the body of subject 1256. As discussed previously, chemical blocking agent source 160 delivers chemical blocking agent 1314 for blocking conduction in peripheral neural structure 1258 in body of subject 1256. Other arrangements of system components are possible, and systems as described generally herein are not limited to the specific arrangements of components depicted in the figures.

Figure 29:
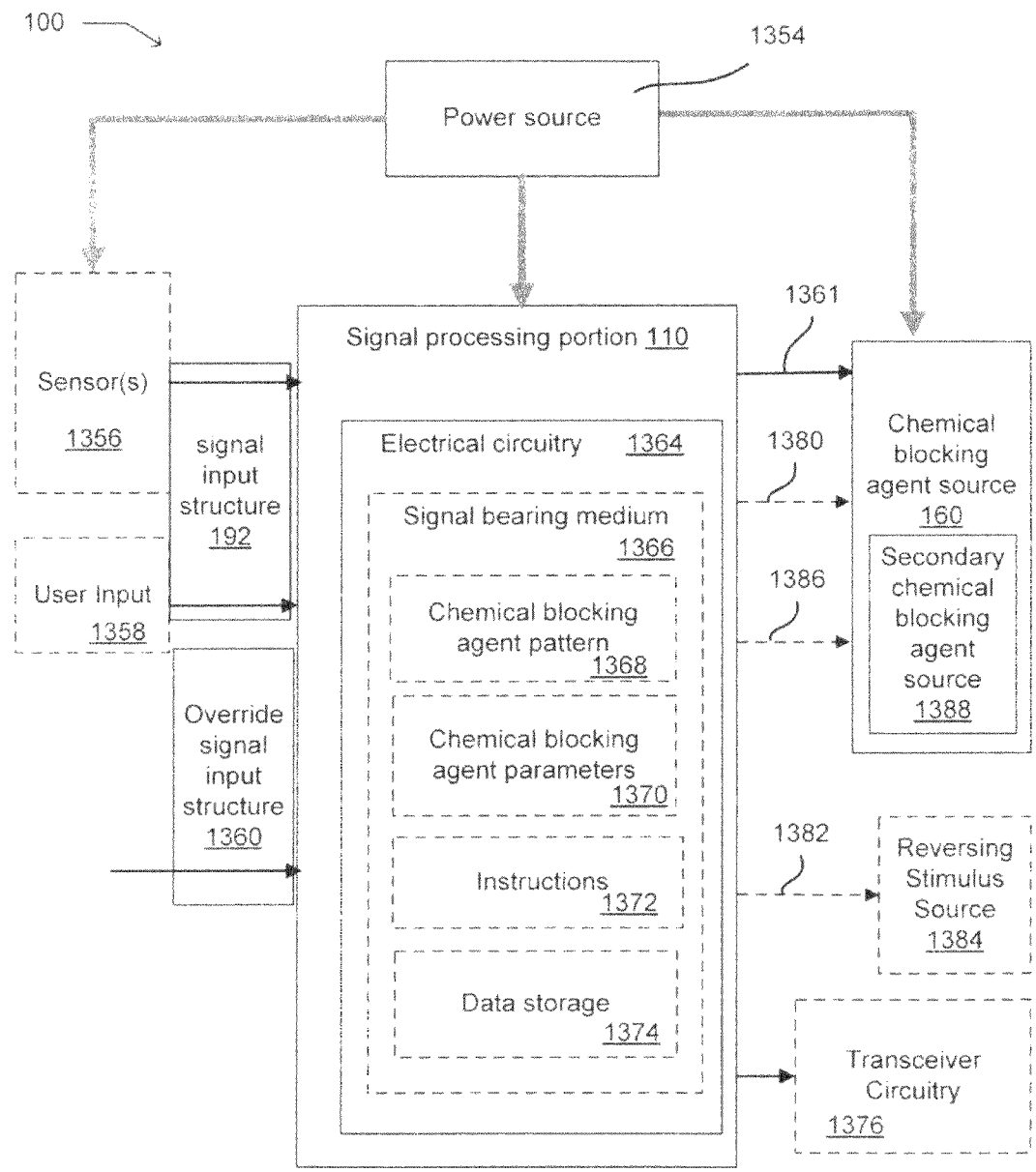
FIG. 29 is a block diagram of a signal processing portion of a neural modulation system.

A schematic diagram showing components and operation of a signal processing portion 110 of a neural modulation system 100 is shown in FIG. 29. The functional relationship of signal processing portion 110 to other components of neural modulation system 100 is also shown. As noted previously, signal processing portion 110 and other system components may be powered by a single power source, as shown in FIG. 28 as power source 1354; or multiple power sources. Signal processing portion 110 may receive as input signals from one or more sensors 1356 and/or one or more user input devices 1358 via signal input structure 192, and optionally, a signal from override signal input structure 1360. Signal processing portion 110 may generate as output chemical blocking agent control signal 1361 for driving chemical blocking agent source 160 to deliver a chemical blocking agent.

Signal processing portion 110 may include electrical circuitry 1364 for performing signal processing functions including but not limited to amplification, filtering, signal averaging, thresholding, variable-changing, waveform analysis, variable (e.g., time- or spatial-frequency) domain transformation, convolution, cross-spectral analysis, feature or pattern recognition or extraction, processing performed relative to data-stored-in-memory, etc., or a combination or concatenation of any or all of these, as is known to those of skill in the art of signal processing, whether such operations may be done in software, firmware or hardware or combinations of these. Electrical circuitry 1364 may also be configured to generate chemical blocking agent control signal 1361 for driving chemical blocking agent source 160. In some embodiments, chemical blocking agent control signal 1361 may include a primary chemical blocking agent control signal for driving primary chemical blocking agent source 160, and electrical circuitry 1364 may also be configured to generate secondary chemical blocking agent control signal 1386 for driving secondary chemical blocking agent source 1388. Detection of the onset or end of an activity state is not limited to threshold-based determinations, but may include various other types of signal processing as known to those of skill in the art; for example analysis of the trend of the signal may be used to predict the onset of an activity state. Accordingly, operations performed in response to detection or determination of the onset of a particular activity state may in some cases be based upon the predicted onset of an activity state, and may occur before, after, or simultaneously with the predicted onset of an activity state. Electrical circuitry or other components of a signal processing portion may accordingly be configured to cause delivery of a chemical blocking agent or to initiate a release period prior to, simultaneously with, or subsequently to the predicted the onset of an activity state in the subject.

The chemical blocking agent may be delivered with a repetitive or cyclical delivery pattern according to a detected signal indicative of at least one activity state in the subject and/or according to a pre-set schedule. Signal processing portion 110 may include at least one signal bearing medium 1366 that may contain chemical blocking agent pattern 1368, which specifies the pattern of delivery of a chemical blocking agent, as a function of time, and, in some cases, spatial location. Signal bearing medium 1366 may also include chemical blocking agent parameters 1370 related to generating chemical blocking agent control signal 1361 according to a detected signal from sensor 1356 or user input 1358. Stimulus parameters 1370 may include constants and/or variables to be used in calculations of chemical blocking agent control signal 1360 as a function of the detected signal. Signal bearing medium 1366 may include instructions 1372, which may relate to one or more of receiving or acquiring signals on signal input structure 192, processing the signals, generating chemical blocking agent control signal 1361, storing data (e.g. signals or parameters representing some or all of sensor or user input, chemical blocking agent control signal, etc.) in data storage location 1374, and instructions related to transmitting and/or receiving data or instructions via transmitter/receiver circuitry 1376. Electrical circuitry 1364 and signal bearing medium 1366 may optionally include instructions, patterns, and/or parameters for use in generating release stimulus control signal 1380 for producing discontinuation of delivery of a chemical blocking agent by chemical blocking agent source 160, and instruction, patterns, and/or parameters for use in generating reversing stimulus control signal 1382 for driving generation of a reversing stimulus by reversing stimulus source 1384.

In a general sense, those skilled in the art will recognize that the various aspects described herein that can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program that at least partially carries out processes and/or devices described herein, or a microprocessor configured by a computer program that at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Operation of neural modulation devices as described herein may be performed under the control of hardware (e.g. analog or digital electronic circuitry). Circuitry for switching, signal generation, sensing, timing control etc. is well known and may be constructed by those of skill in the art of electronics. In some embodiments, control of neural modulation devices as described herein may be performed under microprocessor control. Instructions to be executed by a microprocessor may be stored in hardware, firmware, or software (e.g. as an ASIC, instructions burned into an EEPROM, instructions stored in various types of memory devices/structures) on various types of signal-bearing media. Instructions for controlling neural modulation devices as described herein may be used, for example to implement methods as outlined, e.g. in FIGS. 5, 7, 8, and 14, 16, 18, 19, and 21. Instructions carried on a signal bearing medium may form a permanent or temporary component of a system including additional device components. Signal bearing media used, e.g. as depicted in FIG. 29, may include both instructions for controlling neural modulation device, and also stored data or parameters. Data, parameters, and instructions may be stored on more than one types of media during the practice of the invention (e.g., partially in device memory, partially on a removable medium, etc.).

Methods as described herein may include storing or saving information regarding device operation on the device, or transmitting such information to a remote location for storage or evaluation. Information may include, but is not limited to including device settings, parameters and other information relating to production of blocking and reversing stimuli, and sensed activity level or activity state of a subject, regarding producing a reversible conduction block.

A signal processing portion used in various embodiments as disclosed herein may be configured to perform the various described steps by appropriately configured analog or digital hardware, by instructions encoded in software or firmware, or combinations thereof, or by other methods as are known to those of skill in the art. Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

The contents of the publications, journal articles, books, patents, and published patent applications referenced herein are incorporated herein by reference to the extent that they do not conflict with the instant disclosure.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." Those skilled in the art will recognize that "configured to" can generally encompass active-state components and/or inactive-state components and/or standby-state components, etc. unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim 1ncludes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A neural modulation system comprising:
   a signal input structure configured to receive a signal indicative of an activity state of at least a portion of a body of a subject innervated by a peripheral neural structure;
   a signal processing portion configured to:
   distinguish a low activity state of the at least a portion of the body of the subject innervated by the peripheral neural structure from a higher activity state of the at least a portion of the body of the subject innervated by the peripheral neural structure from the signal received at the signal input structure; and
   generate a chemical blocking agent control signal for driving delivery of a chemical blocking agent adapted to reversibly block conduction in the peripheral neural structure of the subject during at least a portion of the low activity state; and
   a chemical blocking agent source configured to deliver the chemical blocking agent responsive to the chemical blocking agent control signal.

2. The neural modulation system of claim 1, including a sensor operatively connected to the signal input structure and configured to generate the signal indicative of the activity state of the at least a portion of the body of the subject innervated by the peripheral neural structure responsive to an activity of the at least a portion of the body of the subject.

3. The neural modulation system of claim 1, wherein the chemical blocking agent source is configured to produce blockage of a subset of nerve fibers in the peripheral neural structure of the subject responsive to the chemical blocking agent control signal.

4. The neural modulation system of claim 3, wherein the subset of nerve fibers in the peripheral neural structure of the subject includes at least one of nerve fibers within a selected diameter range, nerve fibers within a selected spatial distribution within the peripheral neural structure, or nerve fibers including a selected molecular feature.

5. The neural modulation system of claim 1, wherein the chemical blocking agent source is configured to deliver two or more chemical agents.

6. The neural modulation system of claim 1, wherein the chemical blocking agent source is configured to deliver one or more chemical agents at two or more locations.

7. The neural modulation system of claim 1, wherein the signal processing portion is configured to:
   determine an onset of the low activity state; and generate the chemical blocking agent control signal for driving delivery of the chemical blocking agent adapted to reversibly block conduction in the peripheral neural structure of the subject at least intermittently responsive to detecting the onset of a low activity state in the subject.

8. The neural modulation system of claim 7, wherein the signal processing portion is configured to:
   initiate a release period during which no chemical blocking agent control signal is generated after an interval determined relative to an onset of generation of the chemical blocking agent control signal.

9. The neural modulation system of claim 7, wherein the signal processing portion is configured to generate the chemical blocking agent control signal for driving delivery of the chemical blocking agent adapted to reversibly block conduction in the peripheral neural structure of the subject at a time selected from substantially immediately upon detecting the onset of the low activity state in the subject and at a delay interval after detecting the onset of the low activity state in the subject.

10. The neural modulation system of claim 1, wherein the signal processing portion is configured to:
    predict an onset of the low activity state; and generate the chemical blocking agent control signal for driving delivery of the chemical blocking agent adapted to reversibly block conduction in the peripheral neural structure of the subject at least intermittently relative to the predicted onset of the low activity state in the subject.

11. The neural modulation system of claim 10, wherein the signal processing portion is configured to generate the chemical blocking agent control signal for driving delivery of the chemical blocking agent adapted to reversibly block conduction in the peripheral neural structure of the subject at least intermittently at a time selected from prior to the predicted onset of the low activity state in the subject, substantially simultaneously with the predicted onset of the low activity state in the subject, and subsequent to the predicted onset of the low activity state in the subject.

12. The neural modulation system of claim 1, wherein the signal processing portion is configured to:
 determine an onset of the higher activity state in the subject; and
 initiate a release period during which no chemical blocking agent control signal is generated responsive to detecting the higher activity state in the subject.

13. The neural modulation system of claim 12, wherein the signal processing portion is configured to:
 initiate the release period at a time selected from substantially immediately upon detection of the onset of the higher activity state in the subject and at a delay interval after detection of an onset of the higher activity state in the subject.

14. The neural modulation system of claim 1, wherein the signal processing portion is configured to:
 predict the onset of the higher activity state in the subject; and
 initiate a release period during which no chemical blocking agent control signal is generated relative to a predicted onset of the higher activity state in the subject.

15. The neural modulation system of claim 14, wherein the signal processing portion is configured to:
 initiate the release period at a time selected from at an interval prior to the predicted onset of the higher activity state in the subject, substantially simultaneously with the predicted onset of the higher activity state in the subject, and at a delay interval after the predicted onset of the higher activity state in the subject.

16. The neural modulation system of claim 1, wherein the signal processing portion is configured to generate a release stimulus control signal for controlling discontinuation of delivery of the chemical blocking agent when the subject is in a higher activity state.

17. The neural modulation system of claim 16, wherein the signal processing portion is configured to repetitively generate the chemical blocking agent control signal for driving delivery of the chemical blocking agent adapted to reversibly block conduction in the peripheral neural structure of the subject during at least a portion of the low activity state and generate the release stimulus control signal for controlling discontinuation of delivery of the chemical blocking agent when the subject is in the higher activity state.

18. The neural modulation system of claim 17, wherein the signal processing portion is configured to repetitively generate the chemical blocking agent control signal for driving delivery of the chemical blocking agent adapted to reversibly block conduction in the peripheral neural structure of the subject during at least a portion of the low activity state and generate the release stimulus control signal for controlling discontinuation of delivery of the chemical blocking agent when the subject is in the higher activity state cyclically, wherein each cycle includes a blocking period during which the chemical blocking agent sufficient to produce reversible conduction block in the peripheral neural structure of the subject is delivered while the subject is in the low activity state and a release period during which no chemical blocking agent is delivered.

19. The neural modulation system of claim 17, wherein the signal processing portion is configured to repetitively generate the chemical blocking agent control signal for driving delivery of the chemical blocking agent adapted to reversibly block conduction in the peripheral neural structure of the subject during at least a portion of the low activity state and generate the release stimulus control signal for controlling discontinuation of delivery of the chemical blocking agent when the subject is in the higher activity state in alternation according to a pre-set schedule.

20. The neural modulation system of claim 17, wherein the signal processing portion is configured to repetitively generate the chemical blocking agent control signal for driving delivery of the chemical blocking agent adapted to reversibly block conduction in the peripheral neural structure of the subject during at least a portion of the low activity state and generate the release stimulus control signal for controlling discontinuation of delivery of the chemical blocking agent when the subject is in the higher activity state over a period of time sufficient to produce modulation of at least one of an immune response or an inflammatory response in a region innervated by the peripheral neural structure.

21. The neural modulation system of claim 1, wherein the chemical blocking agent source includes:
 a primary chemical blocking agent source configured to deliver a primary chemical blocking agent component; and
 a secondary chemical blocking agent source configured to deliver a secondary chemical blocking agent component;
 wherein the primary chemical blocking agent component and the secondary chemical blocking agent component act together to reversibly block conduction in the peripheral neural structure, and wherein the signal processing portion is configured to generate a chemical blocking agent control signal including a primary chemical blocking agent control signal for driving delivery of the primary chemical blocking agent component and a secondary chemical blocking agent control signal for driving delivery of the secondary chemical blocking agent component.

22. The neural modulation system of claim 1, wherein the signal processing portion is configured to:
 determine that producing a reversible conduction block in the peripheral neural structure of the subject while the subject is in the low activity state results in a desired effect in the subject; and
 generate a non-reversible blocking source control signal for driving a non-reversible blocking source to perform an action adapted for producing a non-reversible conduction block in the peripheral neural structure of the subject; and
 wherein the neural modulation system further comprises the non-reversible blocking source configured to perform the action adapted for producing the non-reversible conduction block in the peripheral neural structure of the subject responsive to the non-reversible blocking source control signal.

23. The neural modulation system of claim 22, wherein the non-reversible blocking source includes at least one of a heat source, a cooling source, an electrical current source, an acoustic energy source, a photon source, a chemical agent source, or a surgical transection mechanism.

24. The neural modulation system of claim 22, wherein the non-reversible blocking source includes a heat source configured to produce thermal ablation of at least a portion of the peripheral neural structure of the subject.

25. The neural modulation system of claim 22, wherein the non-reversible blocking source includes a heat source that includes at least one of a Peltier device, a resistive element, a fluid heat-transfer device, or an exothermic reaction device.

26. The neural modulation system of claim 22, wherein the non-reversible blocking source includes a cooling source that includes at least one of a Peltier device, an endothermic reaction device, or a fluid heat-transfer device.

27. The neural modulation system of claim 1, wherein the chemical blocking agent source includes at least one of an iontophoresis device, an electroporation device, a sonophoresis device, a phonophoresis device, a microneedle array, a MEMS device, a plurality of microreservoirs, a chemical blocking agent in a polymeric matrix, or an infusion pump.

28. The neural modulation system of claim 1, wherein the chemical blocking agent source includes at least one of an electric field source, an electrical current source, a magnetic field source, an electromagnetic transducer, an acoustic energy source, or an ultrasonic acoustic energy source.

* * * * *